United States Patent
Klein et al.

(10) Patent No.: US 11,579,107 B2
(45) Date of Patent: Feb. 14, 2023

(54) SYSTEM AND METHOD FOR GMR-BASED DETECTION OF BIOMARKERS

(71) Applicant: ZEPTO LIFE TECHNOLOGY, LLC, St. Paul, MN (US)

(72) Inventors: Todd Michael Klein, Wayzata, MN (US); Michael Monroe Reinhart Sandstedt, Minneapolis, MN (US); John Frank Provos, Hudson, WI (US); Chad Brian Rheault, Newport, MN (US)

(73) Assignee: ZEPTO LIFE TECHNOLOGY, INC., St. Paul, MN (US)

( * ) Notice: Subject to any disclaimer, the term of this patent is extended or adjusted under 35 U.S.C. 154(b) by 0 days.

(21) Appl. No.: 16/766,126

(22) PCT Filed: Jul. 26, 2019

(86) PCT No.: PCT/US2019/043720
§ 371 (c)(1),
(2) Date: May 21, 2020

(87) PCT Pub. No.: WO2020/023903
PCT Pub. Date: Jan. 30, 2020

(65) Prior Publication Data
US 2021/0138462 A1 May 13, 2021

Related U.S. Application Data

(60) Provisional application No. 62/711,396, filed on Jul. 27, 2018.

(51) Int. Cl.
*B01L 3/00* (2006.01)
*G01N 27/12* (2006.01)
(Continued)

(52) U.S. Cl.
CPC .......... *G01N 27/12* (2013.01); *B01L 3/50273* (2013.01); *B01L 3/502715* (2013.01);
(Continued)

(58) Field of Classification Search
CPC ......... B01L 2200/14; B01L 2400/0487; B01L 2300/025; B01L 2300/14;
(Continued)

(56) References Cited

U.S. PATENT DOCUMENTS

| 5,646,001 A | 7/1997 | Terstappen et al. |
| 6,426,043 B1 * | 7/2002 | Cohen .................... G01N 35/04 |
| | | 422/561 |

(Continued)

FOREIGN PATENT DOCUMENTS

| JP | 2008522151 A | 6/2008 |
| JP | 2009511860 A | 3/2009 |

(Continued)

OTHER PUBLICATIONS

Extended European Search Report dated Apr. 21, 2021 in European Application 19816193.7.

(Continued)

*Primary Examiner* — Shogo Sasaki
(74) *Attorney, Agent, or Firm* — Venable LLP

(57) ABSTRACT

A system for detecting analytes in a test sample, and a method for processing the same, is provided. The system includes a cartridge reader unit that has a control unit and a pneumatic system, and a cartridge assembly that prepares the samples with mixing material(s) through communication channels. The assembly has a memory chip with parameters for preparing the sample and at least one sensor (GMR sensor) for detecting analytes in the sample. The assembly is pneumatically and electronically mated with the reader unit via a pneumatic interface and an electronic interface such (Continued)

that the parameters may be implemented via the control unit. The pneumatic system is contained within the unit and has pump(s) and valve(s) for selectively applying fluid pressure to the pneumatic interface of the assembly, and thus through the communication channels, to move the sample and mixing material(s) through and to sensor. The control unit activates the pneumatic system to prepare the sample and provide it to the sensor for detecting analytes, and also processes measurements from the sensor to generate test results.

20 Claims, 37 Drawing Sheets

(51) Int. Cl.
  *G01N 33/18* (2006.01)
  *G01N 33/487* (2006.01)
  *G01N 33/49* (2006.01)
  *G01N 33/543* (2006.01)
  *G01N 27/74* (2006.01)
  *G01N 33/493* (2006.01)
  *G01R 33/09* (2006.01)
  *G01R 33/12* (2006.01)
(52) U.S. Cl.
  CPC .............. *B01L 3/567* (2013.01); *G01N 27/74* (2013.01); *G01N 27/745* (2013.01); *G01N 33/1813* (2013.01); *G01N 33/48707* (2013.01); *G01N 33/49* (2013.01); *G01N 33/493* (2013.01); *G01N 33/54306* (2013.01); *G01R 33/093* (2013.01); *G01R 33/1269* (2013.01); *G01R 33/1276* (2013.01); *B01L 2200/026* (2013.01); *B01L 2200/027* (2013.01); *B01L 2200/04* (2013.01); *B01L 2200/0684* (2013.01); *B01L 2200/14* (2013.01); *B01L 2200/16* (2013.01); *B01L 2300/025* (2013.01); *B01L 2300/0663* (2013.01); *B01L 2300/0681* (2013.01); *B01L 2300/0816* (2013.01); *B01L 2300/0819* (2013.01); *B01L 2300/0883* (2013.01); *B01L 2300/0887* (2013.01); *B01L 2300/123* (2013.01); *B01L 2300/14* (2013.01); *B01L 2400/043* (2013.01); *B01L 2400/0487* (2013.01); *B01L 2400/06* (2013.01)
(58) Field of Classification Search
  CPC ....... B01L 2300/0887; B01L 2400/043; B01L 3/567; B01L 2300/0681; B01L 2300/0883; B01L 3/50273; B01L 3/502715; B01L 2200/0684; B01L 2300/0816; B01L 2200/026; B01L 2200/027; B01L 2300/0663; B01L 2200/04; B01L 2300/0819; B01L 2400/06; B01L 2200/16; B01L 2300/123; G01R 33/093; G01R 33/0041; G01R 33/09; G01R 33/091; G01R 33/1276; G01R 33/1269; G01N 27/74; G01N 35/00029; G01N 33/48707; G01N 2035/00148; G01N 33/49; G01N 33/54366; G01N 27/12; G01N 35/1097; G01N 2001/386; G01N 33/493; G01N 33/543; G01N 33/1813; G01N 33/84; G01N 33/54326; G01N 27/745; G01N 35/0098; G01N 33/54306
  See application file for complete search history.

(56) References Cited

U.S. PATENT DOCUMENTS

| | | | |
|---|---|---|---|
| 6,437,563 | B1 | 8/2002 | Simmonds et al. |
| 10,688,493 | B2* | 6/2020 | Kim .................. B01L 3/502738 |
| 2003/0044323 | A1* | 3/2003 | Diamond ............... G01N 35/10 |
| | | | 211/74 |
| 2008/0129286 | A1 | 6/2008 | Kahlman et al. |
| 2008/0190735 | A1* | 8/2008 | Luoma ................. G01N 35/026 |
| | | | 422/65 |
| 2008/0246471 | A1 | 10/2008 | Kahlman et al. |
| 2008/0278156 | A1 | 11/2008 | De Boer |
| 2008/0309329 | A1 | 12/2008 | Kahlman et al. |
| 2009/0066318 | A1 | 3/2009 | Kahlman et al. |
| 2009/0163785 | A1* | 6/2009 | Nelson ................. A61B 5/0059 |
| | | | 600/322 |
| 2009/0184706 | A1 | 7/2009 | Duric et al. |
| 2010/0259250 | A1 | 10/2010 | Kahlman |
| 2010/0267169 | A1 | 10/2010 | Hajimiri et al. |
| 2012/0115214 | A1 | 5/2012 | Battrell et al. |
| 2013/0331298 | A1 | 12/2013 | Rea |
| 2014/0178900 | A1 | 6/2014 | Jung et al. |
| 2014/0292318 | A1 | 10/2014 | Wang et al. |
| 2015/0197784 | A1 | 7/2015 | Wiliams et al. |
| 2015/0198594 | A1 | 7/2015 | Williams et al. |
| 2015/0338427 | A1* | 11/2015 | Pollack .............. G01N 35/0095 |
| | | | 422/67 |
| 2016/0011182 | A1 | 1/2016 | Qiu |
| 2016/0025756 | A1* | 1/2016 | Pollack ............ G01N 35/00732 |
| | | | 422/65 |
| 2016/0193603 | A1 | 7/2016 | Battrell et al. |
| 2016/0209405 | A1 | 7/2016 | Wang et al. |
| 2017/0097337 | A1 | 4/2017 | Shultz et al. |
| 2017/0113221 | A1 | 4/2017 | Hoffman et al. |
| 2017/0260567 | A1 | 9/2017 | Selden et al. |
| 2017/0312751 | A1 | 11/2017 | Glezer et al. |
| 2018/0021783 | A1 | 1/2018 | Arlett et al. |
| 2018/0067094 | A1 | 3/2018 | Sinha et al. |
| 2018/0299407 | A1 | 10/2018 | Haratani et al. |
| 2018/0314046 | A1* | 11/2018 | Sakurai .................. G02B 21/14 |

FOREIGN PATENT DOCUMENTS

| | | |
|---|---|---|
| JP | 2009511895 A | 3/2009 |
| JP | 2009530602 A | 8/2009 |
| JP | 2009-249512 A | 10/2009 |
| JP | 2009-250926 A | 10/2009 |
| JP | 2009539098 A | 11/2009 |
| JP | 2010500547 A | 1/2010 |
| JP | 2011-221017 A | 11/2011 |
| JP | 2012-516455 A1 | 7/2012 |
| JP | 2013-518289 A | 5/2013 |
| JP | 2016-509206 A | 3/2016 |
| JP | 2017-520239 A | 7/2017 |
| JP | 2018507403 A | 3/2018 |
| JP | 2017082227 A1 | 8/2018 |
| KR | 1020160080112 A | 7/2016 |
| WO | 2006059270 A1 | 6/2006 |
| WO | 2007042959 A1 | 4/2007 |
| WO | 2007092909 A2 | 8/2007 |
| WO | 2008101196 A1 | 8/2008 |
| WO | 2009024922 A2 | 2/2009 |
| WO | 2012085884 | 6/2012 |
| WO | 2016124907 A1 | 8/2016 |
| WO | 2018053501 A1 | 3/2018 |
| WO | 2018057647 A1 | 3/2018 |

OTHER PUBLICATIONS

Office Action dated Apr. 27, 2021 in Japanese Application 2019-560705.
Office Action dated May 18, 2021 in Japanese Application 2019-560698.
Notice of Allowance dated May 18, 2021 in Japanese Application 2019-560695.

(56) References Cited

OTHER PUBLICATIONS

International Search Report and Written Opinion dated May 8, 2019 in International Application PCT/US2019/021837.
International Preliminary Report on Patentability dated Sep. 22, 2020 in International Application PCT/US2019/021837.
International Search Report and Written Opinion dated Nov. 13, 2019 in International Application PCT/US2019/043720.
Office Action dated Feb. 23, 2022 in Canadian Patent Application No. 3,106,680.
International Search Report and Written Opinion dated Nov. 15, 2019 in International Application PCT/US2019/043766.
International Preliminary Report on Patentability dated Feb. 11, 2021 in International Application PCT/US2019/043766.
International Preliminary Report on Patentability dated Feb. 11, 2021 in International Application PCT/US2019/043753.
International Preliminary Report on Patentability dated Feb. 11, 2021 in International Application PCT/US2019/043720.
International Search Report and Written Opinion dated Nov. 13, 2019 in International Application PCT/US2019/043791.
International Preliminary Report on Patentability dated Feb. 11, 2021 in International Application PCT/US2019/043791.
Office Action dated Feb. 2, 2021 in Japanese Application 2019-560695.
Office Action dated Feb. 2, 2021 in Japanese Application 2019-560691.
Extended European Search Report dated Mar. 15, 2021 in European Application 19816192.9.
Supplementary European Search Report dated Jan. 5, 2022 in EP Application No. 19816194.5.
Teh et al.: "Highly sensitive and selective detection of Pb 2+ ions using a novel and simple DNAzyme-based quartz crystal microbalance with dissipation biosensor", Analyst, vol. i 39, No. 20, Jan. 1, 2014, pp. 5170-5175.
Han et al.: "CMOS Integrated DNA Microarray Based on GMR Sensors", Electron Devices Meeting, 2006. IEDM '06. International, IEEE, PI, Dec. 1, 2006, pp. 1-4.
Han et al.: "Magnetic Nanotechnology for Biodetection", Journal of the Association for Laboratory Automation, Elsevier, vol. 15, No. 2, Apr. 1, 2010, pp. 93-98.
Huo et al: "A Novel High-Sensitivity Cardiac Multibiomarker Detection System Based on Microfluidic Chip and GMR Sensors", IEEE Transactions On Magnetics, IEEE Service Center, New York, NY, US, vol. 51, No. 11, Nov. 1, 2015 (Nov. 1, 2015), pp. 1-4.
Wu et al: "Comparison of Hydroxylated Print Additives on Antibody Microarray Performance", Journal of Proteome Research, vol. 5, No. ii, Oct. 19, 2006, pp. 2956-2965.
Chu et al.: "Bioconjugated Magnetic Nanoparticles for the Detection of Bacteria", Journal of Biomedical Nanotechnology, American Scientific Publishers, US, vol. 9, No. 12, Jan. 1, 2013.
Gaster et al.: "Matrix-insensitive protein assays push the limits of biosensors in medicine", Nature Medicine, Oct. 11, 2009, pp. 1-7.
McGhee et al: "DNAzyme sensors for detection of metal ions in the environment and imaging them in living cells", Current Opinion in Biotechnology, London, GB, vol. 45, Apr. 28, 2017, pp. 191-2001.
Wang et al: "Surface Modification for Protein and DNA null Immobilization onto GMR Biosensor", IEEE Transactions on Magnetics, IEEE Service Center, New York, NY, US, vol. 49, No. 1, Jan. 1, 2013 (Jan. 1, 2013), pp. 296-299.
Huo et al: "A novel high-sensitivity cardiac multi-biomarkers detecting system based on microfluidic chip and GMR sensor", 2015 IEEE Magnetics Conference (Intermag), IEEE, May 11, 2015 p. 1.
Office Action dated Mar. 18, 2022 in Canadian Patent Application No. 3,106,320.
Han et al., "A Novel Zero-Drift Detection Method for Highly Sensitive GMR Biochips", IEEE Transactions on Magnetics, IEEE, USA, vol. 42, No. 10, Oct. 1, 2006, pp. 3560-3562.
Yu et al.,"Giant Magnetoresistive Biosensors for Molecular Diagnosis: SurfaceChemistry and Assay Development", SPIE Digital Library, Aug. 2008, pp. 1-9, vol. 7035, Bellingham, WA, USA.

* cited by examiner (Cartridge reader flowchart)

| Step | Ports | Setting | Units | Time step (s) | Actuation time | Purpose |
|---|---|---|---|---|---|---|
| 1 | none | none | none | 1 | 0 | Place card in manifold with interface to ports on card |
| 2 | PV1,PV2,PV5,PV6 | 5.0 | psi | 2 | 1 | Load whole blood in chamber above filter. Load bead reagent and wash buffer in their wells |
| 3 | PV1 | -5.0 | psi | 2 | 3 | Start pneumatics control program. Close all valves. |
| 4 | F1, F3, F5 | 2.0 | uL/min | 10 | 5 | Open valves between sample filter and antibody rehydration channels. |
| 5 | F1, F3, F5 | 0.0 | uL/min | 2 | 15 | Pull plasma sample to channels to rehydrate dried antibodies. |
| 6 | PV1 | 5.0 | psi | 2 | 15 | As each channel fills, block flow to the port and vent the syringe barrel. |
| 7 | F1, F3, F5 | vent | psi | 2 | 17 | Close valves between sample filter and antibody rehydration channels. Vent the antibody rehydration channels at the GPMs. |
| 8 | PV6 | -5.0 | psi | 2 | 19 | Open valves between rehydration channels and GMR sensor channels. |
| 9 | F2, F4, F6 | 2.0 | uL/min | 900 | 21 | Pull sample/antibody solution to GMR sensors and on to waste. |
| 10 | F2, F4, F6 | 0.0 | uL/min | 2 | 921 | Block flow of sample/antibody solution to GMR sensors and on to waste. Close valves between rehydration channels and GMR sensor channels. |
| 11 | PV6 | 5.0 | psi | 2 | 923 | |
| 12 | PV1,PV5 | -5.0 | psi | 2 | 925 | Open valves to bead solution well. |
| 13 | F2, F4, F6 | 2.0 | uL/min | 900 | 927 | Pull bead solution to sensor channels and waste tanks. |
| 14 | F2, F4, F6 | 0.0 | uL/min | 2 | 1827 | Back flow to sensor channels and waste tanks. |
| | PV1,PV2,PV5,PV6 | 5.0 | psi | 2 | 1829 | Open all valves. Remove card from manifold. |

PV (PV1, PV2, etc.) = port connected to valves V
F (F1, F2, F3, etc.) = port connected to pump SP

Fig. 31

SYSTEM AND METHOD FOR GMR-BASED DETECTION OF BIOMARKERS

CROSS REFERENCE TO RELATED APPLICATIONS

This application a national stage application, filed under 35 U.S.C. § 371, of International Application No. PCT/US2019/043720, filed on Jul. 26, 2019, which claims priority to U.S. Provisional Patent Application No. 62/711,396, filed Jul. 27, 2018, both of which are incorporated herein by reference in their entireties.

BACKGROUND

Field

The present disclosure is generally related to a system for the detection of analytes. In particular, the present invention relates to a mobile system including a unit and a cartridge assembly that can be used for the detection of various analytes such as metal, biomarkers, and the like.

Description of Related Art

Generally, it is common to use a card to test for biomarker(s), metal, etc. in a blood sample. Adding a blood sample to known cards generally relies simply on lateral flow of the blood sample into the card before a reading is performed. Also, current assay systems in the medical market generally rely on capillary separation of a whole blood sample, which generally limits detection methodology to optical analysis or visual testing.

SUMMARY

Embodiments herein relate to devices for detection of analytes in a sample with magnetoresistive sensor technologies. For explanatory purposes, in accordance with embodiments, the devices, systems, and features are described with respect to utilizing a giant magnetoresistance (GMR) sensor platform.

It is an aspect of this disclosure to provide a system for detecting analytes in a test sample. The system includes: a cartridge reader unit comprising a control unit and a pneumatic system; and a cartridge assembly configured to receive and prepare the test sample with one or more mixing materials through communication channels therein. The cartridge assembly has a pneumatic interface and an electronic interface, as well as a memory chip having parameters associated with preparing the test sample and at least one sensor for detecting the analytes in the test sample. The cartridge assembly is configured for pneumatically and electronically mating with the cartridge reader unit via the pneumatic interface and the electronic interface such that the parameters associated with preparing the test sample from the memory chip are read and implemented via the control unit of the cartridge reader unit. The pneumatic system is contained within the cartridge reader unit and has at least one pump and at least one valve for selectively applying fluid pressure to the pneumatic interface of the cartridge assembly and thus through the communication channels of the cartridge assembly to move the test sample and the one or more mixing materials through the communication channels and to the at least one sensor. The control unit is configured to activate the pneumatic system to prepare the test sample in the cartridge assembly and provide the test sample to the at least one sensor for detecting analytes and measurements. The control unit is further configured to process the measurements from the at least one sensor, as a result of the detected analytes, to generate test results.

Another aspect provides a method for processing a test sample to detect analytes using the above noted system for example. The method includes: establishing electrical and pneumatic connections between the cartridge reader unit and the cartridge assembly via the control unit; reading the parameters associated with the memory chip for preparing the test sample; and activating the pneumatic system, using the control unit, to prepare the test sample in the cartridge assembly and provide the test sample to the at least one sensor for detecting analytes and measurements, and further processing the measurements from the at least one sensor, as a result of the detected analytes, to generate test results.

Other aspects, features, and advantages of the present disclosure will become apparent from the following detailed description, the accompanying drawings, and the appended claims.

BRIEF DESCRIPTION OF THE DRAWINGS

Various embodiments of the present disclosure will be described herein below with reference to the Figures wherein:

FIG. 31 is a step chart providing a particular example of steps, commands, settings and times associated with one embodiment for processing a test sample using the herein disclosed cartridge assembly and cartridge reader unit of the system.

DETAILED DESCRIPTION

As evident by the drawings and below description, this disclosure relates to a sample handling system (or "system" as noted throughout this disclosure) which may be used for detecting presence of an analyte (or analytes) such as metal, biomarkers, and the like, in a sample. In an embodiment, this system, depicted as system 300 in FIG. 3, may include (1) a sample handling system or "cartridge assembly" that includes sample preparation microfluidic channel(s) and at least one sensing device (or sensor) for sensing biomarkers/analytes in a test sample, and (2) a data processing and display device or "cartridge reader unit" that includes a processor or controller for processing any sensed data of the sensing device of the cartridge assembly and a display for displaying a detection event. Together these two components make up the system. In an embodiment, these components may include variable features including, without limitation, one or more reagent cartridges, a cartridge for waste, and a flow control system which may be, for example, a pneumatic flow controller.

Generally, the process for preparing a sample in the cartridge assembly, in order for detection of analytes, biomarkers, etc. to happen by the assembly and output via the cartridge reader unit, is as-follows: A raw patient sample is loaded onto a card, optionally filtered via a filter membrane, after which a negative pressure generated by off-card pneumatics filters the sample into a separated test sample (e.g., plasma). This separated test sample is quantitated on-card through channel geometry. The sample is prepared on card by interaction with mixing materials (e.g., reagent(s) (which may be dry or wet), buffer and/or wash buffer, beads and/or beads solution, etc.) from a mixing material source (e.g., blister pack, storage chamber, cartridge, well, etc.) prior to flow over the sensor/sensing device. The sample preparation channels may be designed so that any number of channels may be stacked vertically in a card, allowing multiple patient samples to be used. The same goes for sensing microfluidic devices, which may also be stacked vertically. A sample preparation card, which is part of the cartridge assembly, includes one or more structures providing functionalities selected from filtering, heating, cooling, mixing, diluting, adding reagent, chromatographic separation and combinations thereof; and a means for moving a sample throughout the sample preparation card. Further description regarding these features is provided later below.

Figure 1:
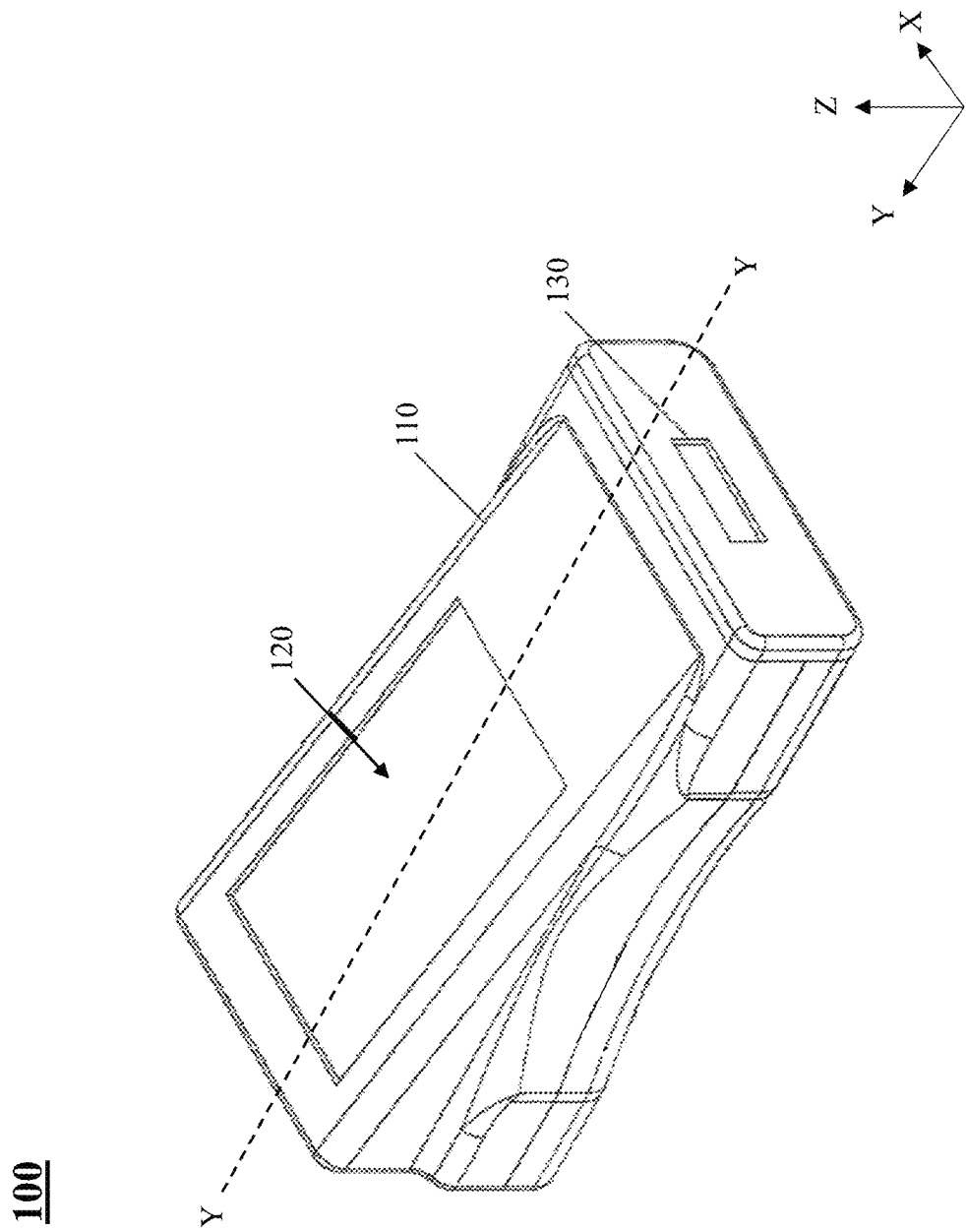
FIG. 1 is a perspective view of an exemplary cartridge reader unit used in a system in accordance with an embodiment of the present disclosure.

FIG. 1 shows an example of a cartridge reader unit 100, used in system 300 (see FIG. 3) in accordance with an embodiment. The cartridge reader unit 100 may be configured to be compact and/or small enough to be a hand-held, mobile instrument, for example. The cartridge reader unit 100 includes a body or housing 110 that has a display 120 and a cartridge receiver 130 for receiving a cartridge assembly. The housing 110 may have an ergonomic design to allow greater comfort if the reader unit 100 is held in an operator's hand. The shape and design of the housing 110 is not intended to be limited, however.

The cartridge reader unit 100 may include an interface 140 and a display 120 for prompting a user to input and/or connect the cartridge assembly 200 with the unit and/or sample, for example. In accordance with an embodiment, in combination with the disclosed cartridge assembly 200, the system 300 may process, detect, analyze, and generate a report of the results, e.g., regarding multiple detected biomarkers in a test sample, e.g., five cardiac biomarkers, using sensor (magnetoresistive) technology, and further display the biomarker results, as part of one process.

The display 120 may be configured to display information to an operator or a user, for example. The display 120 may be provided in the form of an integrated display screen or touch screen (e.g., with haptics or tactile feedback), e.g., an LCD screen or LED screen or any other flat panel display, provided on the housing 110, and (optionally) provides an input surface that may be designed for acting as end user interface (UI) 140 that an operator may use to input commands and/or settings to the unit 100, e.g., via touching a finger to the display 120 itself. The size of the display 120 may vary. More specifically, in one embodiment, the display 120 may be configured to display a control panel with keys, buttons, menus, and/or keyboard functions thereon for inputting commands and/or settings for the system 300 as part of the end user interface. In an embodiment, the control panel includes function keys, start and stop buttons, return or enter buttons, and settings buttons. Additionally and/or alternatively, although not shown in FIG. 1, the cartridge reader 100 may include, in an embodiment, any number of physical input devices, including, but not limited to, buttons and a keyboard. In another embodiment, the cartridge reader 100 may be configured to receive input via another device, e.g., via a direct or wired connection (e.g., using a plug and cord to connect to a computer (PC or CPU) or a processor) or via wireless connection. In yet another embodiment, display 120 may be to an integrated screen, or may be to an external display system, or may be to both. Via the display control unit 120, the test results (e.g., from a cartridge reader 310, described with reference to FIG. 3, for example) may be displayed on the integrated or external display. In still yet another embodiment, the user interface 140 may be provided separate from the display 120. For example, if a touch screen UI is not used for display 120, other input devices may be utilized as user interface 140 (e.g., remote, keyboard, mouse, buttons, joystick, etc.) and may be associated with the cartridge reader 100 and/or system 300. Accordingly, it should be understood that the devices and/or methods used for input into the cartridge reader 100 are not intended to be limiting. All functions of the cartridge reader 100 and/or system 300 may, in one embodiment, be managed via the display 120 and/or input device(s), including, but not limited to: starting a method of processing (e.g., via a start button), selecting and/or altering settings for an assay and/or cartridge assembly 200, selecting and/or settings related to pneumatics, confirming any prompts for input, viewing steps in a method of processing a test sample, and/or viewing (e.g., via display 120 and/or user interface 140) test results and values calculated by the (GMR) sensor and control unit/cartridge reader. The display 120 may visually show information related to analyte detection in a sample. The display 120 may be configured to display generated test results from the control unit/cartridge reader. In an embodiment, real-time feedback regarding test results that have been determined/processed by the cartridge reader unit/ controller (by receiving measurements from the sensing device, the measurements being determined as a result of the detected analytes or biomarkers), may be displayed on the display 120.

Optionally, a speaker (not shown) may also be provided as part of the cartridge reader unit 100 for providing an audio output. Any number of sounds may be output, including, but not limited to speech and/or alarms. The cartridge reader unit 100 may also or alternatively optionally include any number of connectors, e.g., a LAN connector and USB connector, and/or other input/output devices associated therewith. The LAN connector and/or USB connector may be used to connect input devices and/or output devices to the cartridge reader unit 100, including removable storage or a drive or another system.

In accordance with an embodiment, the cartridge receiver 130 may be an opening (such as shown in FIG. 1) within the housing 110 in which a cartridge assembly (e.g., cartridge assembly 200 of FIG. 2) may be inserted. In another embodiment, the cartridge receiver 130 may include a tray that is configured to receive a cartridge assembly therein. Such a tray (see, e.g., tray 610 in FIGS. 6, 10) may move relative to the housing 110, e.g., out of and into an opening therein, and to thereby receive the cartridge assembly 200 and move the cartridge assembly into (and out of) the housing 110. In one embodiment, the tray may be a spring-loaded tray that is configured to releasably lock with respect to the housing 110. Additional details associated with the cartridge reader unit 100 are described later with respect to FIG. 3 and FIGS. 5-17B.

Figure 2A:
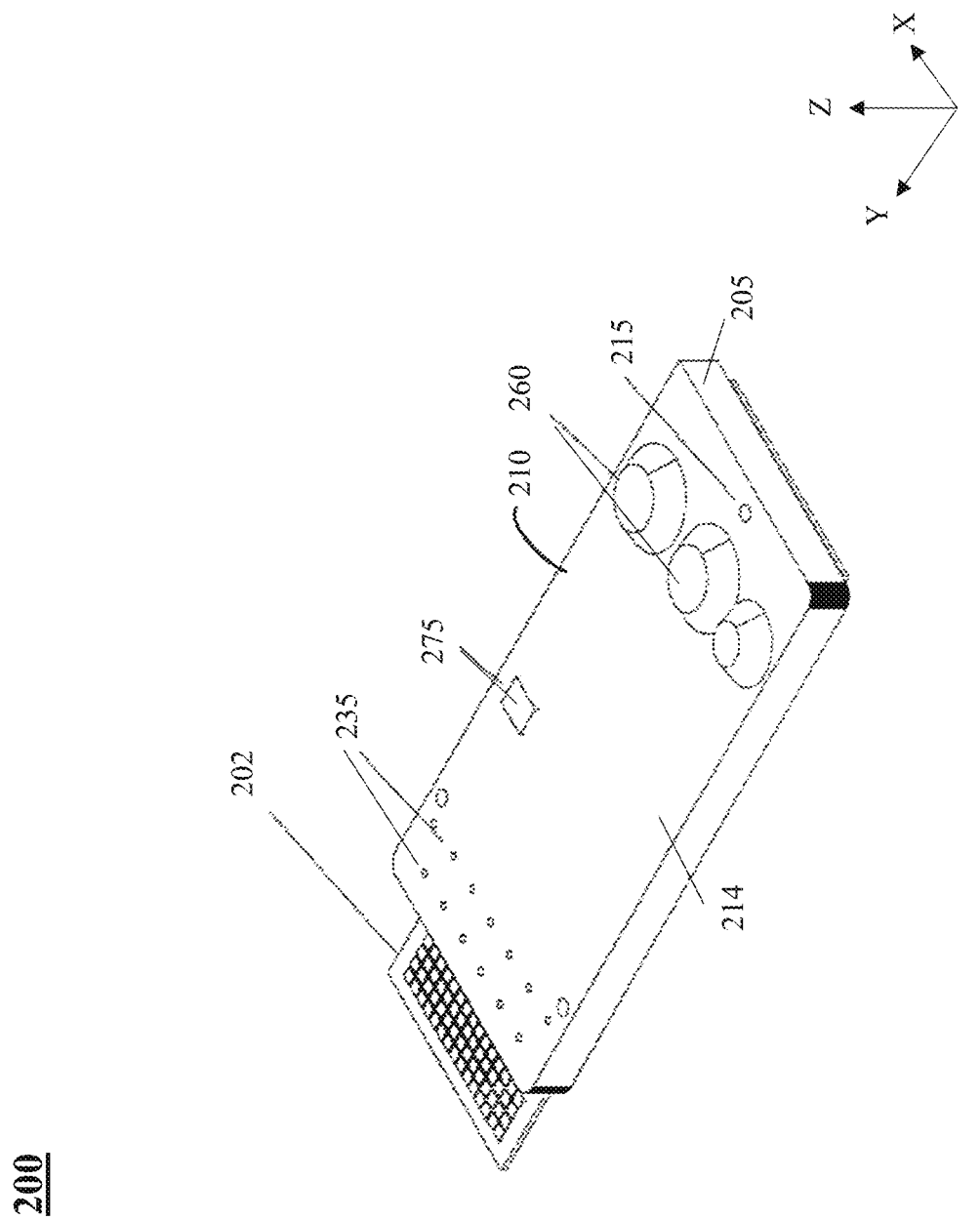
FIG. 2A is a perspective view of an exemplary cartridge assembly used in the system, in accordance with an embodiment of the present disclosure.
Figure 2B:
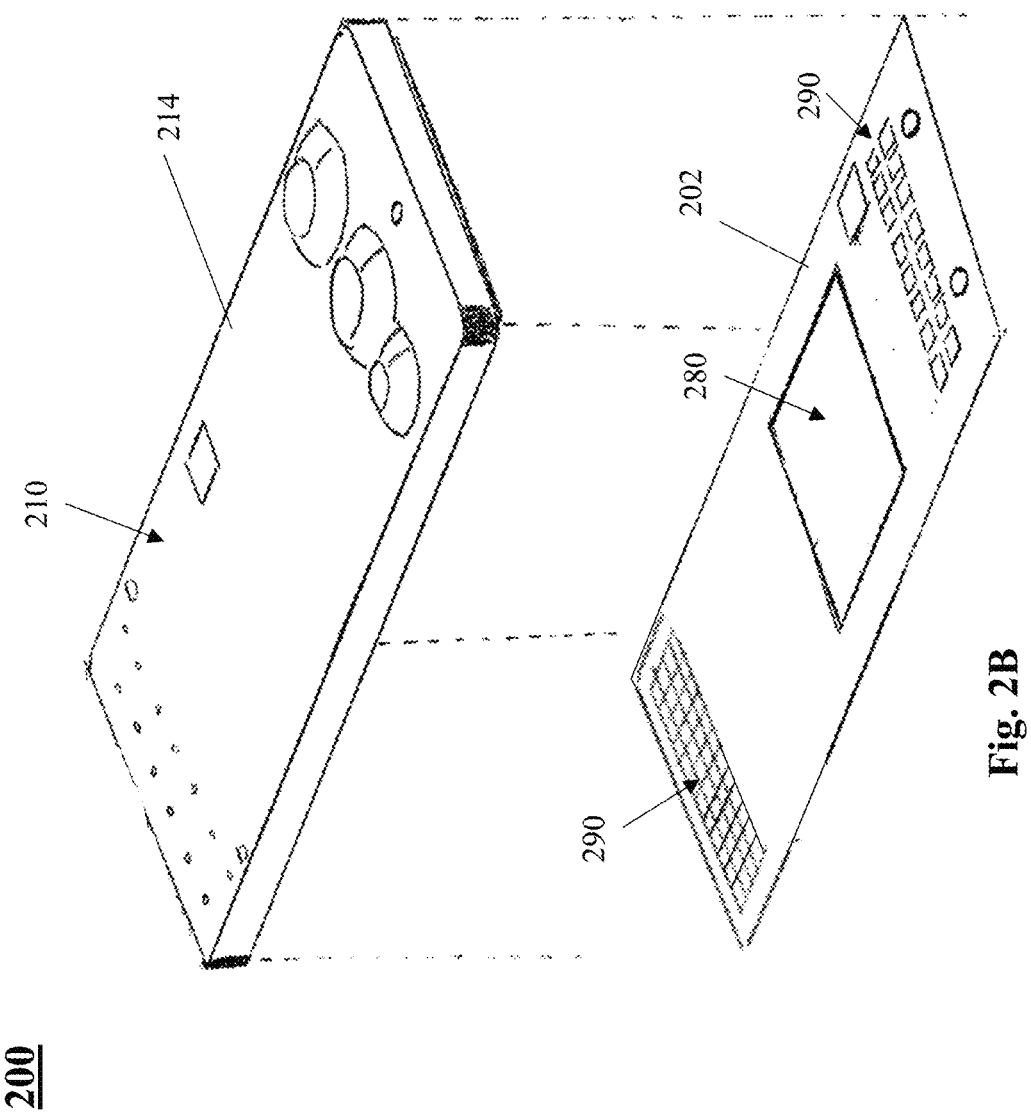
FIG. 2B is an exploded view of the cartridge assembly of FIG. 2A, in accordance with an embodiment herein.
Figure 2C:
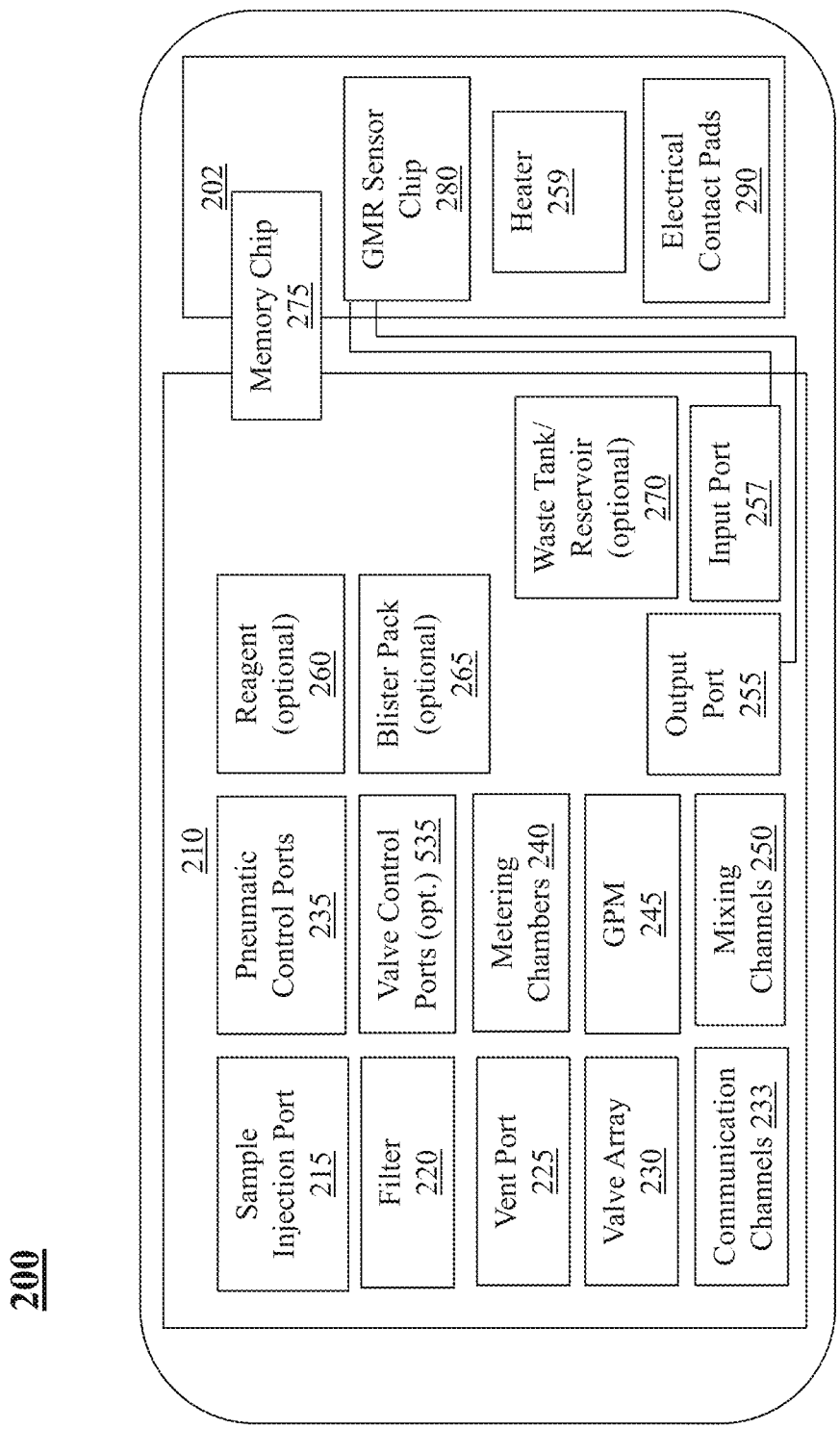
FIG. 2C is a schematic drawing of the cartridge assembly of FIG. 2A, in accordance with an embodiment herein.

As previously noted, cartridge assembly 200 may be designed for insertion into the cartridge reader unit 100, such that a sample (e.g., blood, urine) may be prepared, processed, and analyzed. FIGS. 2A-2C illustrate an exemplary embodiment of a cartridge assembly 200 in accordance with embodiments herein. Some general features associated with the disclosed cartridge assembly 200 are described with reference to these figures. However, as described in greater detail later, several different types of cartridge cards and thus cartridge assemblies may be utilized with the cartridge reader unit 100 and thus provided as part of system 300. In embodiments, the sampling handling system or cartridge assembly 200 may take the form of disposable assemblies for conducting individual tests. That is, as will be further understood by the description herein, depending on a type of sample and/or analytes being tested, a different cartridge card configuration(s) and/or cartridge assembly(ies) may be utilized. FIG. 2A shows a top, angled view of a cartridge assembly 200, in accordance with an embodiment herein. The cartridge assembly 200 includes a sample processing card 210 and a sensing and communication substrate 202 (see also FIG. 2B). Generally, the sample processing card 210 is configured to receive the sample (e.g., via a sample port such as injection port, also described below) and, once inserted into the cartridge reader unit 100, process the sample and direct flow of the sample to produce a prepared sample. Card 210 may also store waste from a sample and/or fluids used for preparing the test sample in an internal waste chamber(s) (not shown in FIG. 2A, but further described below). Memory chip 275 may be read and/or written to and is used to store information relative to the cartridge application, sensor calibration, and sample processing required, for example. In an embodiment, the memory chip 275 is configured to store a pneumatic system protocol that includes steps and settings for selectively applying pressure to the card 210 of the cartridge assembly 200, and thus implementing a method for preparation of sample for delivery to a magnetoresistive or magnetoresistance sensor (e.g., GMR sensor chip 280). The memory chip may be used to mistake-proof each cartridge assembly 200 inserted into the unit 100, as it includes the automation recipe for each assay. The memory chip 275 also contain traceability to the manufacturing of each card 210 and/or cartridge assembly 200. The sensing and communication substrate 202 may be configured to establish and maintain communication with the cartridge reader unit 100, as well as receive, process, and sense features of the prepared sample. The substrate 202 establishes communication with a controller in the cartridge reader unit 100 such that analyte(s) may be detected in a prepared sample. The sample processing card 210 and the sensing and communication substrate 202 (see, e.g., FIG. 2B) are assembled or combined together to form the cartridge assembly 200. In an embodiment, adhesive material (see, e.g., FIG. 2D) may optionally be used to adhere the card 210 and substrate 202 to one another. In an embodiment, the substrate 202 may be a laminated layer applied to the sample processing card 210. In one embodiment, the substrate 202 may be designed as a flexible circuit that is laminated to sample processing card 210. In another embodiment, the sample processing card 210 may be fabricated from a ceramic material, with the circuit, sensor (sensor chip 280) and fluid channels integrated thereon. Alternatively, the card 210 and substrate 202 may be mechanically aligned and connected together. In one embodiment, a portion of the substrate 202 may extend from an edge or an end of the card 210, such as shown in FIG. 2A. In another embodiment, such as shown in FIG. 2B, the substrate 202 may be aligned and/or sized such that it has similar or smaller edges than the card 210.

Figure 3:
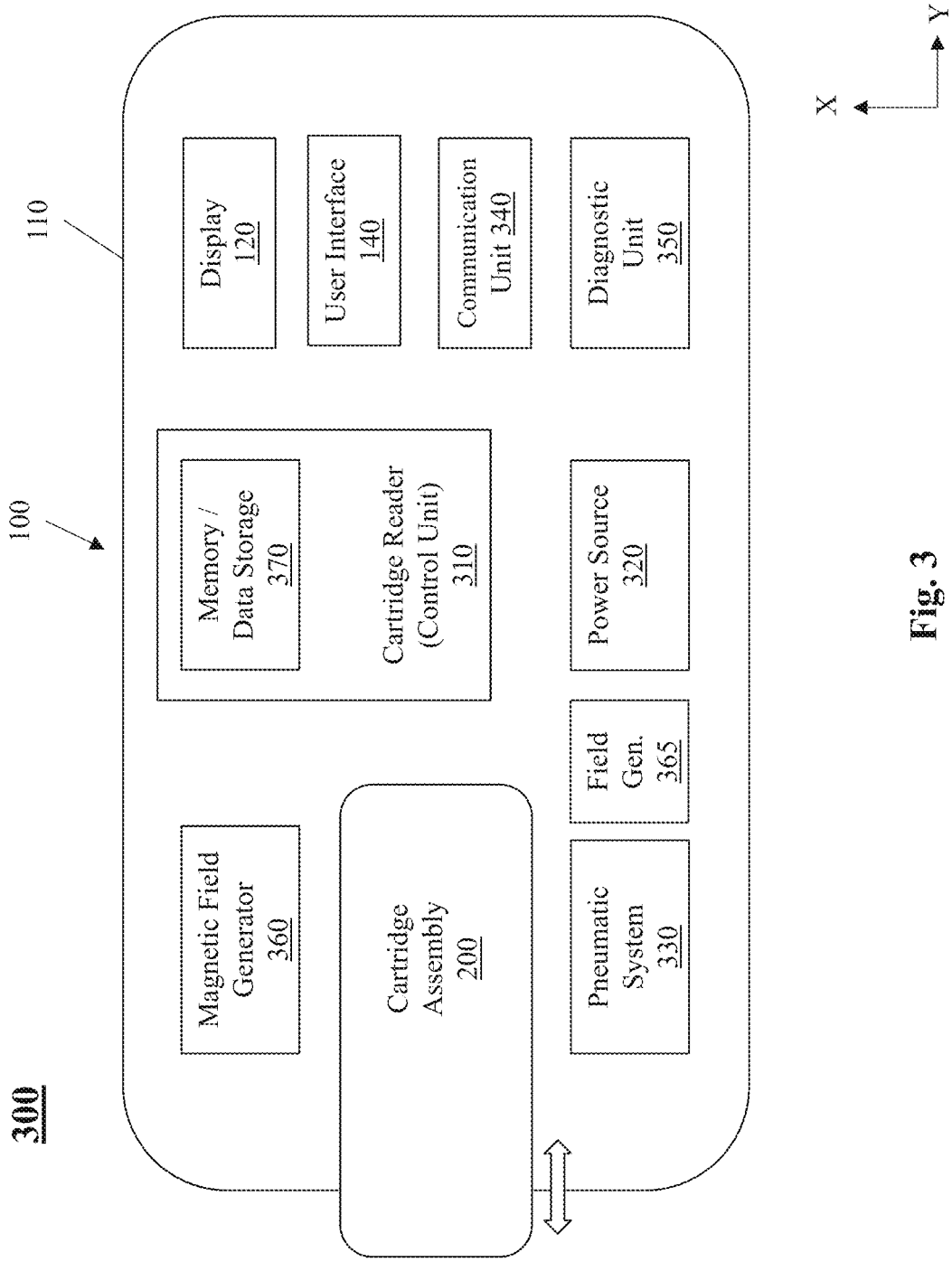
FIG. 3 is a schematic diagram of the system in accordance with an embodiment of the present disclosure.

FIG. 2C schematically illustrates features of the cartridge assembly 200, in accordance with an embodiment. As shown, some of the features may be provided on the sample processing card 210, while other may be associated with the substrate 202. Generally, to receive a test sample (e.g., blood, urine) (within a body of the card), the cartridge assembly 200 includes a sample injection port 215, which may be provided on a top of the card 210. Also optionally provided as part of the card 210 are filter 220 (also referred to herein as a filtration membrane), vent port 225, valve array 230 (or valve array zone 230), and pneumatic control ports 235. Communication channels 233 are provided within the card 210 to fluidly connect such features of the card 210. Pneumatic control ports 235 are part of a pneumatic interface on the cartridge assembly 200 for selectively applying pressurized fluid (air) to the communication channels 233 of the card, for directing flow of fluids (air, liquids, test sample, etc.) therein and/or valve array 230. Optionally, the card 210 may include distinct valve control ports 535 connected to designated communication channels 233 for controlling the valves in the valve array 230. The card 210 may also have one or more metering chambers 240, gas permeable membranes 245, and mixing channels 250 that are fluidly connected via communication channels 233. Metering chamber(s) are designed to receive at least the test sample (either directly or filtered) therein via communication channels 233. Such features are discussed in general detail below with reference to FIGS. 18-26, showing an exemplary embodiment of features of a sample processing card that may be used as part of a cartridge assembly 200. Alternative embodiments are shown International Patent Application No. PCT/US2019/043753, entitled "SYSTEM AND METHOD FOR SAMPLE PREPARATION IN GMR-BASED DETECTION OF BIOMARKERS" and filed on the same day, which is hereby incorporated by reference herein in its entirety. Generally, a sample may be injected into the cartridge assembly 200 through port 215 and processed by means of filtering with filter (e.g., filter 220), metering in metering chamber(s) 240, mixing in mixing channel(s) 250, heating and/or cooling (optional), and directing and changing the flow rate via communication channels 233, pneumatic control ports 235, and valve array 230. For example, flow of the fluid may be controlled using internal micro fluidic channels (also generally referred to as communication channels 233 throughout this disclosure) and valves via a connection of a pneumatic system (e.g., system 330 in the cartridge reader unit 100, as shown in FIG. 3, as well as FIGS. 5-16) and a pneumatic interface e.g., on the card 210 that has pneumatic control ports 235 or a similar connection section. Optional heating of the test sample and/or mixing materials/fluids within the card 210 may be implemented, in accordance with an embodiment, via a heater 259 which may be in the form of a wire trace provided on a top side of a PCB/substrate 202 with a thermistor. Optional cooling of the test sample and/or mixing materials/fluids within the card 210 may be implemented, in accordance with an embodiment, via a TEC module integrated in the cartridge assembly 200 (e.g., on the substrate 202), or, in another embodiment, via a module integrated inside of the cartridge reader unit 100. For example, if the cooling module is provided in the unit 100, it may be pressed against the cartridge assembly 200 should cooling be required. Processing may also optionally include introduction of reagents via optional reagent sections 260 (and/or blister packs) on the card 210 and/or via reagent cartridges in the housing 110 the cartridge reader unit 100. Reagents may be released or mixed as required by the process for that sample and the cartridge assembly 200 being analyzed. Further, optional blister packs 265 may be provided on the card 210 to introduce materials such as reagents, eluants, wash buffers, magnetic nano particles, bead solution, or other buffers to the sample via communication channels 233 during processing. One or more internal waste chambers (also referred to herein as waste tanks for waste reservoirs) 270 may also be optionally provided on the card 210 to store waste from the sample and reagents. An output port 255—also referred to as a sensor delivery port, or input port to the sensor—is provided to output a prepared sample from the card 210 to a GMR sensor chip 280, as discussed below, for detecting analytes in the test sample. The output port 255 may be fluidly connected to a metering chamber for delivering the test sample and one or more mixing materials to the sensor. Accordingly, the sensor may be configured to receive the test sample and the one or more mixing materials via the at least one output port 255. In embodiments, an input port 257—also referred to as a waste delivery port, or output port from the sensor—is provided to output any fluid or sample from the GMR sensor chip 280 to a waste chamber 270. Waste chamber(s) 270 may be fluidly connected to other features of the card 210 (including, for example, metering chamber(s) 240, an input port 257, or both) via communication channels 233.

The cartridge assembly 200 has the ability to store, read, and/or write data on a memory chip 275, which may be associated with the card 210 or the substrate 202. As noted previously, the memory chip 275 may be used to store information related and/or relative to the cartridge application, sensor calibration, and required sample processing (within the sample processing card), as well as receive additional information based on a prepared and processed sample. The memory chip 275 may be positioned on the sample processing card 210 or on the substrate 200.

As previously noted, a magnetoresistive sensor may be utilized, in accordance with embodiments herein, to determine analytes (such as biomarkers) within a test sample using the herein disclosed system. While the description and Figures note use of a particular type of magnetoresistance sensor, i.e., a giant magnetoresistance (GMR) sensor, it should be understood that this disclosure is not limited to a GMR sensor platform. In accordance with some embodiments, the sensor may be an anisotropic magnetoresistive (AMR) sensor and/or magnetic tunnel junction (MTJ) sensors, for example. In embodiments, other types of magnetoresistive sensor technologies may be utilized. Nonetheless, for explanatory purposes only, the description and Figures reference use of a GMR sensor as a magnetoresistive sensor.

The substrate 202 of cartridge assembly 200 may be or include an electronic interface and/or a circuit interface such as a PCB (printed circuit board) that may have a giant magnetoresistance (GMR) sensor chip 280 and electrical contact pads 290 (or electrical contact portions) associated therewith. Other components may also be provided on the substrate 202. The GMR sensor chip 280 is attached at least to the substrate 202, in accordance with an embodiment. The GMR sensor chip 280 may be placed on and attached to the substrate 202 using adhesive, for example. In an embodiment, a liquid adhesive or a tape adhesive may be used between the GMR sensor 280 and the PCB substrate 202. Such a design may require a bond to the PCB at the bottom and a bond to the processing card at the top, for example. Alternatively, other approaches for attaching the GMR sensor chip 280 to the substrate 202 include, but are not limited to: friction fitting the GMR sensor to the PCB, and connecting a top of the GMR sensor chip 280 directly to the sample processing card 210 (e.g., in particular when the substrate 202 is provided in the form of a flexible circuit that is laminated (to the back) of sample processing card 210. The GMR sensor chip 280 may be designed to receive a prepared sample from the output port 255 of the sample processing card 210. Accordingly, placement of the GMR sensor chip 280 on the substrate may be changed or altered based on a position of the output port 255 on card 210 (thus, the illustration shown in FIG. 2B is not intended to be limiting)—or vice versa. In an embodiment, the GMR sensor chip 280 is positioned on a first side of the substrate 202 (e.g., a top side that faces an underside of the card 210, as shown in FIG. 2B), e.g., so as to receive the prepared sample from an output port that outputs on an underside of the card 210, and the contact pads 290 are positioned on an opposite, second side of the substrate (e.g., on a bottom side or underside of the substrate 202, such that the contact pads 290 are exposed on a bottom side of the cartridge assembly 200 when fully assembled for insertion into the cartridge reader unit 100). The GMR sensor chip 280 may include its own associated contact pads (e.g., metal strips or pins) that are electrically connected via electronic connections on the PCB/substrate 202 to the electrical contact pads 290 provided on the underside thereof. Accordingly, when the cartridge assembly 200 is inserted into the cartridge reader 100, the electrical contact pads 290 are configured to act as an electronic interface and establish an electrical connection and thus electrically connect with electronics (e.g., cartridge reader 310) in the cartridge reader unit 100. Thus, any sensors in the sensor chip 280 are connected to the electronics in the cartridge reader unit 100 through the electrical contact pads 290 and contact pads of the GMR sensor chip 280.

Figure 2D:
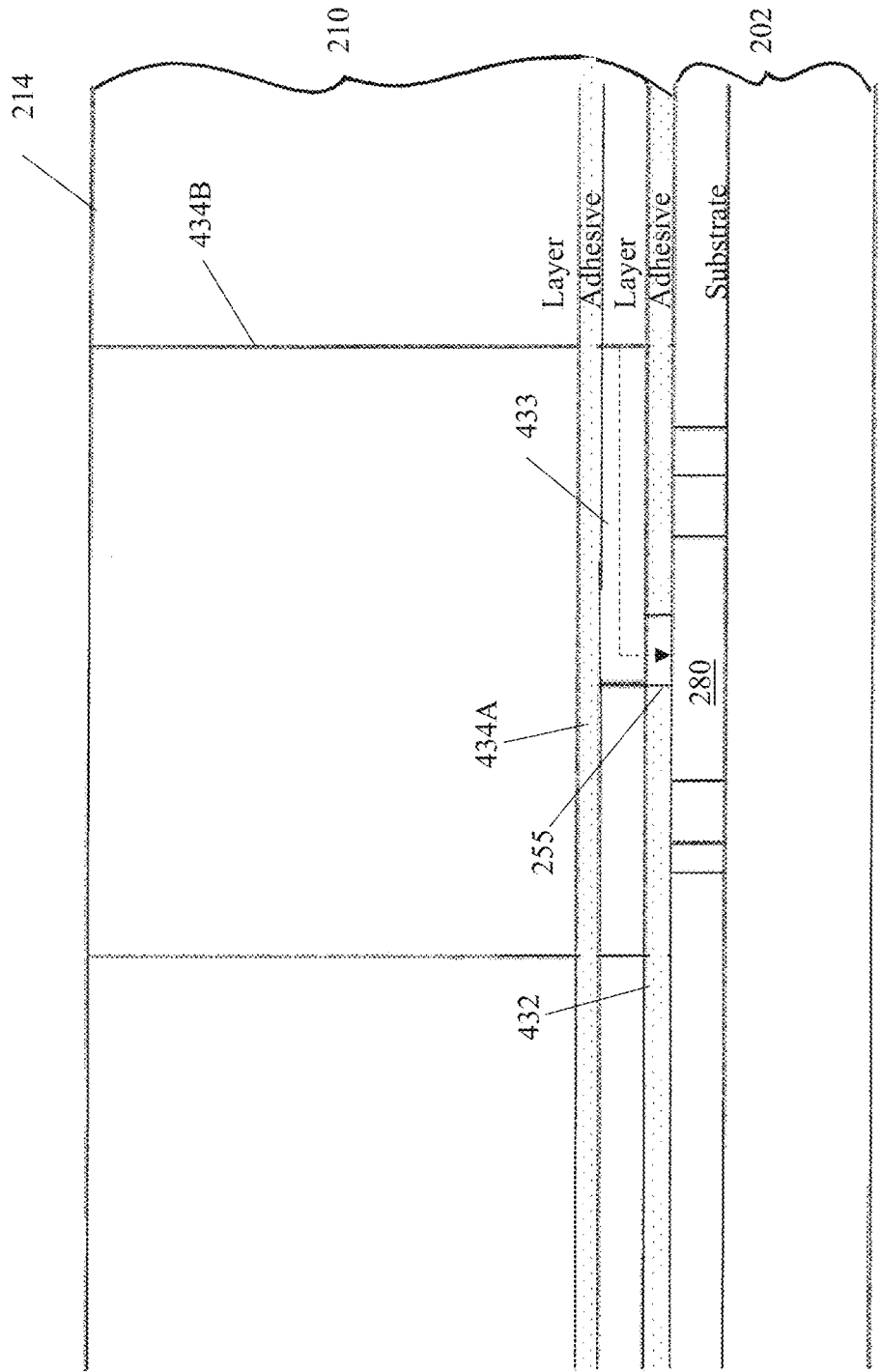
FIG. 2D shows a cross section of the cartridge assembly of FIG. 2A, illustrating a connection interface between a sample processing card and a sensing and communication substrate thereof.
Figure 2E:
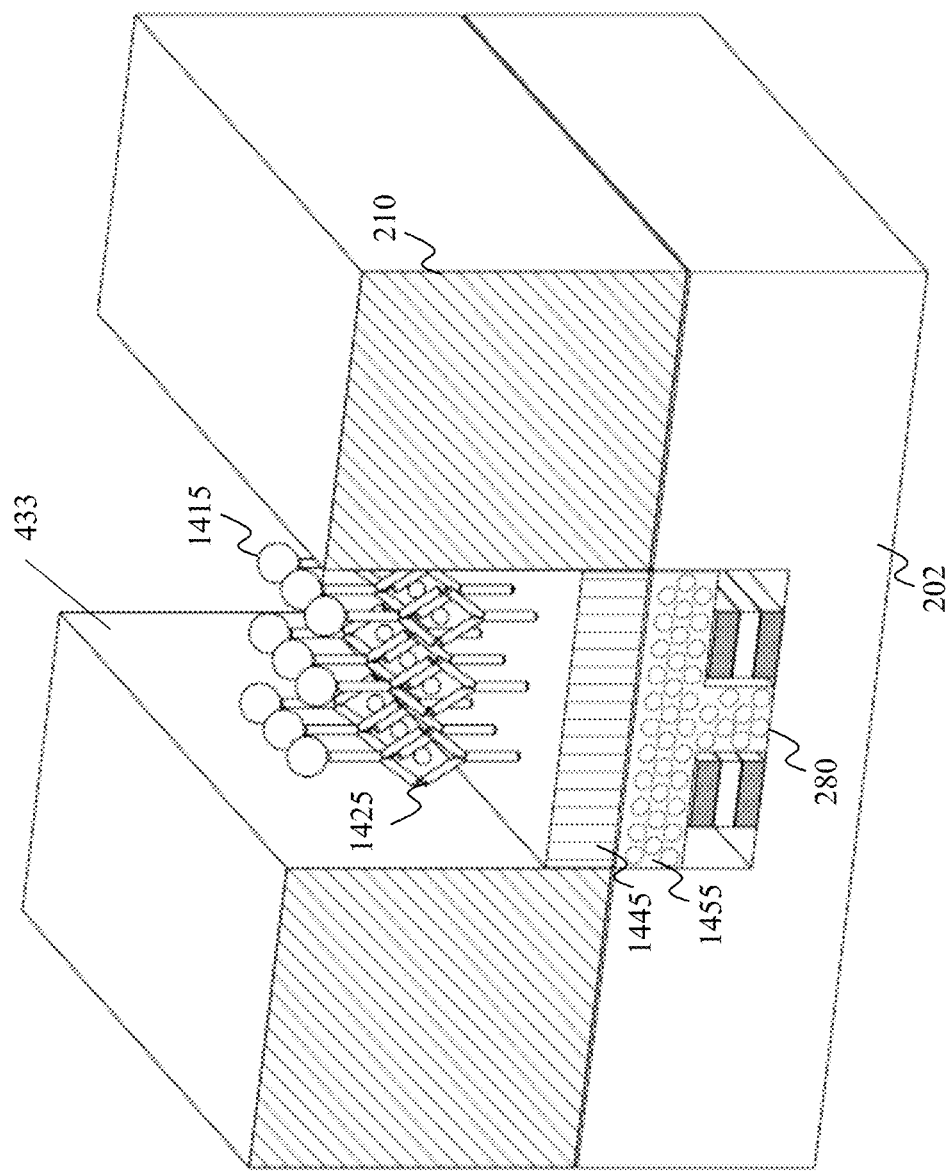
FIG. 2E shows a perspective of the cross section of FIG. 2D, showing more detail of a channel at the location of a GMR sensor, in accordance with an embodiment herein.

FIGS. 2D and 2E show views of an exemplary cross section of a mating or connection interface of card 210 and substrate 202. More specifically, FIG. 2D illustrates an interface, in accordance with one embodiment, between an output port 255 on the card 210 and GMR sensor chip 280 of the substrate 202. For example, shown is a PCB substrate 202 positioned below and adjacent to a card 210 according to any of the herein disclosed embodiments. The substrate 202 may be attached to bottom surface of the card 210. The card 210 has a channel feature, labeled here as microfluidic channel 433 (which is one of many communication channels within the card 210), in at least one layer thereof, designed to direct a test sample that is processed within the card 210 to an output port 255 directed to GMR sensor 280. Optionally, adhesive material may be provided between layers of the card 210, e.g., adhesive 434A may be provided between a layer in the card that has reagent ports 434B and a layer with the channel 433. The substrate 202 includes a GMR sensor chip 280 that is positioned adjacent to the channel 433 and output port 255 of the card 210. FIG. 2E shows a schematic drawing related to analyte detection using a card 210 with said one or more microfluidic channels 433 and GMR sensor chip 280 associated with a silicon wafer of a PCB substrate 202. The analyte detection is made possible through micro fluidics, surface chemistry, sample targets, nano magnetic beads, magnetic field and giant magneto resistance (GMR) sensor chip 280. Micro fluidic channel(s) 433 (i.e., communication channels) in the card 210 may assist in directing flow of a separated test sample and nano magnetic beads from a magnetic bead-bound entity 1415 for processing, for example. Magnetic bead-bound entity 1415 may be configured to interact with biomolecule 1425 (also referred to as a target) or an analyte of interest, such as in a sandwich complex of antibody-analyte-magnetic bead-bound antibody. Sample targets are the items to be detected and measured. Nano magnetic beads 1415 bond to sample targets 1425. Optionally, an insulating material 1445, 1455 may be provided between over the sensor(s) 280. For example, in the embodiment shown in FIG. 2E, below biosurface 1445 is a further insulating layer 1455. Insulating layer 1455 may be in direct contact with GMR sensor(s) 280 and may comprise, for example, a metal oxide layer. Biosurface layer 1445 may be in direct contact with insulating layer 1455, in accordance with one embodiment. Substrate 202 may serve as a scaffold for each component above it, e.g., the GMR sensors 280, insulating layer 1455, and/or biosurface layer 1445. In some embodiments, substrate 202 may be made from a silicon wafer or a laminated flex layer.

Figure 2F:
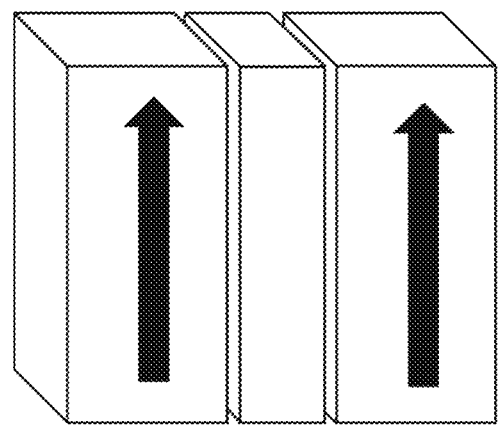
FIG. 2F schematically illustrates a basic structure and principle of GMR sensors.
Figure 2F:
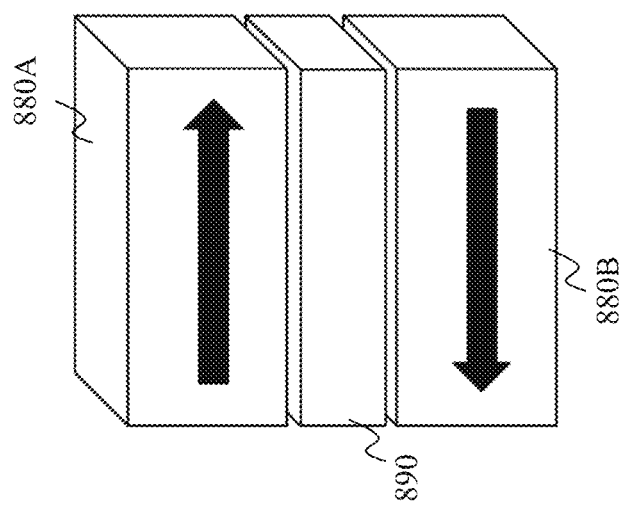

Magnetic field (from a magnetic field generator 365 that is different than magnetic field generator 360, described below with reference to FIG. 3) may be used to excite the nano magnetic particles located near sensors. FIG. 2F shows a schematic example of antiparallel and parallel magnetization, for example. Similar principles may be applied here at the GMR sensor chip 280. Specifically, as shown in FIG. 2F, the GMR sensor may be designed to include of a metallic multi-layered structure with a non-magnetic conductive interlayer 890 sandwiched between two magnetic layers 880A and 880B. In an embodiment, the non-magnetic conductive interlayer 890 may be a thin copper film. In an embodiment, GMR sensor chip 280 is constructed using a metallic structure with several nanometers non-magnetic conducting thin film (e.g., copper) sandwiched between two ferromagnetic layers (880A and 880B in FIG. 2F) changes depending on the relative magnetization direction of the ferromagnetic layers. The electrical resistance of the metallic multi-layered structure changes depending on magnetization direction of the magnetic layers 880A and 880B. Parallel magnetization (as shown in the right half of FIG. 2F) results in lower resistance, while anti-parallel magnetization (as shown in the left half of FIG. 2F) results in higher resistance. This phenomenon facilitates detection of stray fields from magnetic materials at nanometer scales. The magnetization direction may be controlled by a magnetic field applied externally. As a result, the metallic multi-layered structure displays a change in its electrical resistance as a function of the external magnetic field.

GMR sensors have sensitivities that exceed those of anisotropic magnetoresistance (AMR) or Hall sensors. This characteristic enables detection of stray fields from magnetic materials at nanometer scales. For example, stray fields from magnetic nanoparticles that bound on sensor surface will alter the magnetization in the magnetic layers, and thus change the resistance of the GMR sensor. Accordingly, changes in the number of magnetic nanoparticles bound to the GMR sensor per unit area can be reflected in changes of the resistance value of the GMR sensor.

For such reasons, the sensor utilized in cartridge assembly 200, in accordance with the embodiments described herein, is a GMR sensor chip 280.

Referring now to FIG. 3, an overview of features provided in the system are shown. In particular, some additional features of the cartridge reader unit 100 are schematically shown to further describe how the cartridge reader unit 100 and cartridge assembly 200 are configured to work together to provide the system 300 for detecting analyte(s) in a sample. As depicted, the cartridge assembly 200 may be inserted into the housing 110 of the cartridge reader unit 100. Generally, the housing 110 of the cartridge reader unit 100 may further include or contain a processor or control unit 310, also called a "controller" and/or a "cartridge reader" 310 herethroughout, a power source 320, a pneumatic system 330, a communications unit 340, a (optional) diagnostic unit 350, a magnetic field generator 360, and a memory 370 (or data storage), along with its user interface 140 and/or display 120. Optionally, a reagent opener (e.g., puncture system 533 in FIG. 6), e.g., for opening a reagent source on an inserted cartridge assembly or for introducing reagent into the cartridge assembly (e.g., if the reagent is not contained in the assembly in a particular reagent section), may also be provided as part of the cartridge reader unit 100. Once a cartridge assembly 200 is inserted into the housing 110 of the cartridge reader unit 100, and the electrical and pneumatics system(s) are connected, and the cartridge memory chip 275 may be read from the cartridge assembly 200 (e.g., read by cartridge reader 310/control unit, or PCB assembly, in the unit 100) to determine the pneumatic system protocol that includes steps and settings for selectively applying pressure to the card 210 of the cartridge assembly 200, and thus implementing a method for preparation of sample for delivery to a sensor (e.g., GMR sensor chip 280), and thus the sample placed in the assembly 200 may be prepped, processed, and analyzed. The control unit or cartridge reader 310 may control inputs and outputs required for automation of the process for detecting the analyte(s) in a sample. The cartridge reader 310 may be a real-time controller that is configured to control, among other things, the giant magnetic resistance (GMR) sensor chip 280 and/or memory chip 275 associated with the cartridge assembly 200 and the pneumatic system 330 within the housing 110, as well as the controls from user interface, driving the magnetic field generator 360, and receiving and/or sending signals from/to sensor chip and/or memory associated with the cartridge assembly 200, for example. In an embodiment, the cartridge reader 310 is provided in the form of a PCB (printed circuit board) which may include additional chips, memory, devices, therein. The cartridge reader 310 may be configured to communicate with and/or control an internal memory unit, a system operation initializer, a signal preparing unit, a signal preparing unit, a signal processing unit, and/or data storage (none of which are shown in the Figures), for example. The cartridge reader 310 may also be configured to send and receive signals with respect to the communications unit 340 such that network connectivity and telemetry (e.g., with a cloud server) may be established, and non-volatile recipes may be implemented, for example. Generally, the communications unit 340 allows the cartridge reader unit 100 to transmit and receive data using wireless or wired technology. Power can be supplied to the cartridge reader unit 100 via power source 320 in the form of an internal battery or in the form of a connector that receives power via an external source that is connected thereto (e.g., via a cord and a plug). The pneumatic system 330 is used to process and prepare a sample (e.g., blood, urine) placed into the cartridge assembly 200 by means of moving and directing fluids inside and along the sample processing card 210 (e.g., via pneumatic connection 235, through its channels and connecting to direct elastomeric valves). The pneumatic system 330 may be a system and/or device for moving fluid, which could use, for example, plungers and/or pistons in contact with fluids (further described later below). The magnetic field generator 360 may be an external magnetic coil or other field generating device that is mounted in the unit 100 or integrated in some fashion with one or more of the chips (e.g., sensor chip 280) provided on the cartridge assembly 200 or provided on the circuit board of the cartridge reader unit 100. The magnetic field generator 360 is used to stimulate magnetic nanoparticles near the GMR sensor chip 280 while reading the signal. In accordance with embodiments, a second magnetic field generator 365, which may be a coil or other field generating device, may be provided as part of the cartridge reader unit 100 and in the housing 110. For example, in accordance with an embodiment, the second magnetic field generator 365 may be separate and distinct from magnetic field generator 360. This second magnetic field generator 365 may be configured to generate a non uniform magnetic field such that it may apply such a magnetic field to a part (e.g., top, bottom, sides) of the sample processing card 210 during preparation and processing of a sample, e.g., when moving mixing material(s), such as a buffer and/or magnetic beads from a mixing material source, and test sample within the card. In an embodiment, the second magnetic field generator 365 is provided on an opposite end or side of the cartridge reader unit (e.g., located in a top of the housing 110 of unit 100), i.e. away from the magnetic field generator 360, which is used for GMR sensing. In one embodiment, the second magnetic field generator 365 is provided on an opposite end of the cartridge reader unit as compared to the magnetic field generator 360 (e.g., second magnetic field generator is located in a top of the housing 110 of unit 100 and magnetic field generator 360 is provided at a bottom end of the unit 100 (e.g., near cartridge receiver 130)). In an embodiment, the total magnetic field for sensing biomarkers/analytes includes an applied field from magnetic field generator 360 (either external or integrated with the sensor chip) along with any disturbance from magnetic nanoparticles near the GMR sensor chip 280. The reagent opener is optionally used to introduce reagents during the sample processing and reading of the GMR sensor chip 280 (e.g., if the reagent is not contained in the card in a particular reagent section). As described previously, the user interface 140/display 120 allows an operator to input information, control the process, provide system feedback, and display (via an output display screen, which may be a touch screen) the test results.

Figure 4:
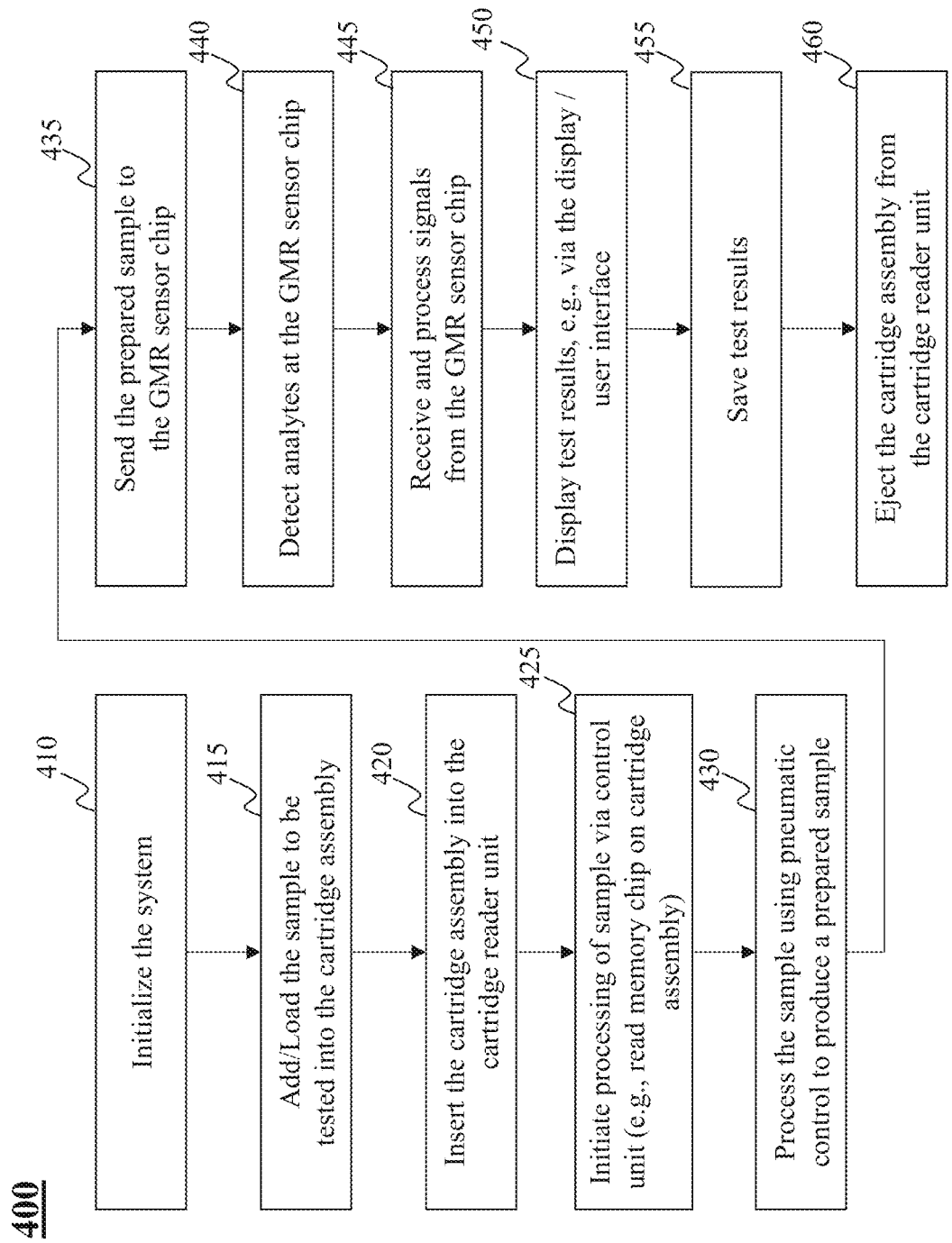
FIG. 4 shows steps of a method for performing analyte detection in a sample when using features of the herein disclosed system of FIG. 3, in accordance with an embodiment.

FIG. 4 shows general steps of a method 400 for performing analyte detection in a sample using the herein disclosed system 300. At step 410, the system is initialized. For example, initialization of the system may include: applying power to the system 300 (including cartridge reader unit 100), determining configuration information for the system, reading computations, determining that features (e.g., magnetic field generator and carrier signals) are online and ready, etc. At step 415, a whole test sample is added or loaded into the cartridge assembly 200 (e.g., sample is injected into the injection port 215, as shown in FIG. 2C). The order of steps 410 and 415 may be changed; i.e., the addition of the whole test sample to the assembly 200 may be before or after the system is initialized. At step 420, the cartridge assembly 200 is inserted into the cartridge reader unit 100. Optionally, as part of method 400, user instruction may be input to the cartridge reader unit 100 and/or system 300 via the user interface/display 120. Then, at step 425, the processing of sample is initiated via the control unit 310. This initiation may include, for example, receiving input via an operator or user through the user interface/display 120 and/or a system that is connected to the reader unit 100. In another embodiment, processing may be initiated automatically via insertion of the cartridge assembly 200 into the cartridge reader unit 100 and detecting presence of the cartridge assembly 200 therein (e.g., via electrical connection between electrical contact pads 290 on the assembly 200 with the control unit 310, and automatically reading instructions from memory chip 275). The sample is processed at step 425 using pneumatic control instructions (e.g., obtained from memory chip 275) in order to produce a prepared sample. As generally described above (and further later below), the processing of the sample may be dependent upon the type of sample and/or the type of cartridge assembly 200 inserted into the reader unit 100. In some cases, the processing may include a number of steps, including mixing, introduction of buffers or reagents, etc., before the sample is prepared. Once the sample is prepared, the prepared sample is sent (e.g., through channels in the card 210 and to output port 255, via pneumatic control through pneumatic system 330 and control unit 310) to the GMR sensor chip 280. At step 440, analytes in the prepared sample are detected at the GMR sensor chip 280. Then, at step 445, signals from the GMR sensor chip 280 are received and processed, e.g., via cartridge reader 310 (control unit; which may include one or more processors, for example). Once the signals are processed, test results may be displayed at 450, e.g., via the display 120/user interface. At 455, test results are saved. For example, test results may be saved in a cloud server and/or memory chip 275 on board the cartridge assembly 200. In embodiments, any fluids or sample may be directed from the GMR sensor chip 280 through an input port 257 to waste chamber 270. Thereafter, once all tests are preformed and read by the sensing device/GMR sensor chip 280, the cartridge assembly 200 may be ejected from the cartridge reader unit 100. In accordance with an embodiment, this may be automatically performed, e.g., mechanics within the housing 110 of the cartridge reader unit 100 may push the assembly 200 out of the housing 110, or performed manually (by way of a button or force) by the operator, for example.

In an embodiment, the system 300 described herein may sense analytes as disclosed in International Patent App. No. PCT/US2019/043766, entitled "SYSTEM AND METHOD FOR SENSING ANALYTES IN GMR-BASED DETECTION OF BIOMARKERS" and filed on the same day, which is hereby incorporated by reference herein in its entirety. For example, in an embodiment, the sensing device, or GMR sensor chip 280, may include one or more microfluidic channels and a plurality of sensor pads disposed within the one or more microfluidic channels as disclosed in the PCT/US2019/043766 application. In an embodiment, such a channel may optionally include a plurality of GMR sensors disposed within a channel. GMR sensors may be all identically configured to detect a single analyte, the redundancy allowing for enhanced detection. GMR sensors may also be all configured differently to detect a myriad of analytes or a combination of differently configured sensors with some redundancies. The configuration of the channel is not limiting. Collectively, the GMR sensors in the channel may be designed to provide the output (test results) from the GMR sensor chip 280.

FIGS. 27-30 generally illustrate functional blocks of the cartridge reader 310 (control unit) and a signal processor within the cartridge reader unit 100, and processes associated therewith, that may be utilized and implemented by the cartridge reader unit 100 with regards to an inserted cartridge assembly 200. In an embodiment, the system 300 described herein may process signals at the GMR sensor as disclosed in International Patent App. No. PCT/US2019/043791, entitled "SYSTEM AND METHOD FOR PROCESSING ANALYTE SIGNALS IN GMR-BASED DETECTION OF BIOMARKERS and filed on the same day, which is hereby incorporated by reference herein in its entirety. For example, as noted above, at step 445, signals from the GMR sensor chip 280 are received and processed, e.g., via cartridge reader 310. In an embodiment, cartridge reader 310 is configured to perform the function of processing results from the GMR sensor chip 280 using a sample preparation control part having a memory reader unit and a sample preparation control unit (e.g., used to receive signals indicating that a cartridge assembly 200 has been inserted into the cartridge reader unit 100, read information stored in the memory chip 275, and generate pneumatic control signals and send them to the pneumatic system 330) and a signal processing part adapted to control electrical elements, prepare and collect signals, and process, display, store, and/or relay detection results to external systems, including processing measurements signals to obtain test results of the analyte detection, as described in detail in the PCT/US2019/043791 application. Additional features relating to the cartridge reader 310 and signal processor of the unit 100 are provided in greater detail later in this disclosure.

It should be understood that, with regards to FIGS. 1 and 2A-2F, the features shown are representative schematics of a cartridge reader unit 100 and cartridge assembly 200 that are part of the herein disclosed system 300 for detecting the analyte(s) in a sample. Accordingly, the illustrations are explanatory only and not intended to be limiting.

In particular, the features illustrated in FIG. 2C are exemplary only and not intended to be limiting. The cartridge assembly 200 may include any of the features previously described, in accordance with an embodiment. Further, an exemplary embodiment of one type of cartridge assembly is described below with references to FIGS. 18-26. It should be understood that any features may be added to, or replaced, in the herein disclosed cartridge assemblies and/or cartridges, for use with the reader. In an embodiment, the system 300 described herein may utilize any number or type of cartridge assembly(ies) 200 as disclosed in the above-noted and incorporated International Patent App. No. PCT/US2019/043753.

FIGS. 5-16 show more details of features in cartridge reader unit 100, in accordance with embodiments herein. Again, the cartridge reader unit 100 includes a housing 110. The housing 110 may include any number of parts, e.g., a top and a bottom part, that are connected together. In an embodiment, housing 110 and/or some of its parts (e.g., internal and/or external parts) may be molded, e.g., injection molded. In the example shown in FIGS. 5-8, a top portion of the housing 110 is removed to show features contained with the housing 110. Specifically, these Figures show parts including cartridge reader 310 (control unit), power source (battery) 320, pneumatic system 330, and magnetic field generator 360 relative to a bottom portion of the housing 110. Of course, it should be understood that the placement of the parts of the cartridge reader unit 100 are not intended to be limiting; rather, when top portion and bottom portion of the housing are assembled, they are designed to enclose or contain such features therein (e.g., see FIG. 8 which shown parts of the pneumatic system 330 that may be covered or enclosed by the top portion (not shown, for clarify) of the housing 110.

Figure 5:
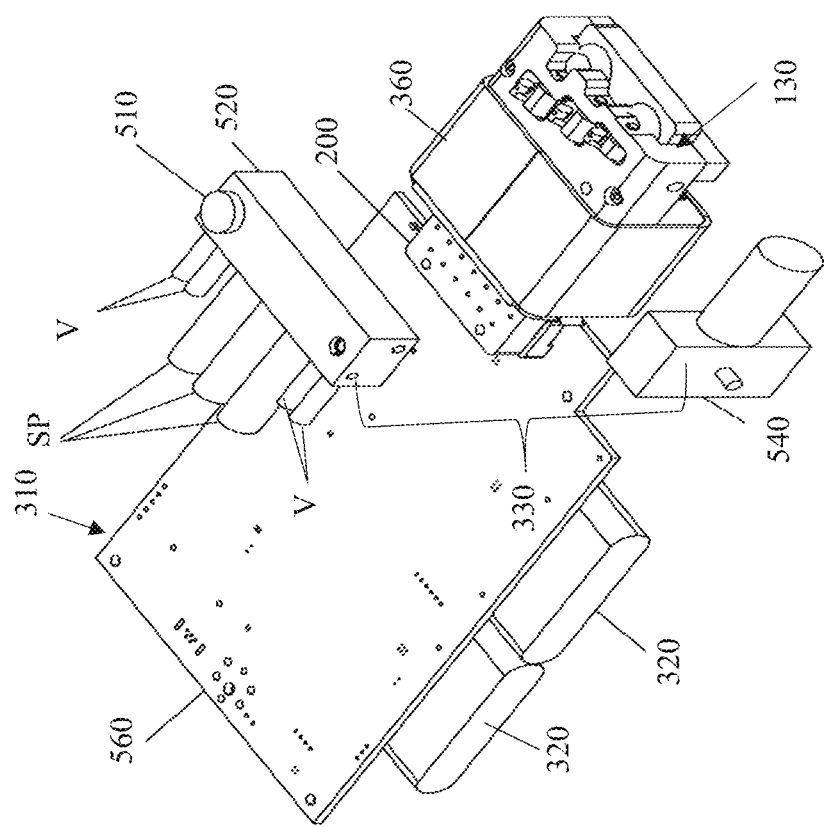
FIG. 5 shows an exemplary internal view of parts associated with the cartridge reader unit in accordance with an embodiment of the present disclosure.
Figure 6:
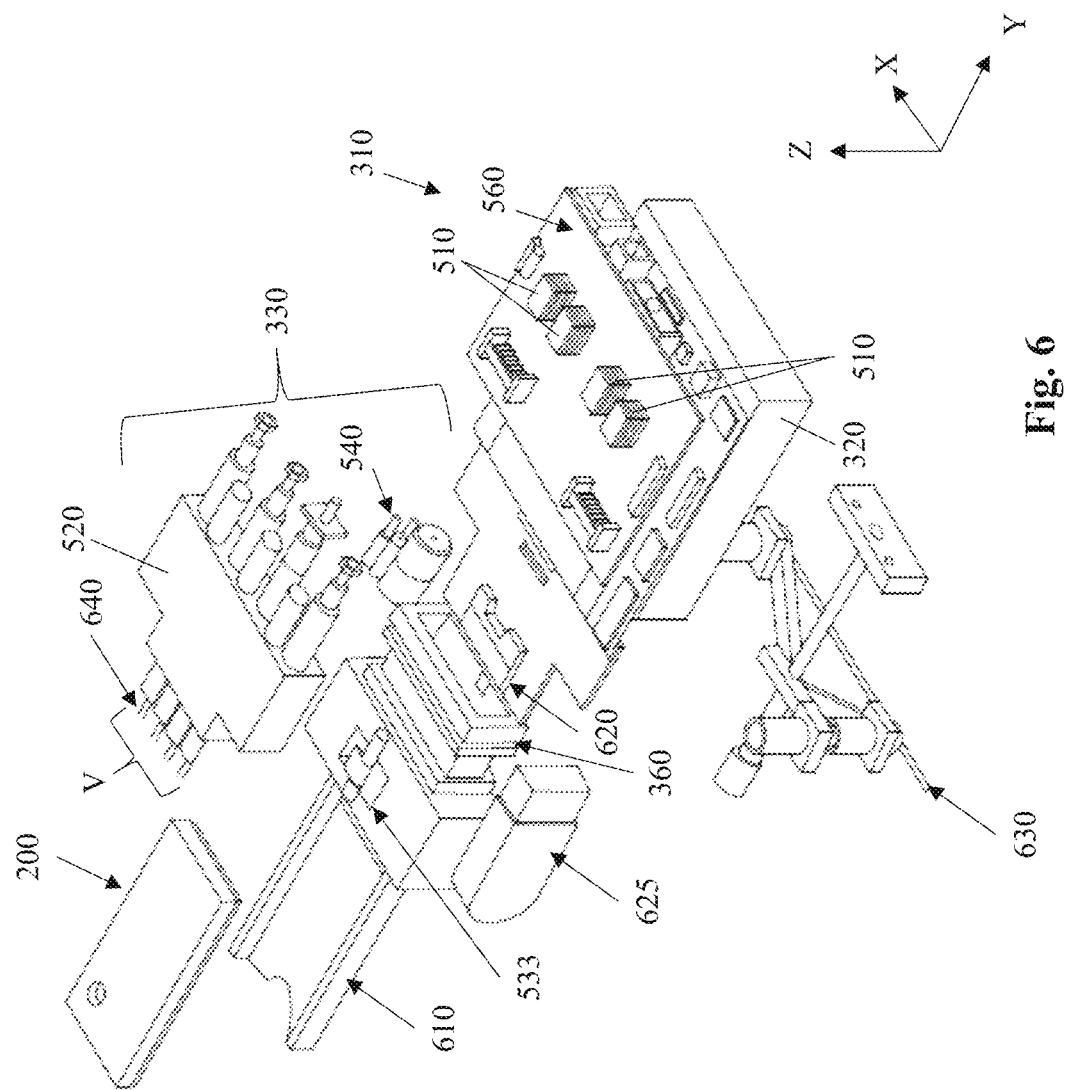
FIG. 6 shows an exploded view of internal parts associated with the cartridge reader unit in accordance with an embodiment of the present disclosure.
Figure 8:
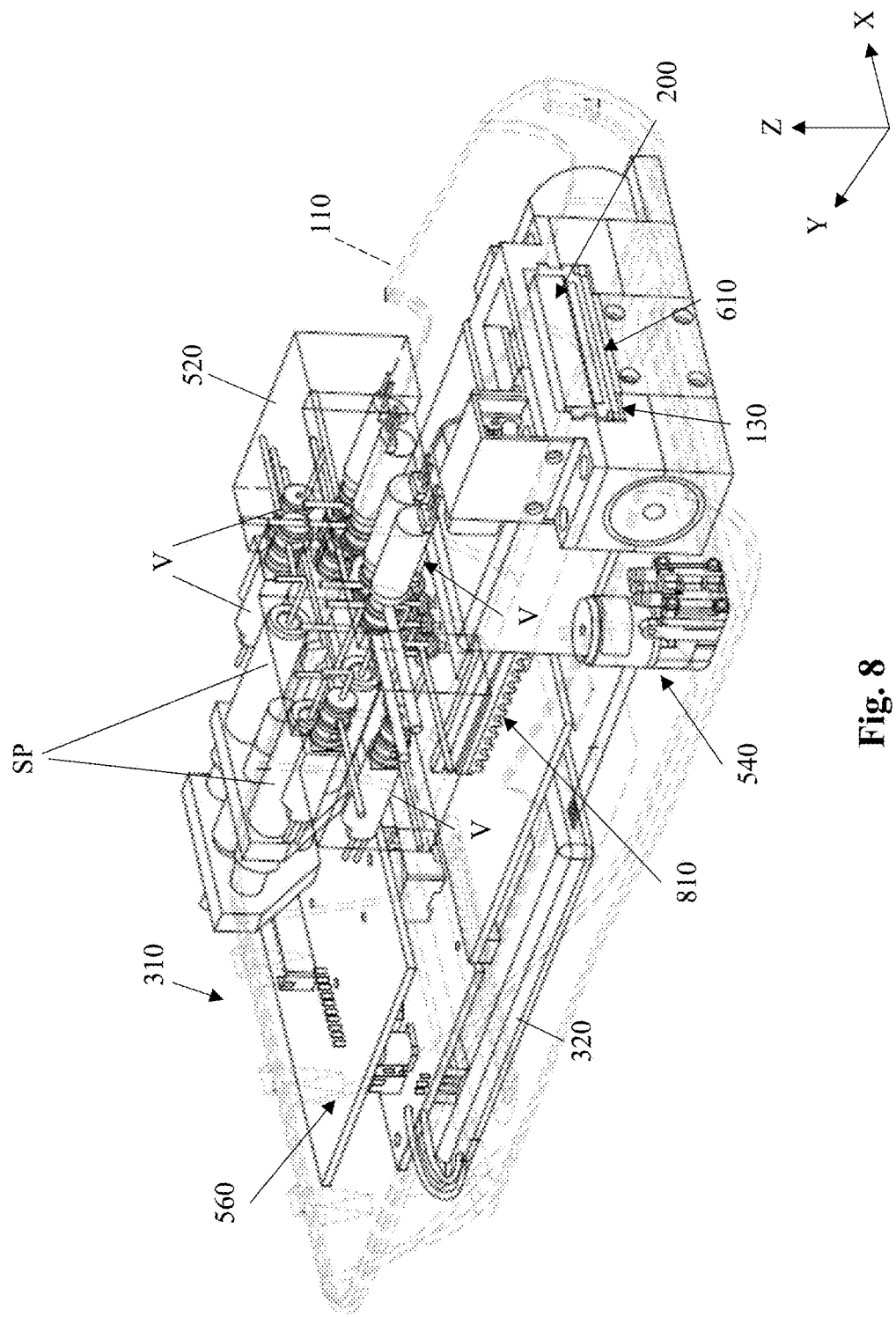
FIG. 8 shows an angled, side view of parts in the cartridge reader unit, with the housing in dashed lines for explanatory purposes only, in accordance with an embodiment of the present disclosure.
Figure 10:
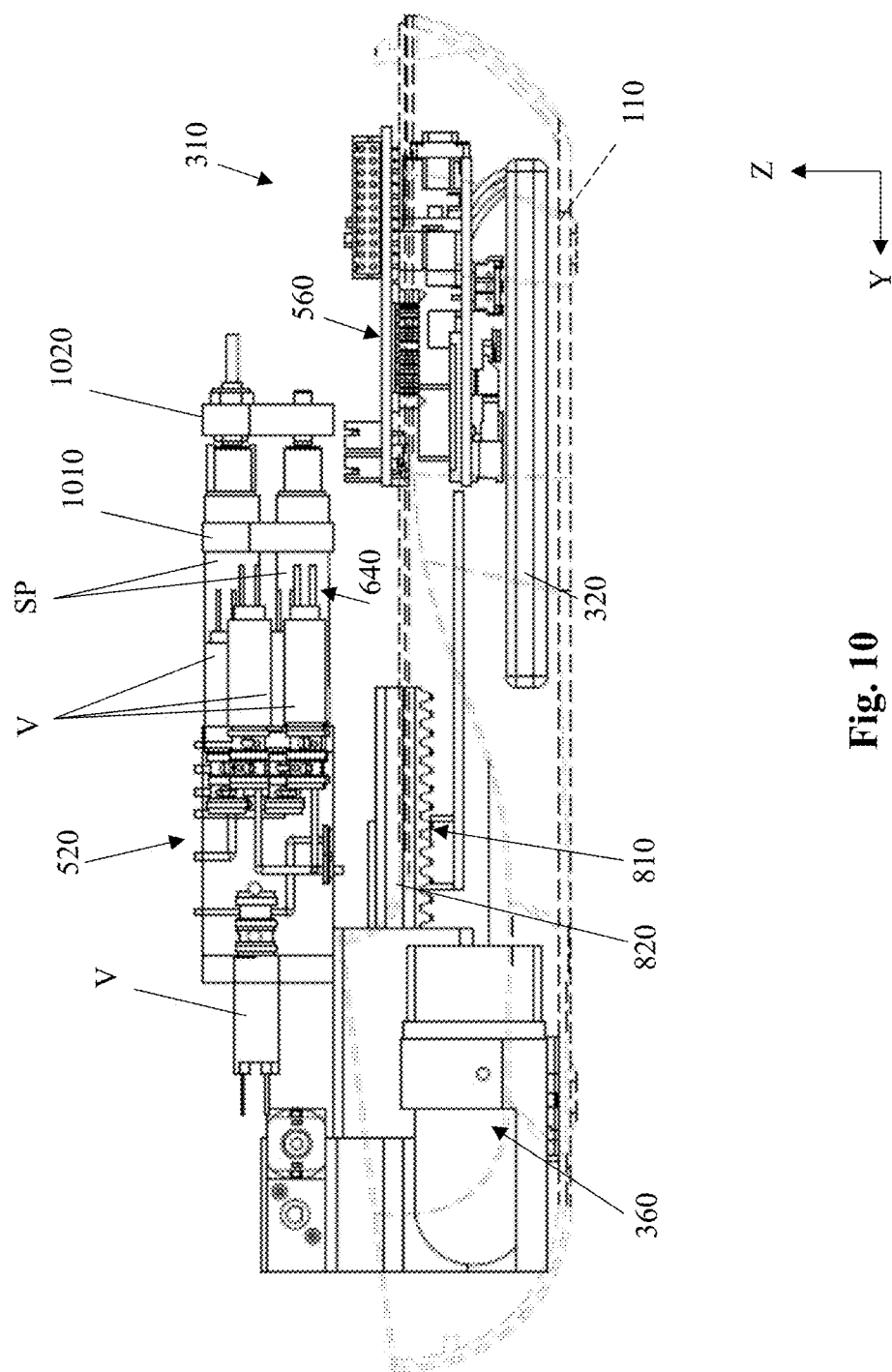
FIG. 10 shows a side view of parts in the cartridge reader unit, with parts of the housing in dashed lines for explanatory purposes only, in accordance with an embodiment of the present disclosure.

FIGS. 5, 6 and 8 show cartridge assembly 200 in place within the cartridge reader unit 100. Cartridge tray 610 is configured to support cartridge assembly 200 when the cartridge assembly is inserted into the cartridge reader unit 100. Specifically, the cartridge assembly 200 may be provided on a tray 610 that is configured to receive cartridge assembly 200 therein. As shown in FIGS. 6, 8, and 10, tray 610 may include a body or undercarriage 820 with a receiving surface that receives the cartridge assembly 200 thereon or therein, in accordance with one embodiment. To move the undercarriage 820, racks of teeth 810 (see FIGS. 8, 10, showing one side (left) of the tray 610) may be connected to each side thereof which are configured to engage corresponding internal gears (not shown) mounted in the housing 110 on either side of the cartridge receiver 130. Accordingly, as the internal gears are rotated, teeth on the internal gears may engage openings between teeth 810, and thus move the racks and undercarriage 820, thereby allowing relative movement of tray 610 to the housing 110, e.g., out of and into an opening 130 therein.

In an embodiment, a clamp system 630 may be provided in housing 110. This clamp system 630 may be designed, for example, to move cartridge tray 610 into and out of housing 110. Additionally and/or alternatively, in an embodiment, the clamp system 630 may be configured to move the cartridge assembly 200 and/or tray 610 vertically, horizontally, or diagonally to align the cartridge assembly 200 for pneumatic and electrical connection with the cartridge reader 310 in the unit 100. The clamp system 630 may be configured to apply force above and/or below the cartridge assembly 200 to ensure the pneumatic and electrical connections. The clamp system 630 may include, in one embodiment, a rack and pinion mechanism that is configured to be driven (e.g., by a motor, such as a stepper motor, e.g., motor 625) to thereby move tray 610 into and out of housing 110. Of course, this is not intended to be limiting, but merely an example of a mechanism that may assist tray 610 in its movement. In an embodiment, the motor 625 may control the pneumatic connection and/or a spring pin connection (connected to 630) to the cartridge assembly 200. As will be described later, the clamp system 630 may work in cooperation with other features provided in the cartridge reader unit 100, e.g., manifold 520 and POGO array 620, to make and ensure proper pneumatics and electrical connections between the cartridge assembly 200 and the unit 100. Further, in an embodiment, motor 625 may be configured to the cartridge assembly position with respect to the housing 110 and/or cartridge receiver 130, such as an ejection from the unit 100.

When cartridge assembly 200 is placed on the tray 610, then inserted or moved into cartridge receiver 130, and thus into the housing 110, the cartridge assembly 200 is moved into alignment with at least cartridge reader 310 and parts of pneumatic system 330. Clamp system 630 may assist in this alignment and connection. In accordance with an embodiment, a stop member is provided in the housing 110 to stop movement of and optionally lock the tray 610 and/or clamp system 630 within the housing 110.

In an embodiment, the cartridge reader 310 is provided in the form of a printed circuit board (PCB) assembly 560. Specifically, at least the electrical contact pads 290 and pneumatic control ports 235 of the cartridge assembly 200 may be aligned with parts of (or electrically attached to) PCB assembly 560 and parts of pneumatic system 330, respectively, when the cartridge assembly 200 is within the unit 100, to establish electrical connection between the control unit and the electronic interface of the assembly 200, thus electrically mating the cartridge reader unit with the electronic interface. In an embodiment, a POGO pin array 620, schematically depicted in FIG. 6, or spring pins are provided in the housing 110 for establishing the electrical connection with the inserted cartridge assembly 200; more specifically, for physically contacting at least a portion of the cartridge assembly to establish the electrical connection. The spring pins are designed to extend generally vertically (in the Z-direction) and upwardly, e.g., towards a cartridge assembly 200. The pins may be an array of vertical spring pins which are mounted inside of a machine block made of insulation material, such as fiberglass, for example. In accordance with one embodiment, the POGO or spring pins are used to make a very low resistance signal between the cartridge assembly and the PCB assembly 560 of the cartridge reader 310. As shown in FIG. 6, for example, the spring pins or POGO pin array 620 may be provided below an opening or cartridge receiver 130 (or, below tray 610) such that when assembly 200 is inserted into the unit 100, the array 620 is positioned relative to electrical contact pads 290 and/or electrical interface of the assembly 200. In an embodiment, the array 620 may align with and engage the electrical contact pads 290 on the bottom of the substrate 220 for establishing communication therewith. In another embodiment, vertical adjustment of the cartridge assembly 200 may be necessary in order to connect the spring pins/array 620 with the electrical interface/electrical contact pads 290 on the assembly 200. In one embodiment, the cartridge assembly 200 may be lowered vertically (e.g., via clamp system 630) and downwardly onto the vertical spring pins, thus making a connection between the array of pads 290 found on the bottom side of the cartridge assembly 200 and the spring pins inside of the reader unit 100. The POGO pin array 620 establishes communication between the cartridge reader 310 (control unit, PCB assembly 560) and cartridge assembly 200. The number of pins associated with the POGO pin array 620 it not meant to be limiting.

PCB assembly 560 may be configured, for example, to include multiple printed circuit boards, in accordance with an embodiment. In one embodiment, three circuit boards may be provided as part of PCB assembly 560. PCB assembly 560 includes a number of chips, such as memory 370 and data storage, and/or transducers 510, and/or other known electronic devices on the one or more circuit boards, configured to implement the functions of the cartridge reader 310 (control unit) and/or implement functions of the system 300 (including display 120, user interface 140, communication unit 340 and/or diagnostic unit 350). For example, in an embodiment, a number of transducers 510 may be provided on one of the PCBs, and/or associated with the pneumatic system 330, for controlling the pneumatic system 330. In another embodiment, electronic devices for memory/data storage 370, communication unit 340, and diagnostic unit 350 may be provided on separate PCBs. Generally, PCB assembly 560 and cartridge reader 310 are configured to implement and perform functions and processes of the cartridge reader unit 100, some of which are described later with respect to FIGS. 27-30 and in the incorporated PCT/US2019/043766 application.

Figure 9:
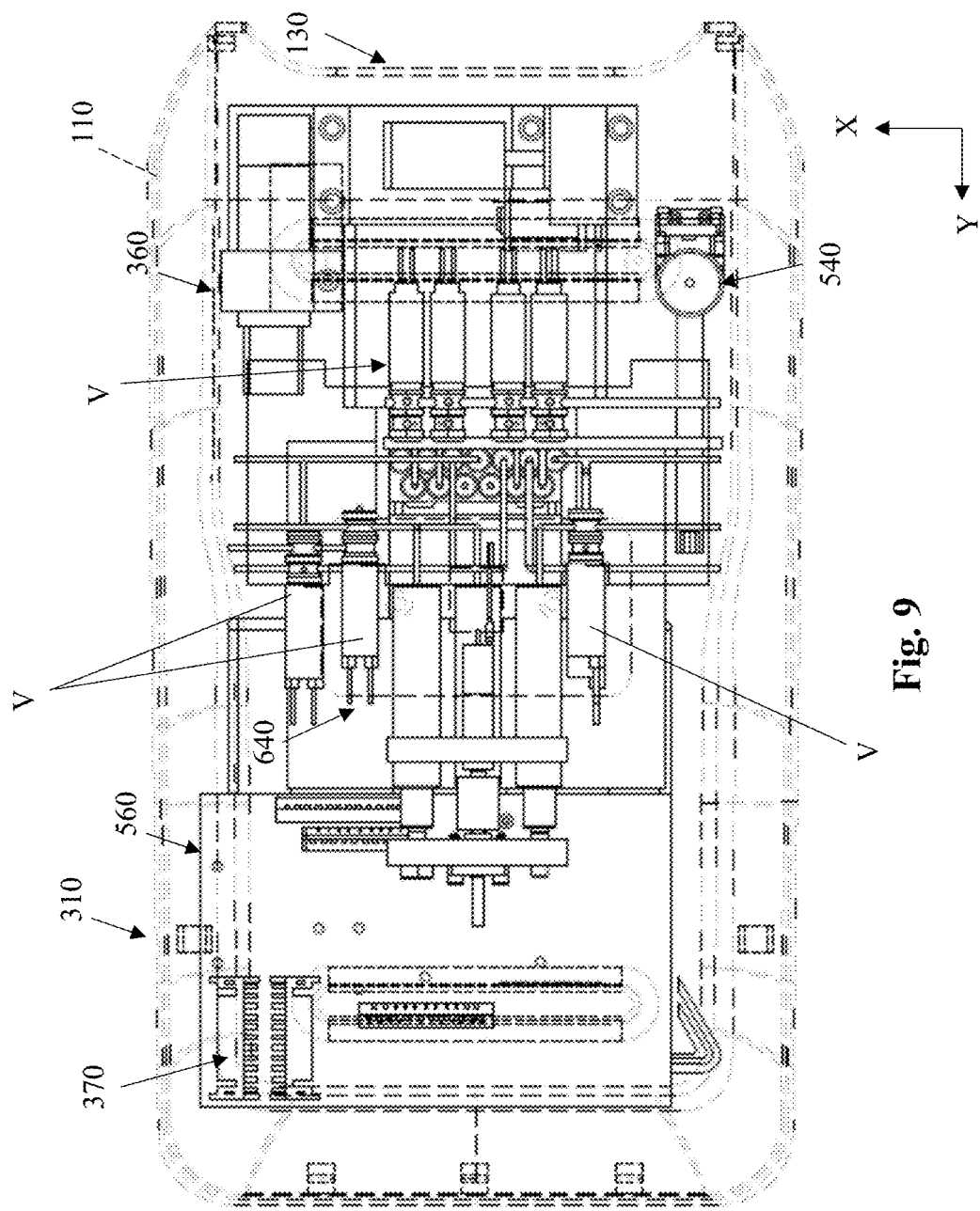
FIG. 9 shows a top view of parts in the cartridge reader unit, with parts of the housing in dashed lines for explanatory purposes only, in accordance with an embodiment of the present disclosure.

Power source 320 is configured to supply power to parts of the cartridge reader unit 100, when activated and/or when a cartridge assembly 200 is mated with the unit 100. For example, power source 320 may supply power to the control unit and PCB assembly 560 of cartridge reader 310, magnetic field generator 360, display 120 and/or user interface 140, and pneumatic system 330 (including, for example, any motors, valves, and/or pumps associated therewith). Power source 320 is shown in FIGS. 9 and 10 as including at least one internally mounted battery pack 320 provided in the housing 110, in accordance with an embodiment herein. Power source 320 may include two or more battery packs, for example, such as shown in FIG. 5. In an embodiment, power source 320 may be mounted underneath PCB assembly 560 and cartridge reader 310 within the housing 110. FIG. 8 shows, for example, placement of an exemplary battery pack 320 under two PCBs of PCB assembly 560. Battery pack 320 may be connected to at least one of the PCBs via wiring, as is known in the art.

Figure 7:
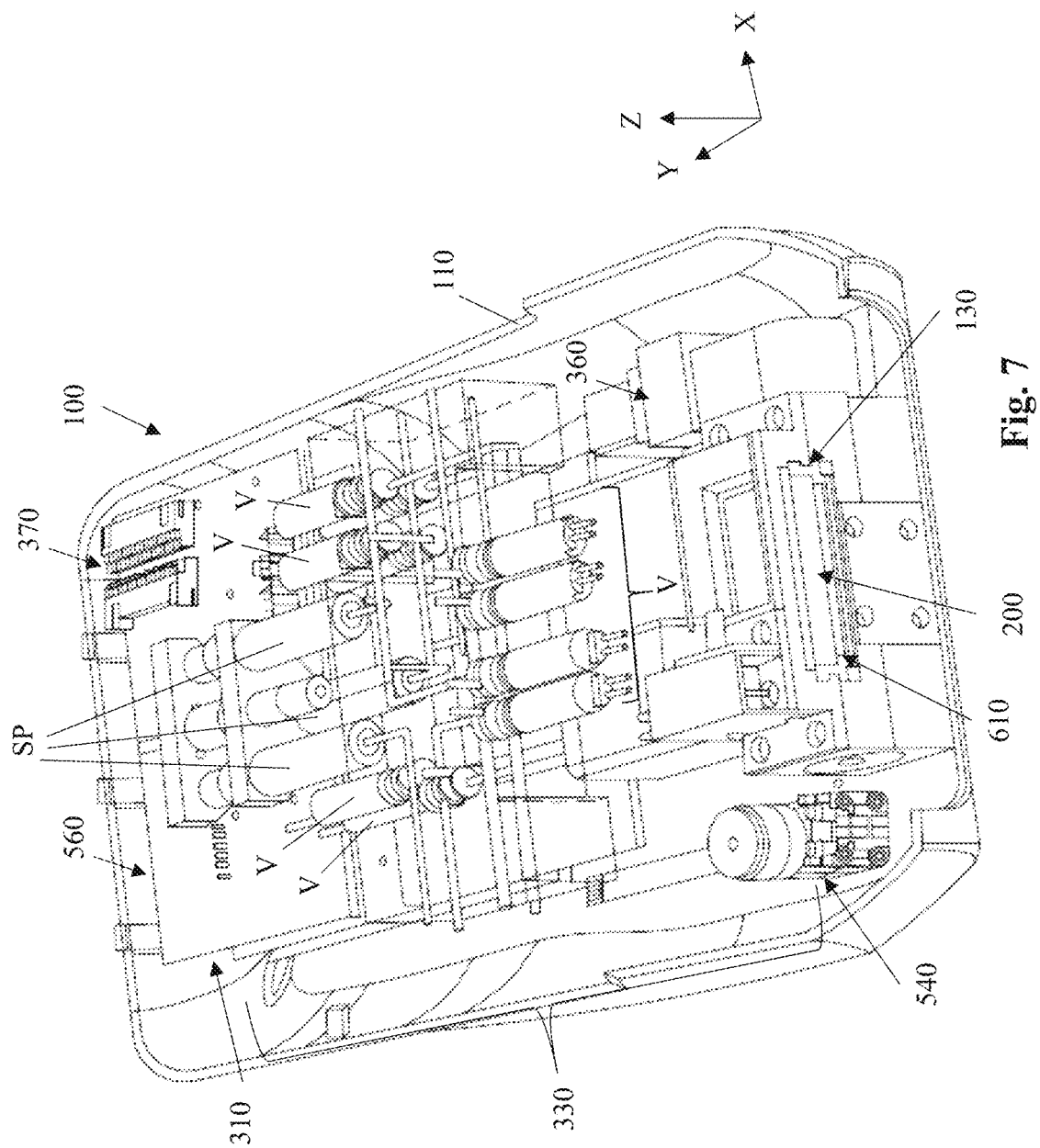
FIG. 7 shows an angled, top view of a bottom part of a housing of exemplary cartridge reader unit in accordance with an embodiment of the present disclosure.

Since magnetic field generator 360 is a source of electromagnetic energy and configured for use to stimulate magnetic nanoparticles near the GMR sensor chip 280 while reading the signal, in one embodiment, as shown in FIGS. 5-7, the magnetic field generator 360 may be positioned adjacent to and/or substantially around the cartridge assembly 200 when it is inserted into the housing 110. For example, the field generator 360 may be configured adjacent to or around the cartridge receiving opening 130 and/or the tray 610 such that, during power and operation to the magnetic field generator 360, magnetic fields may be on both sides, top and/or bottom of the cartridge assembly 200, e.g., to cause mixing and movement of a test sample and fluids therein.

FIG. 6 shows an additional (optional) automated blister pack puncture system 533 that may be included in the cartridge reader unit 100. Puncture system 533 may be configured to puncture or break blister packs 265, chambers, etc. that contain mixing materials (e.g., reagents, wash buffers, beads) for mixing in the cartridge assembly 200 while testing a test sample. For example, the puncture system 533 may include a pin or other sharp object that may be moved (e.g., via a motor, not shown) to puncture blister packs(s) during processing of a test sample. The placement of the puncture system is not intended to be limiting. The movement of the system 533 or its pin is also not intended to be limiting. In on embodiment, the pin is moved vertically (in the Z-direction) relative to an inserted cartridge assembly 200. In embodiments, the puncture system 533 may be placed to a side (e.g., left) of or on top of the area near the field generator 360, for example, and/or near the cartridge assembly 200. In an embodiment, the puncture system 533 may be configured to puncture on-board blister packs (e.g., in the sample processing card 210) or off-board (e.g., in the housing 110) blister packs. In some embodiments, puncture system 533 may be a heated automatic blister pack puncture system (e.g., which may be heated by heater 259) which may be used to thaw reagents which were solidified during storage, for example.

As previously described, mating of the cartridge assembly 200 with the cartridge reader unit 100 includes both pneumatic and electrical (electronic) mating between the two. Turning now to the pneumatic system 330, which is used, along with cartridge reader 310 and memory chip 275, to automate the process for processing and preparing a test sample injected into the cartridge assembly 200 by sequencing movement, flow rate, direction of fluids inside and along the sample processing card 210 and to a GMR sensor chip 280 (as previously noted), a pneumatic connection may be established between system 330 and a pneumatic interface (e.g., pneumatic control ports 235) on an inserted cartridge assembly 200. Pneumatic system 330 is configured at least to control positive and negative pressure applied to cartridge assembly 200. In accordance with an embodiment, pneumatic system 330 includes a manifold 520. Manifold 520 has flow channels 555 therein and is configured to communicate with the pneumatic interface (ports 235) of the cartridge assembly 200. In an embodiment, the pneumatic connection may entail use of a thin rubber gasket between the manifold 520 and ports 235 (e.g., at the interface on a top surface 218 of the card 210). The manifold 520 and gasket may be compressed to make a leak proof seal, in one embodiment. Alignment of the ports may take pace during the compressive force action, for example. Manifold 520 has flow channels therein, which may to branch to control ports 550 which connect to each of the pneumatic control ports 235 at the pneumatic interface. Manifold 520 may include any number of control ports 550 or openings in or on its mating surface (i.e., its surface that is aligned with ports 235 on the assembly 200). In an embodiment, the control ports 550 are provided on an underside surface of the manifold 520 (see, e.g., FIGS. 13, 14, and 15). The control ports 550 may be provided in a series, and, optionally, in one or more rows, in accordance with an embodiment. The number of control ports 550 and/or number of rows of control openings 550 that may be provided on manifold 520 is not limited. As shown in FIGS. 8 and 10, for example, a body of the manifold 520 may be positioned vertically above a loaded or inserted cartridge assembly 200 within the housing 110, in accordance with an embodiment. This is such that the pneumatic control ports 235 at the front end 205 of the cartridge assembly 200 may be aligned with corresponding control openings on the manifold 520. That is, the ports 235 may be configured such that they are facing upwardly (e.g., the tray 820) and thus facing an underside of the manifold 520. Ports 235 may be aligned with control openings on the underside surface of the manifold 520. If a gasket (described above) is also provided on the underside of the manifold 520, then a compressive force may be applied by electromechanical features (e.g., clamp system 630) within the housing 110 so that the gasket may be compressed to align the ports 235 and 550 and make a leak proof seal with the assembly 200.

At least one pump 540 and/or SP is configured to provide air pressure to the manifold 520, such that pressure and/or vacuum (suction) may be ultimately be applied to channels, reservoirs, chambers, and/or valves in valve array zone 230 in cartridge assembly 200. In accordance with an embodiment, the at least one pump 540 may be a diaphragm pump mounted in the housing 110. The number of pumps provided in the housing 110 may vary and the illustrative embodiments are not intended to be limiting. For example, in FIG.

Figure 14:
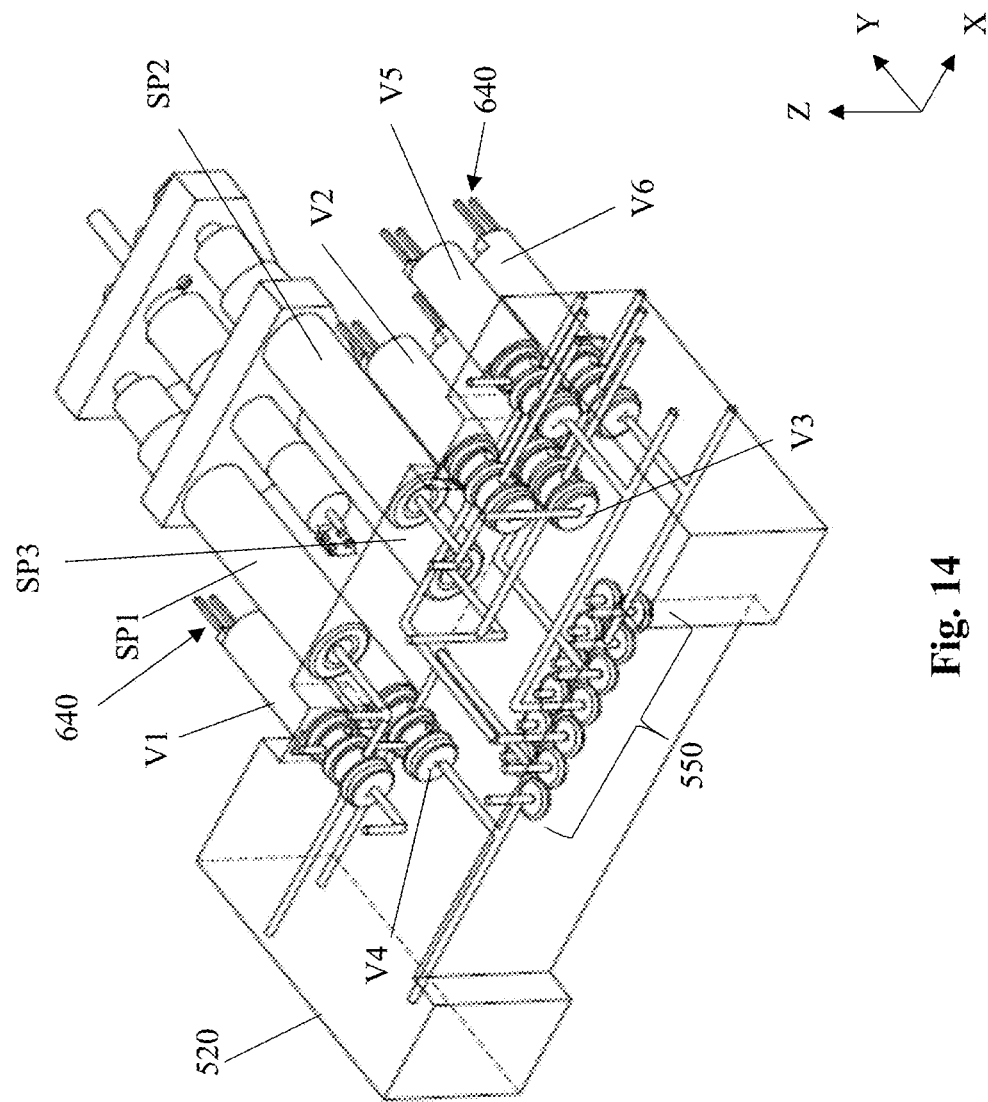
FIG. 14 shows a perspective schematic view of the parts shown in FIG. 13, which are part of the pneumatic system, in accordance with an embodiment of the present disclosure.

7, a single pump 540 is shown, while in FIG. 14, two pumps 540 are shown. Thus, one or more pumps 540 may be provided in housing 110. As shown in FIGS. 7-9, the at least one pump 540 may be mounted on a bottom portion and near a bottom of the housing 110, adjacent to the cartridge receiver 130. The pump(s) 540 may be configured to control the displacement and/or movement of elastomeric material in a valve array zone 230 of the card 210 by connecting to control ports 235 on the sample processing card 210 of the cartridge assembly 200. Pump 540 may also control movement of fluids—e.g., a separated test sample, reagents, wash buffers, etc.—through communication channels, metering chambers, and mixing channels within the card 210, via connection to pneumatic control ports 235, to direct a sample to the GMR sensor chip 820 (to thus perform analyzing and the designated test). In one embodiment, pneumatic control ports 235 may be used to control both fluid movement and valve movement within the cartridge assembly 200. In another embodiment, a second set of ports may be provided that distinctly control valves in valve array zone 230 of the cartridge assembly 200. In an embodiment, two pumps 540 may be provided in the housing 110; for example, one pump 540 may be used for fluid control, while a second pump 540 may be used for control of the valves in valve array zone 230.

Pump(s) 540 may be fluidly connected, for example, to multiple valves V and a barrel syringe pump SP (or piston pump) via manifold 520, which are configured to control air pressure to control ports 235. In accordance with an embodiment, such as shown in FIG. 14, pump(s) 540 may be configured to attach to manifold 520 via hose(s) 1400 (via hose fittings), which in turn attaches communicatively to assembly 200 via flow channels 555 and ports 550 and the settings of valves V and barrel syringe pump SP of the pneumatic system 330. In one embodiment, both pump 540 and syringe pump SP are provided in the housing 110. That is, pump(s) and syringe pump SP may work independently and without a fluid connection. Accordingly, in the embodiment shown in FIG. 14, the pump(s) 540 may be configured to attach to manifold 520 via hose(s) 1400 in order to communicate through particular flow channels 555 as determined by a position of one or more valves V. Manifold 520 may include a number of flow channels 555 therein that ultimately connect syringe pumps and/or valves of the pneumatic system 330 and pump(s) 540, via ports 550, to the ports 235 of the cartridge assembly 200 (and/or valve control ports, if provided).

In accordance with an embodiment, the pneumatic system 330 includes a multi barrel syringe pump. That is, the barrel syringe pump SP may include a plurality of barrel syringe pumps SP configured to communicate with the manifold 520 and its flow channels 555 therein, such as shown in FIG. 14. The number of syringe pumps SP is not intended to be limiting. In an embodiment, at least one syringe pump SP may be provided as part of pneumatic system 330. In one embodiment, such as shown in FIGS. 11-14, three syringe pumps—SP1, SP2, and SP3—may be provided as part of the pneumatic system 330. As shown in FIG. 12, syringe pumps SP1 and SP2 may be mounted relatively above syringe pump SP3 in a loose triangular arrangement, for example. This arrangement may allow each of the syringe pumps SP1, SP2, and SP3 to access different flow channels 555 and thus ports (e.g., ports 235 or 535) according to their position, in certain embodiments. However, this is exemplary only and the number of syringe pumps SP associated with the pneumatic system and manifold 520 are not intended to be limiting.

Moreover, while syringe pump(s) SP are shown and described herein, the pneumatic system 330 may alternatively include, in accordance with embodiments, one or more different types of pumps, in addition, or as an alternative to, syringe pump(s) SP. In accordance with embodiments, any vacuum generating pump could be provided as part of the pneumatic system 330 so as long as pressure is controllable (e.g., using pressure transducer feedback) in order to allow modulation of the pressure, as needed. Further, each pump SP and/or 540 is configured to be controlled and wired to the PCB 560. Generally, standard wiring or ribbon cables, as known in the art, may be used.

In an embodiment, the pressure and flow rate from the syringe pump(s) SP to the cartridge assembly 200 may be controlled by way of one or more transducers 510 provided on the PCB assembly 560. For example, the transducers 510 may be used to manipulate and modulate the pressure for example, change positive pressure to negative pressure, i.e., vacuum pressure, and thus a flow rate of the fluids within the channels of the cartridge assembly 200. As shown in the schematic view of FIG. 11, the transducers 510 may receive feedback regarding pressure application and thus be utilized to control syringe pumps SP associated with the manifold 520. In an embodiment, each of the syringe pumps SP may be electronically connected to a transducer 510. In accordance with an embodiment, each of the syringe pumps SP may include pneumatic cylinders which are configured to move relative to an outer barrel and controlled by a motor M (see FIGS. 11 and 12). Based the desired positive or negative pressure supplied to each of the ports 235 via manifold 520 and pneumatic system 330, fluids may be pushed and/or pulled through channels of the sample processing card 210 (and/or valves of the valve array zone 230 may be opened or closed) by moving the pneumatic cylinders within their respective outer barrels of the syringe pumps SP, for example. In some embodiments, motor M may be utilized to control a piston, plunger, and/or similar device to move fluid inside of the cartridge assembly 200 (e.g., in the same manner as described with reference to syringe pumps SP and valves V of the system 330).

The valves V of the pneumatic system 330 may be configured to be placed in at least an open position (e.g., "ON") and a closed position (e.g., "OFF"), and optionally therebetween, based on the input from cartridge reader 310 and any steps in a sample preparation and processing method, e.g., as determined via the memory chip 275. The valves are used to control flow of pressure through the manifold 520 and flow channels 55 and a logical sequence required for each assay/cartridge assembly 200. Each of the valves V may have an inlet fluidly connected to flow channels 555 in the manifold 520 and/or to syringe pump(s) SP. Each of the valves V may be configured to open or close fluid communication through flow channels 555 within the manifold 520, based on their position(s). The position of one or more of the valves V (open, closed, or even partly open) may be controlled by the cartridge reader 310. As generally represented by leads 640 being provided on each of the valves in the Figures, each valve is configured to be controlled (e.g., using 5 V DC) and wired to the PCB 560. Generally, standard wiring or ribbon cables, as known in the art, may be used. The number of valves V in the pneumatic system 330 and/or flow channels 555 in the manifold 520 are not intended to be limiting. Further, depending on the cartridge assembly 200 inserted into the cartridge reader unit 100, not all of the valves V provided in pneumatic system 330 and/or flow channels 555 and ports 550 may be utilized as part of the sample processing and preparation method.

Mounting of the syringe pumps SP, motor M, and/or valves V in the housing 110 may be provided by one or more brackets 1010, 1020 which are attached to one or more of the internal walls of the housing 110 (e.g., bracket(s) may extend from a top or a side wall). Brackets 1010, 1020 may be configured to fix syringe pumps SP such that they remain stable during operation of the cartridge reader unit 100. Further, internal walls, support structures, mounting plates, and/or other structural devices may be provided inside housing 110 to support any one or more of the PCB assembly 560 (and its circuit boards), manifold 520, pump(s) 540, and any other features provided inside the housing 110 of the unit 100, although they may not be explicitly shown or described herein. Also, one of ordinary skill in the art should further understand that additional features and/or parts may be provided as part of the system 330 and/or in the housing 110. For example, barb fittings may be used to connect rubber tubing to internal pumps like pumps SP, even though they may not be explicitly illustrated.

FIGS. 11 through 15 illustrate additional features of the pneumatic system 330. More specifically, these figures show exemplary arrangements of syringe pumps SP, valves V, and pump(s) 540, that are part of the pneumatic system 330, in a schematic fashion as well as mounted in the housing 110. For explanatory purposes only, FIGS. 11-15 illustrate one embodiment of valves V and syringe pumps SP associated with manifold 520, as part of the pneumatic system 330. In an embodiment, at least eight (8) valves V may be provided. In another embodiment, at least ten (10) valves V may be provided. In yet another embodiment, such as illustrated in the schematic of FIG. 16, eleven (11) valves V may be provided. Syringe pumps SP may be connected to the inlets of the manifold 520 to communicate with flow channels 555, through which flow is connected to and controlled by one or more valves V, and thus to/from control openings 550. Pump(s) 540 may be connected (e.g., via hoses 1400) to the manifold 520, and thus to the valves, on one side, either side, or both sides of the manifold 520.

Parts of the pneumatic system 330 may be mounted longitudinally within housing 110, in accordance with an embodiment herein. For example, as shown in FIGS. 8 and 10, the syringe pumps SP may be positioned such that their barrels are mounted longitudinally (and further, in this, horizontally) within the housing, parallel to the axis Y-Y, and thus the barrels may be configured to move longitudinally to deliver (positive pressure) or withdraw (negative pressure, or vacuum) air via the manifold 520 and thus to/from the cartridge assembly 200. In an embodiment, the valves V may be mounted longitudinally (and further, in this, horizontally) within the housing, parallel to the axis Y-Y.

Figure 11:
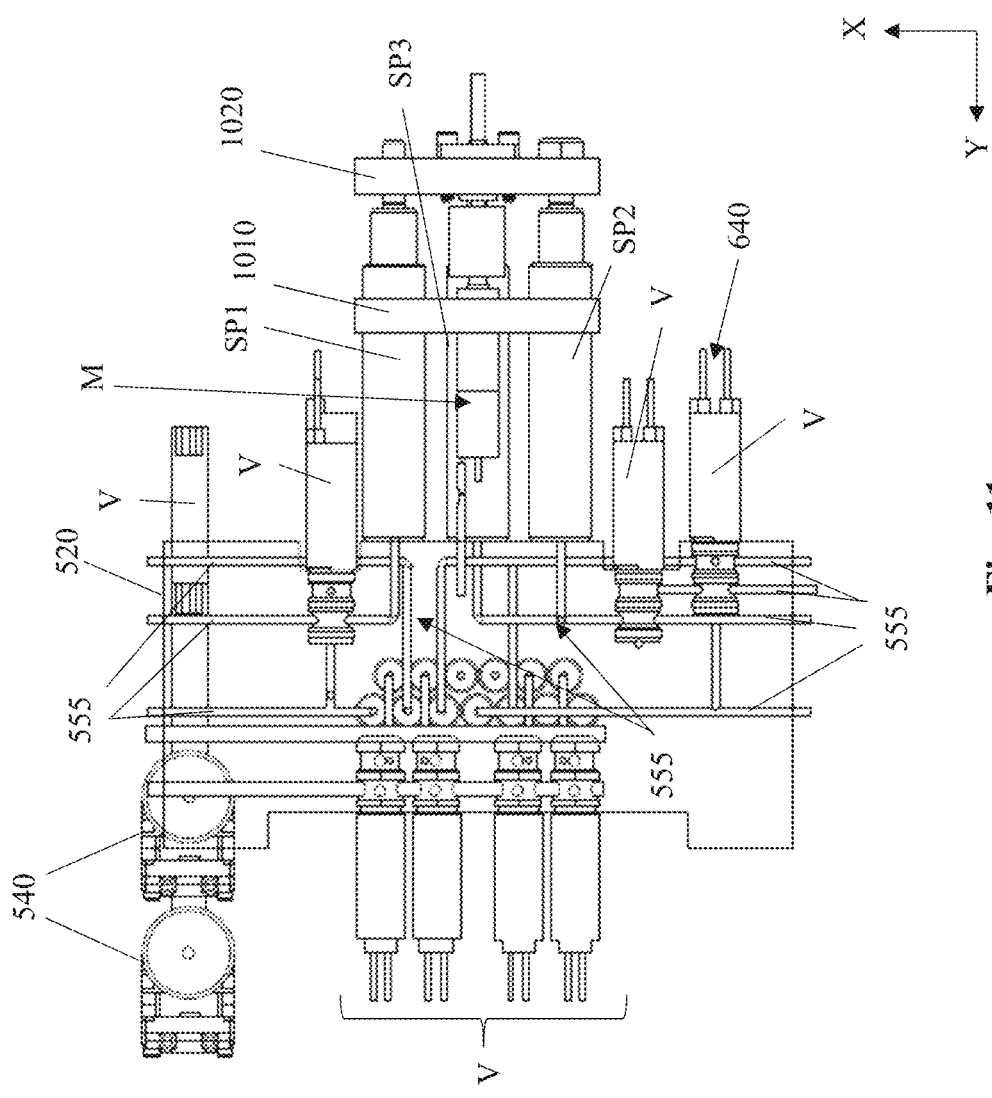
FIG. 11 shows a top schematic view of parts of a pneumatic system in the cartridge reader unit, in accordance with an embodiment of the present disclosure.
Figure 12:
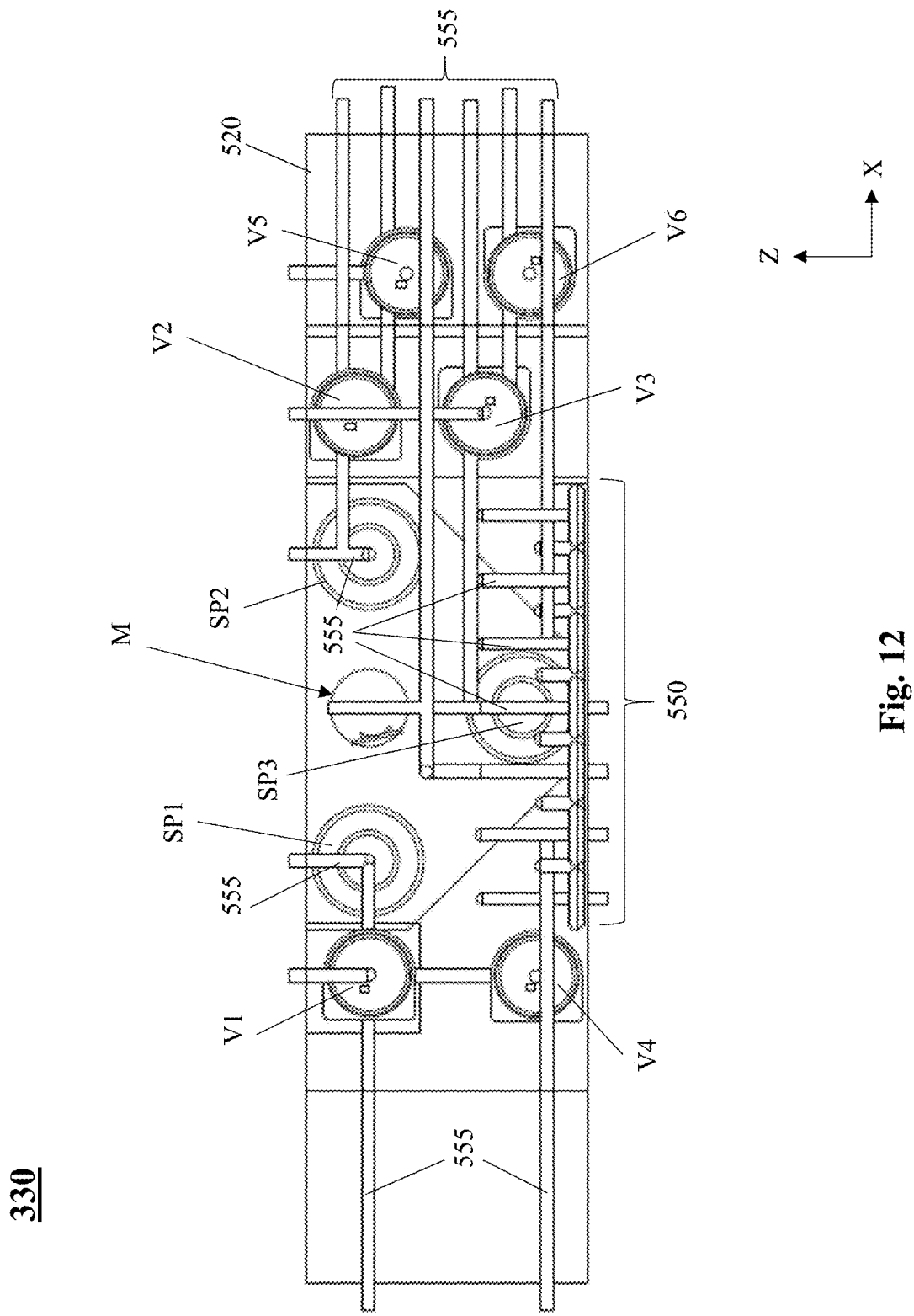
FIG. 12 shows a front schematic view of parts of FIG. 11 of the pneumatic system in the cartridge reader unit, in accordance with an embodiment of the present disclosure.
Figure 13:
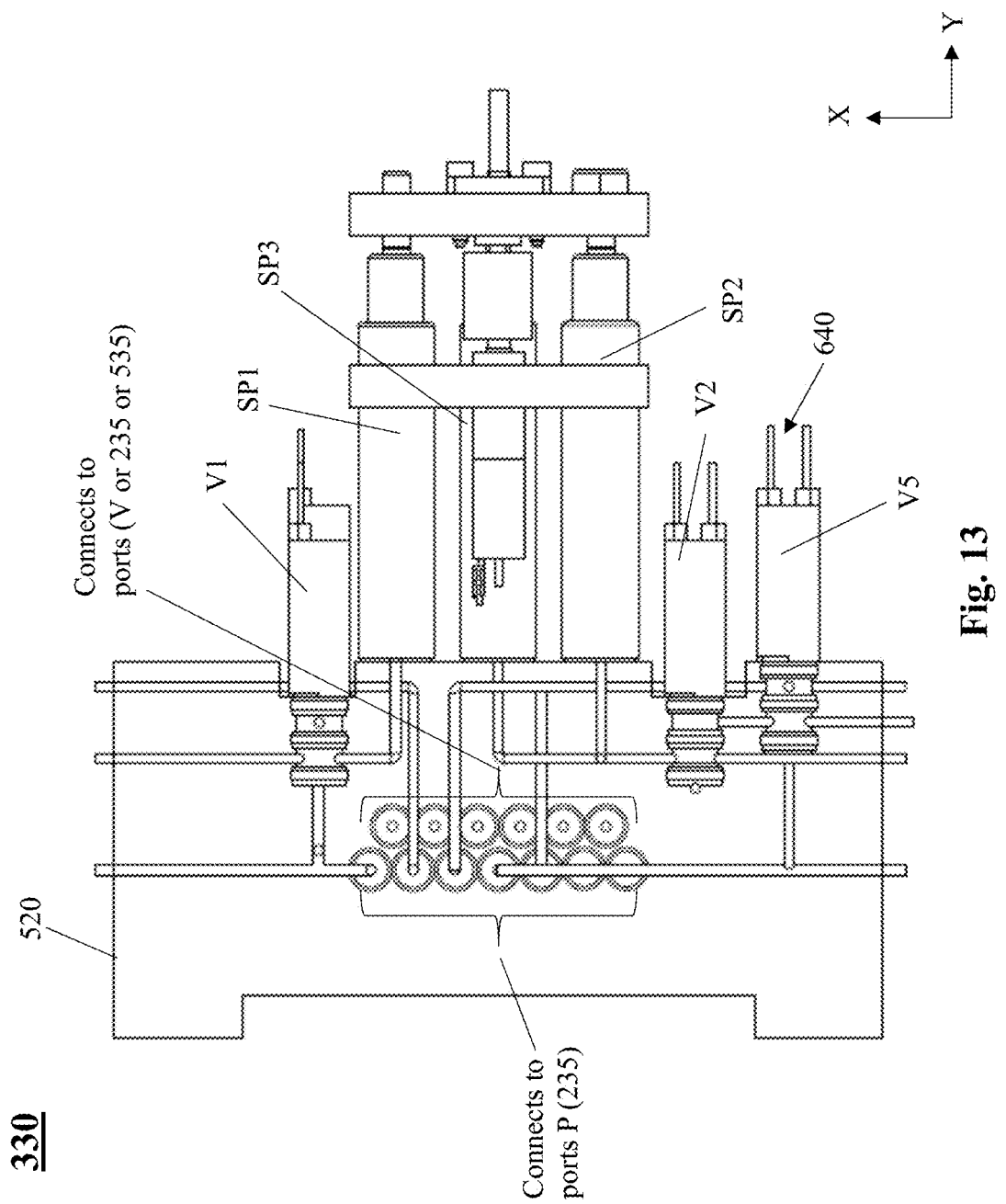
FIG. 13 shows a top schematic view of syringe pumps, valves, and manifold of the pneumatic system in the cartridge reader unit, in accordance with an embodiment of the present disclosure.

At least some of the valves V may be provided in first and second sets, e.g., on either side of the manifold 520 (see, e.g., FIG. 11, showing an exemplary first set of (four) valves on one side (left in this Figure) of the manifold 520, and a second set of (four) valves on the other side (right in this Figure) of the manifold 520; the three remaining valves not shown in FIG. 11), in accordance with an embodiment. In one embodiment, syringe pumps SP may be provided on the same side of the manifold 520 as the second set of valves. In one embodiment, a valve (11) may be utilized for further control of the fluid flow through flow channels 555 within the manifold 520 and/or pneumatic system 330 (e.g., despite the position of the other valves). Again, this is explanatory only and not intended to be limiting. This configuration shown in the Figures is one example of an assembly for the parts of the pneumatic system 330 within the housing 110 and with respect to their connection to manifold 520, but it is not intended to be limiting.

In accordance with an embodiment, there may be valves V that are configured to control flow within the cartridge assembly 200 for particular fluids therein. In accordance with an embodiment, there may be valves V that are configured to control a position of the valves in valve array zone 230 on the cartridge assembly 200. As an example only, FIG. 16 shows one embodiment wherein valves V1, V2, V3, V4, V5, and V6 are associated with flow channels 555 to ports P1-P7 (which correspond to pneumatic control ports 235 on a cartridge assembly 200). The valves V1-V6 may have their positions and flow rate controlled via transducers T1, T2, and T3 and syringe pumps SP1, SP2, and SP3, for example. Valves V7, V8, V9, and V10 may be connected to one or more pumps 540 (also shown in FIG. 15) via a hose connection and may be configured to control fluid flow through valve ports V1-V6 (which correspond to valve control ports 535 on a cartridge assembly 200, if provided thereon, or alternatively ports 235 which are designated to control positions of elastomeric material 212 of valves in valve array zone 230).

Figure 15:
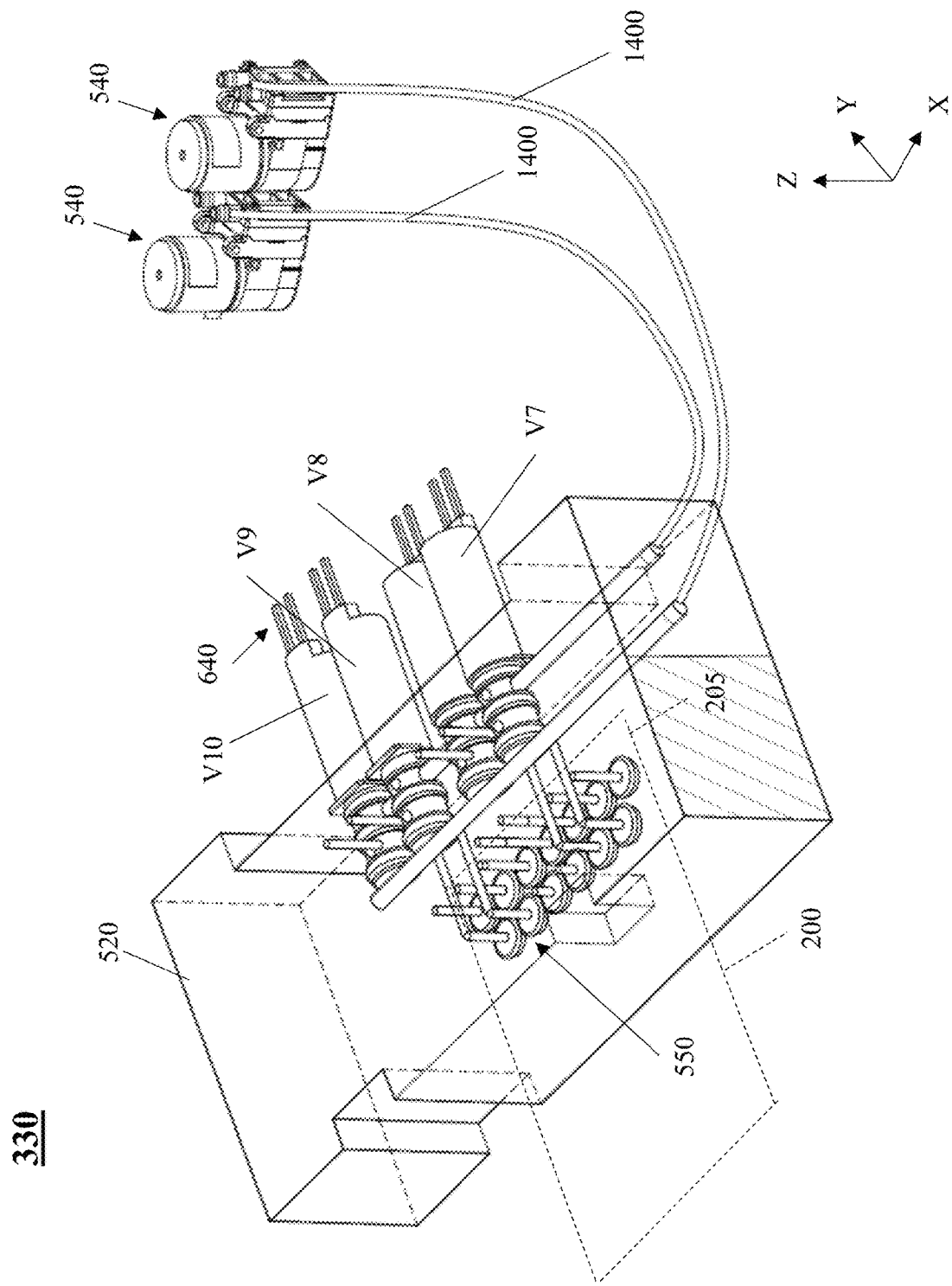
FIG. 15 shows a perspective schematic view of valves and pumps associated with the manifold of the pneumatic system in the cartridge reader unit, in accordance with an embodiment of the present disclosure.
Figure 16:
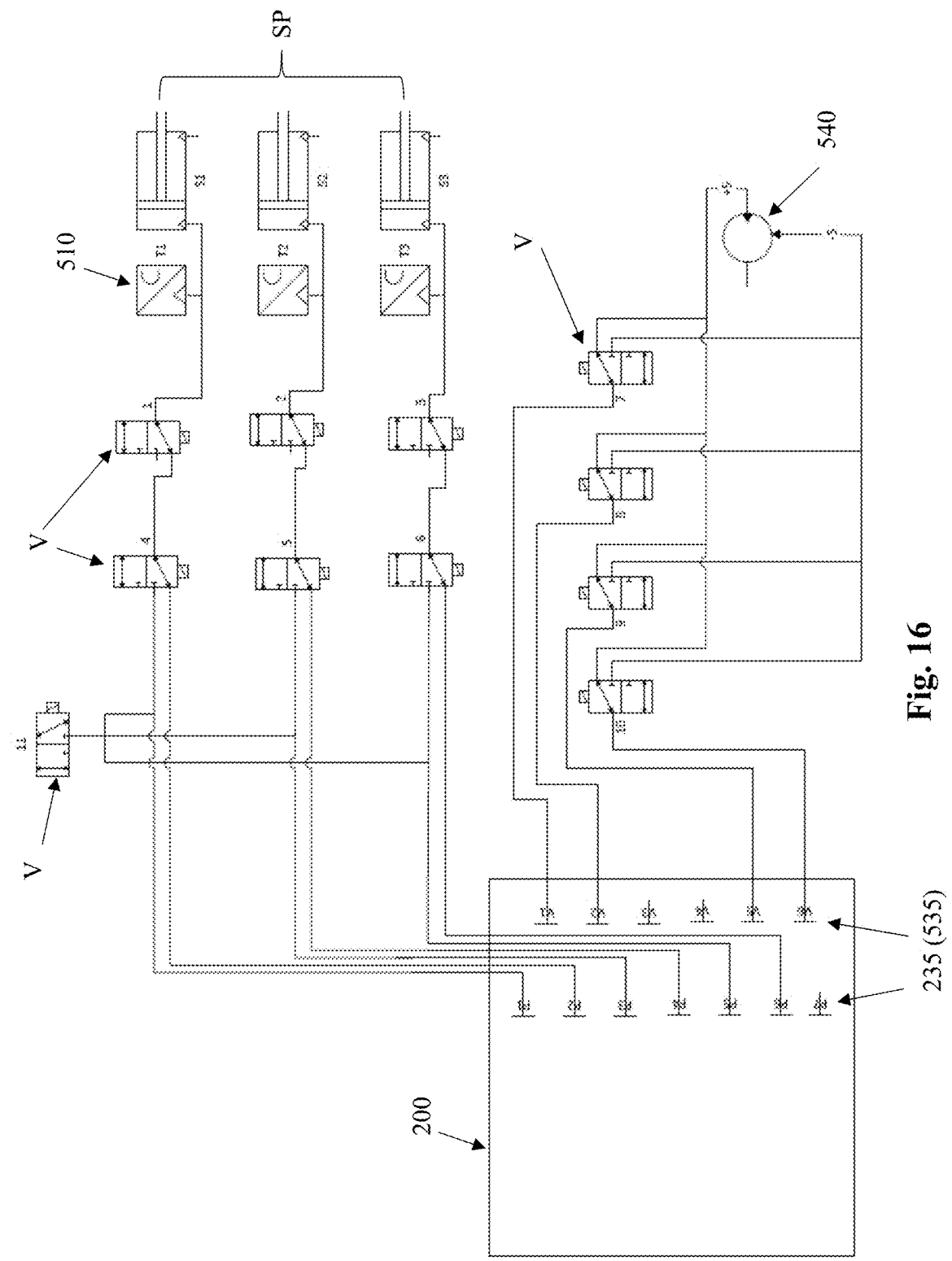
FIG. 16 shows a schematic of a control diagram showing syringe pumps, transducers, valves, flow channels (in a manifold), pumps of the pneumatic system associated with ports on a cartridge assembly, in accordance with an embodiment of the present disclosure.

FIGS. 13-16 show in greater detail examples of valve connections and fluid connections between syringe pumps SP1, SP2, SP3, valves V1-V10, and manifold 520 and the cartridge assembly 200, in accordance with one exemplary and non-limiting embodiments. When the cartridge assembly 200 is inserted or removably mounted in the unit 100, its pneumatic control ports 235 (and optionally, valve control ports 535) may be aligned with control openings 550 on manifold 520 (see, e.g., dashed lines in FIG. 15, showing exemplary placement of assembly 200 relative to manifold 520, with ports 235 being at its front end 205). As shown in FIGS. 14 and 16, syringe pumps SP1, SP2, and/or SP3 may be configured to control flow using one or more control openings 550 (and thus ports 235) via one or more valves V and flow channels 555 in order to control flow of a test sample that has been filtered to metering channels within the card 210, and or control flow of wash buffers and or bead solutions to GMR sensor channels, for example. Further, syringe pumps SP1, SP2, and/or SP3 may be connected to one or more ports 235 (or Ports P2-P6 (see FIG. 16)) to control flow of bead solution from a well or blister pack through the card 210 via one or more valves V and flow channels 555. In another embodiment, syringe pumps SP1, SP2, and/or SP3 may be configured to control flow of a test sample from metering channels to a GMR sensor chip 280 via one or more valves V and flow channels 550. In this case, control flow may refer to selectively applying a vacuum pressure (negative pressure) to pull a test sample and/or mixing materials through various communication channels and features within the card 210 of the assembly 200, and/or to selectively applying a positive pressure to push the test sample and/or mixing materials through said various communication channels and features, in accordance with an embodiment. Generally, the movement of fluids is designed to prepare and push a test sample to at least one GMR sensor chip 280 provided in the cartridge assembly 200 such that a reading (e.g., of biomarkers) is performed and determined via at least the cartridge reader/control unit 310.

Figure 17A:
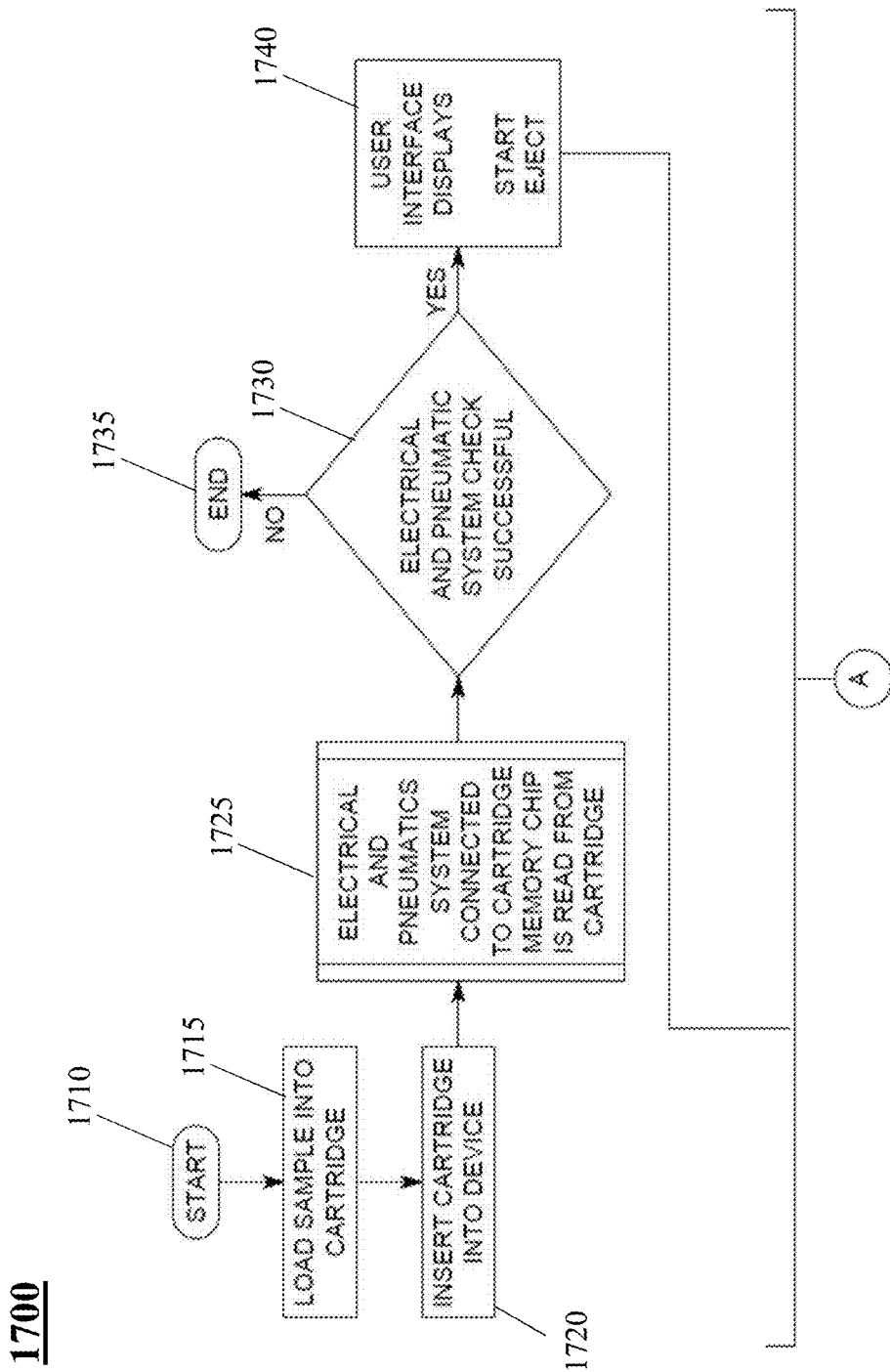
FIGS. 17A-17B steps of a method for performing analyte detection when using features of the herein disclosed system, in accordance with an embodiment.
Figure 17B:
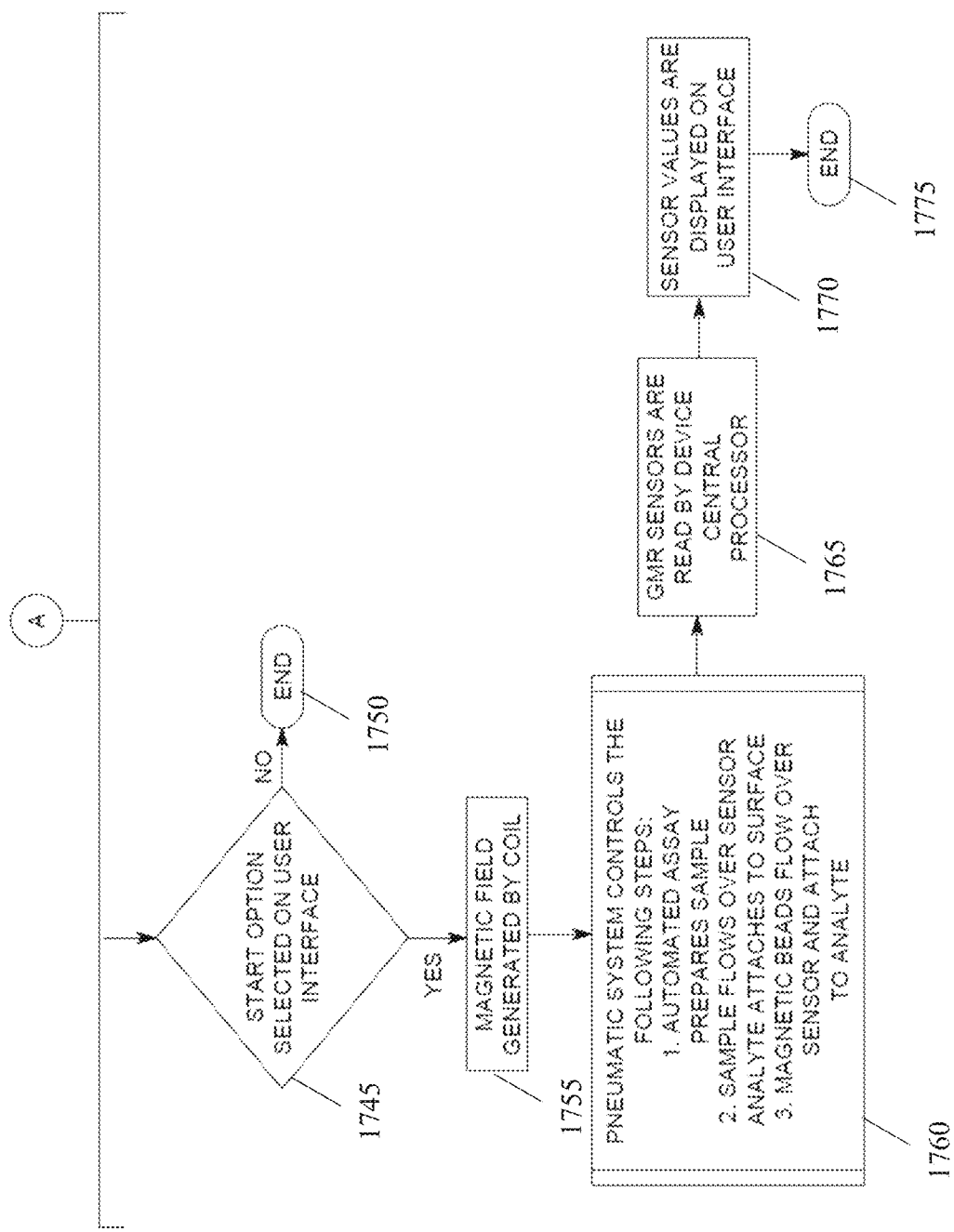

FIGS. 17A-17B provide a flow chart of a method 1700, in accordance with an embodiment, of utilizing the system 300 to perform analyte detection using the disclosed cartridge assembly 200 and cartridge reader unit 100. Similar steps may have been noted previously with respect to the method of FIG. 4, and thus steps from the method of FIG. 4 may be incorporated into this method 1700, or vice versa, in accordance with embodiments herein. FIG. 17A shows that at step 1710 the method starts or begins. At step 1715, a (whole) test sample is loaded into card 210 of the cartridge assembly 200. At step 1720, the cartridge assembly 200 is inserted into the device or cartridge reader unit 100. At step 1725, the electrical and pneumatics system are connected and the cartridge memory chip 275 is read from the cartridge assembly 200 (e.g., read by cartridge reader 310/control unit, or PCB assembly 560, in the unit 100). At step 1730, the cartridge reader 310 determines if the electrical and pneumatic system check is successful. That is, for example, it may be determined if communication is established and connected. If the answer is NO at step 1730, then method ends at 1735. Optionally, the display of the unit 100 may alert a user that no connection has been established. Alternatively, if the check is successful at step 1730, i.e., YES, then at step 1740 a user interface 140 and/or display 120 may display that the process may start and/or initiate the process. It may also optionally display and/or initiate an eject function, for ejecting the cartridge assembly from the unit 100. Continuing onto FIG. 17B, a start option may be selected (by a user) on a user interface and/or display at step 1745. If the start option is not selected at step 1745, i.e., NO, then the method ends at 1750. If the start option is selected at step 1745, i.e., YES, then a magnetic field may be generated by the field generator 360 (via cartridge reader 310) at step 1755. Then, at step 1760, the pneumatic system 330 may control a number of steps, including, for example, 1. Automated assay prepares sample (e.g., mixes with mixing materials such as reagents); 2. Sample flows over GMR sensor chip(s) 280 and analyte attaches to surface of the sensor chip 280; 3. Magnetic beads flow over sensor ship 280 and attach to the analyte. Thereafter, at step 1765, the GMR sensor chip(s) are read by the device central processor, i.e., the cartridge reader 310. At step 1770, sensor values (i.e., test results) may be displayed on the user interface 140 and/or display 120. The method then ends at step 1775.

The pneumatic system protocol (and steps at 1760 in method 1700) for controlling pneumatic system 330 may be determined based on the test sample being processed and the test being performed. More specifically, the sample processing card 210 of the cartridge assembly 200 may be configured with a number of channels, mixing materials, and devices, which will allow for processing of a sample such that it may be read by GMR sensor chip 280 (that is included in its attached substrate as part of the cartridge assembly 200). As previously noted, when the assembly 200 is inserted into the housing 110, parameters associated with and/or stored in the memory chip 275 may be read by the control unit 310/PCB assembly 560. Part of these parameters associated with a memory chip 275 may be the pneumatic system protocol, e.g., commands, connections, time, and units, that need to be applied to the cartridge assembly 200 by the pneumatic system 330.

FIG. 31 shows one particular example of steps, commands, settings (e.g., pressure settings) and times associated with one embodiment for processing a test sample (e.g., a two step card design). As shown, for each step, ports may be opened or closed for a period of time (e.g., seconds) and a pressure flow (e.g., plus or minus 5 psi) may be applied to the cartridge assembly 200 via the pneumatic system 330 (valves V, pumps) in the unit 100.

Figure 18:
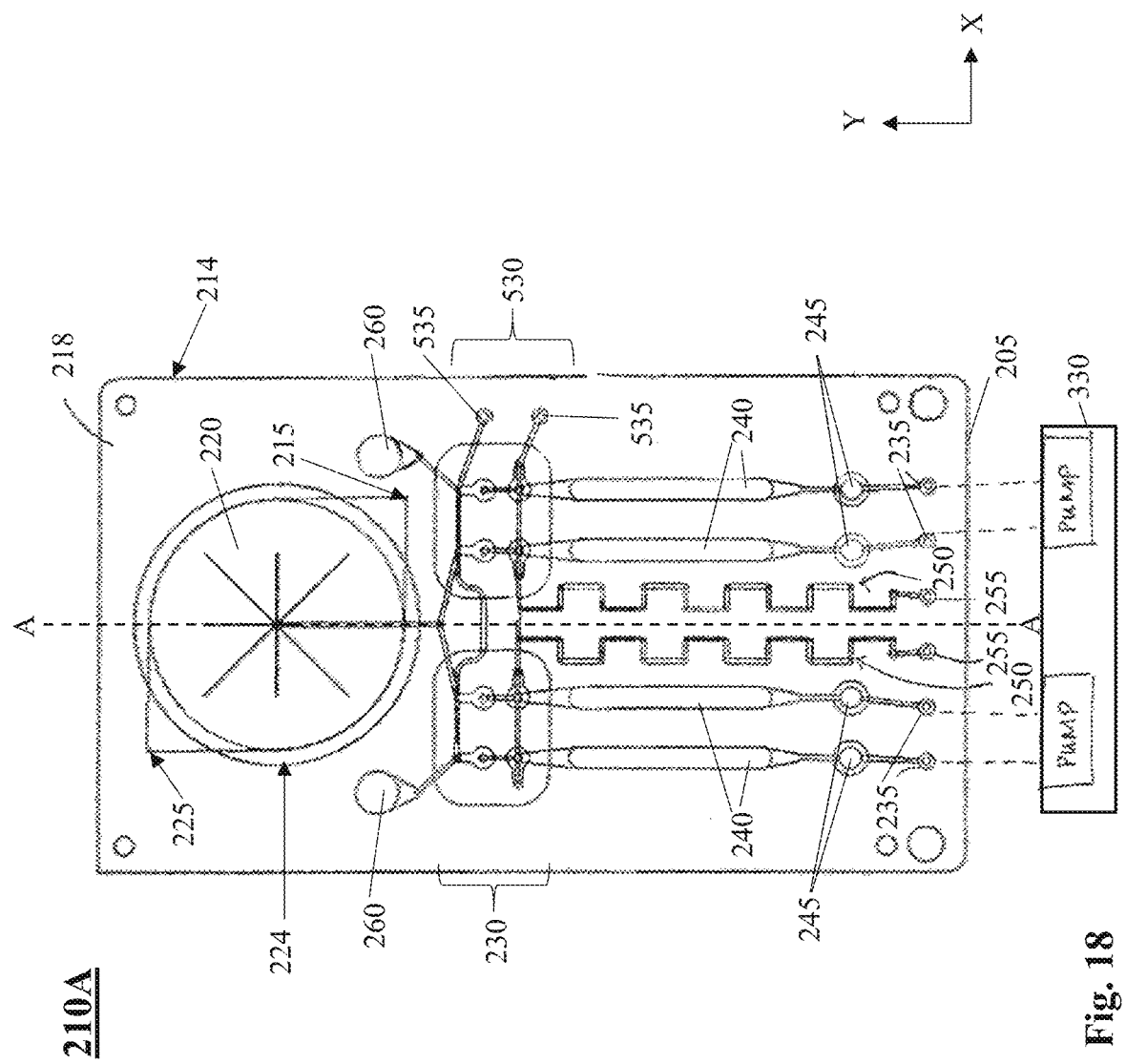
FIG. 18 is a top or overhead view of a sample processing card, configured for use as part of a cartridge assembly, in accordance with an embodiment therein.

In the description below, FIGS. 18-26 may be referenced to help illustrate features of an exemplary sample processing card 210 that is part of the cartridge assembly 200 used in the cartridge reader unit 100, forming the herein disclosed system 300. However, it should be understood that FIG. 18 is an example of a sample processing card 210A configured for use as a sample processing card in the cartridge assembly 200, in accordance with an embodiment therein, and that FIGS. 19-26 are illustrative only, and none of these embodiments are intended to be limiting. As noted previously, the cartridge assembly 200 used with cartridge reader unit 100 may include any number of features as disclosed in the incorporated PCT/US2019/043753 application.

Generally, a sample processing card 210 may include a sample injection area, a valve array zone 230, a mixing zone, a pneumatic control interface (also referred to herein as a pump interface or pneumatic interface) and a control and delivery zone (to sensor chip 280). Any of these areas and/or zones may be positioned relative to one another and/or overlap one another (e.g., in different layers of the card). The sample injection area is an area on the card for injecting the whole test sample. Valve array zone 230 includes a number and/or a series of valves therein that are controlled by the pneumatic system 330 in the cartridge reader unit 100 for directing and/or mixing fluids within the card 210. The valves in this zone 230 may be connected to communication channels within the sample processing card 210. Mixing zone refers to areas used to mix the separated test sample with and/or move other fluids (e.g., reagents, wash buffers, magnetic beads). The valves (e.g., with elastomeric deflection portions) in the valve array zone 230 may be selectively controlled between open and closed positions to allow for selective delivery through communication channels, e.g., delivery of the test sample to fluid metering chamber(s) 240 that may be provided in the mixing zone, for mixing with reagents, buffers, etc., for example. Control and delivery zone may be an area on the card 210 that communicates with the cartridge reader 310 of the unit 100 as well as the pneumatic system 330 thereof. In an embodiment, a number of ports 235 (at least one pneumatic control port 235) for controlling movement of the fluids within channels of the card 210 are provided in the pneumatic control interface. In some embodiments, the control and delivery zone may also optional include ports for controlling the positions of the valves in the valve array zone 230. Each pneumatic control port 235 has a corresponding communication channel fluidly connected thereto for connection with other features (e.g., metering chamber) within the card 210. These zones and the description thereof are exemplary only and not intended to be limiting.

As previously noted, in accordance with an embodiment, a sample processing card 210 may include a sample injection port 215, which may be provided on the card 210, for receiving the test sample within a body of the card. The injection port 215 is configured to receive a whole test sample, e.g., whole blood, urine, etc., in accordance with some embodiments herein. In other embodiments, the test sample may be pre-separated (e.g., serum from blood) before injecting into the injection port 215. The injection port 215 may include a small opening with a receiving hole provided in the top surface 218 of the card 210 that extends vertically (downwardly, in the Z-direction) at a depth into the card 210 and optionally through to the filtration membrane, e.g., filter 220.

The filtration membrane 220 may be provided between or sandwiched at a depth between the top surface 218 and bottom surface 222 of the sample processing card 210, in accordance with embodiments. In the illustrated embodiment of FIG. 18, for example (as well as other Figures), the filtration membrane 220 of sample processing card 210A is depicted as being generally circular; however, the area or shape of the membrane 220 is not intended to be limited. As generally understood by one of skill in the art, the filtration membrane 220 is formed from a material configured to receive an injected whole test sample and separate a test sample (for further preparation, e.g., with reagents, buffers, magnetic beads) from that sample. In embodiments, the filter membrane 220 may be a blood filtration membrane, e.g., to separate a plasma sample from whole blood. The filtration membrane 220 may be formed from an asymmetric filter material, for example. Such a material may have an increasing smaller pore size on its underside. In the case of a whole blood test sample, for example, the membrane 220 may be used to remove red blood cells and other large biological materials from the patient test sample injected into the injection port 215, and provide plasma for further processing in the sample processing card 210. In other embodiments, the filter may be provided in the form of a glass fiber membrane 220A. For example, glass fiber membrane 220A may be used for nucleic acid extraction (whereas filter membrane 220 is used to filter plasma from whole blood), in accordance with an embodiment. While generally filter 220 may be used throughout the description, it should be understood that reference to filter or filter membrane 220 and its features may also refer and apply to glass fiber membrane 220A, in this disclosure.

As previously noted, filter 220 (or 220A) may be optional within the card 210 and cartridge assembly 200. In an embodiment, for example, the test sample may be separated by a user or operator outside of the cartridge assembly 200. As an example, in the instance of utilizing whole blood as a test sample, a user may first separate serum or plasma therefrom, i.e., outside of the assembly 200. Accordingly, use of a filter in the assembly 200 may not be required.

In use, the test sample (e.g., whole blood) may be loaded, introduced, or injected (e.g., using a pipette or needle) into the small opening of injection port 215. The sample may then be configured to spread laterally through and across the filtration membrane 220 to purify and/or separate components of the sample (e.g., in the case of an injected whole blood sample, the filter 220 will filter the blood to yield plasma). The separated test sample (e.g., plasma) may settle into a bottom portion or receiving area 224, also referred to herein as a sample chamber 224, in the sample processing card 210. This receiving area 224 may be provided adjacent to or below (in the vertical direction, i.e., direction of depth or height; in the Z-direction) the filtration membrane 220, for example. In an embodiment, the loaded or injected sample will wick across the filtration membrane 220—as represented in some Figures by the lines therein—e.g., up and/or diagonally to a side opposite the injection port 215, where the vent port 225 may be positioned or provided.

Vent port 225 is an opening in the sample processing card 210 that extends vertically at a depth between the area of the filtration membrane 220 and the top surface 218 of the sample processing card 210. In an embodiment, the depth of the vent port 225 extends from the receiving area 224 (e.g., top or bottom of the area 224, or sample chamber) to the top surface 218. Vent port 225 is open to the atmosphere and configured to vent air from the card. Vent port 225 may be similar in size to the opening of injection port 215, in accordance with an embodiment. The vent port 225 extends down into same plane as the membrane 220, in one embodiment. This vent port 225 allows pressure to be vented or released from inside the sample processing card (e.g., from the membrane 220 and/or receiving area 224, or other connected channels therein) and out to the atmosphere; e.g., as a blood test sample is injected and wicked in the membrane 220, it separates the plasma and any air in this area is pushed out through vent port 225. In accordance with an embodiment, vent port 225 may be positioned relatively opposite (e.g., 180 degrees) to the injection port 215. In the exemplary illustrated embodiment of FIG. 18, for example, the vent port 26 is shown on an upper, left side near the membrane 220. In another embodiment, the vent port 225 and injection port 215 may be positioned closer together, or on a same side of the sample processing card. In an embodiment, a channel, guide, or other portion may be provided in a layer of the sample processing card that routes the channels around the membrane 220, for example. In one embodiment, the location of the injection port 215 and vent port 225 may be switched or rotated to another location around or relative to the filtration membrane 220. For example, referring to the embodiment of FIG. 18, the injection port 215 and vent port 225 locations may be switched. In another embodiment, the ports 215, 225 may be positioned along another line, e.g., a vertical line, a horizontal line, or angled line, across/through and relative to the membrane 220. Accordingly, the illustrated locations of the ports 215, 225 is not meant to be limiting.

According to some embodiments, sample processing card 210 may include one or more air vents (or air ports) therein that may be used to vent and/or pull air therethrough. In some cases, vent port 225 may act as the air vent, while in other embodiments, air vent may be a separate port. In an embodiment, the air vent and/or vent port 225 may be configured to allow air flow to dry the contained fiber membrane (e.g., a glass fiber membrane). In one embodiment, the air vent may be normally closed via a valve, whose position (open or closed) may be controlled by the pneumatic system 330 (e.g., via connection to a designated port 235 and communication channel(s)).

From this sample injection area, the separated test sample within receiving area 224/sample chamber is designed for use and, optionally, mixing with a reagent, buffer, magnetic beads, etc. More specifically, the separated test sample is configured to be moved within the card 210 to prepare the test sample and then direct it to a GMR sensor chip 280 for sensing and outputting results to a user/operator. Fluid communication channels may fluidly connect the injection port 215 and receiving area 224 to a mixing material source and/or metering chamber(s), and/or other features within the card 210, as described in greater detail below.

In the illustrated sample processing card 210A of FIG. 18, for example, in accordance with an embodiment, the card 210A may be configured to have features that are similar on either side (left and right) of a longitudinal centerline A-A (provided in the Y-direction) when viewed overhead (see FIG. 18), and thus are mirror images of each other. Accordingly, the sample processing card 210A of FIG. 5 provides assay areas that are split and arranged in a parallel manner, allowing multiple assays at one time. In FIG. 18, similar reference numbers are used to represent features provided on both sides (i.e., left and right) of the sample processing card 210. As will be further evident based on the description below, such a structural arrangement on the sample processing card 210A of FIG. 18 allows for better mixing of the test sample (e.g., plasma) and reagent, buffer, magnetic beads, etc., along with use of control mechanisms (from unit 100), thereby resulting in better functioning of the card and thus higher assay specificity.

In accordance with an embodiment, some of the mechanisms used to control fluid mobility and mixing of the separated test sample in the sample processing card 210 are a series of valves provided in the valve array zone 230 as well as pneumatic control ports 235 in the pneumatic control interface. For example, plasma that is separated from a blood sample using the filtration membrane 220 in the receiving area 224 may travel through a sample delivery channel that extends from the receiving area 224 (in this case, from a center, bottom portion thereof) via controlling such valves and ports using a controller and/or pump(s) of pneumatic system 300 that may be connected to the sample processing card 210 and cartridge assembly 200, in accordance with one embodiment.

In accordance with embodiments herein, any of the embodiments of the sample processing card 210 may be configured to be positioned as part of the cartridge assembly 200 such that pneumatic control ports 235 of the pneumatic control interface are provided at an end of the card 210 that is first placed into the cartridge receiver 130 of the cartridge receiver unit 100. More specifically, while the Figures may generally depict ports 235 (or their interface) a bottom end or area of the card 210 when viewed longitudinally (e.g., with injection port 215 near a top of the card and ports 235 near a bottom), this bottom end of the card 210 with the pneumatic control ports 235 may actually be referred to herein as a "front end" or an "insertion end", when referring to insertion of the cartridge assembly 200 into unit 100.

It should be noted that although a single sample delivery channel may be shown in some of the embodiments in the Figures, it is envisioned that two or more sample delivery channels may be provided in the sample processing card 210. For example, in an embodiment, two or more sample delivery channels may extend from the receiving area 224 to another features within the card (e.g., metering chambers 240).

A series of valves may be provided in the valve array zone 230, in accordance with an embodiment. In an embodiment, a first set of valves is provided in the housing and includes a first valve and a second valve that are each configured for movement between an open position and a closed position. In one embodiment, a second set of valves is also provided in the housing, each valve being configured for movement between an open position and a closed position. Valves may be separated and may be provided on either side of the longitudinal centerline A-A of the card, in an embodiment. In another embodiment, the valves may be separated into rows, e.g., a row of first valves extending parallel to a row of second valves. The row of first valves may be positioned longitudinally above the row of second valves, for example. In an embodiment, the valves and valve array zone 230 may be provided adjacent to or relatively longitudinally below the filtration membrane 220 (relative to and along the centerline) within the card 210. In accordance with an embodiment, a series of valves may be provided in the valve array zone 230 relatively below the filtration membrane 220 in the vertical (Z) direction. In another embodiment, the valves may be provided on the same side of a longitudinal axis or centerline A-A of the housing. In yet another embodiment, valves may be provided in the valve array zone 230 relatively above the filtration membrane 220 in the vertical (Z) direction. As such, it should be understood that a location of the valve array 230 with respect to the filter 220 along the card (longitudinally) and/or within the layers of the card is not critical for the micro fluidic communication channels, as the fluid may be routed any number of places (vertically and/or longitudinally) on the card 210 via the channels therein.

Figure 19:
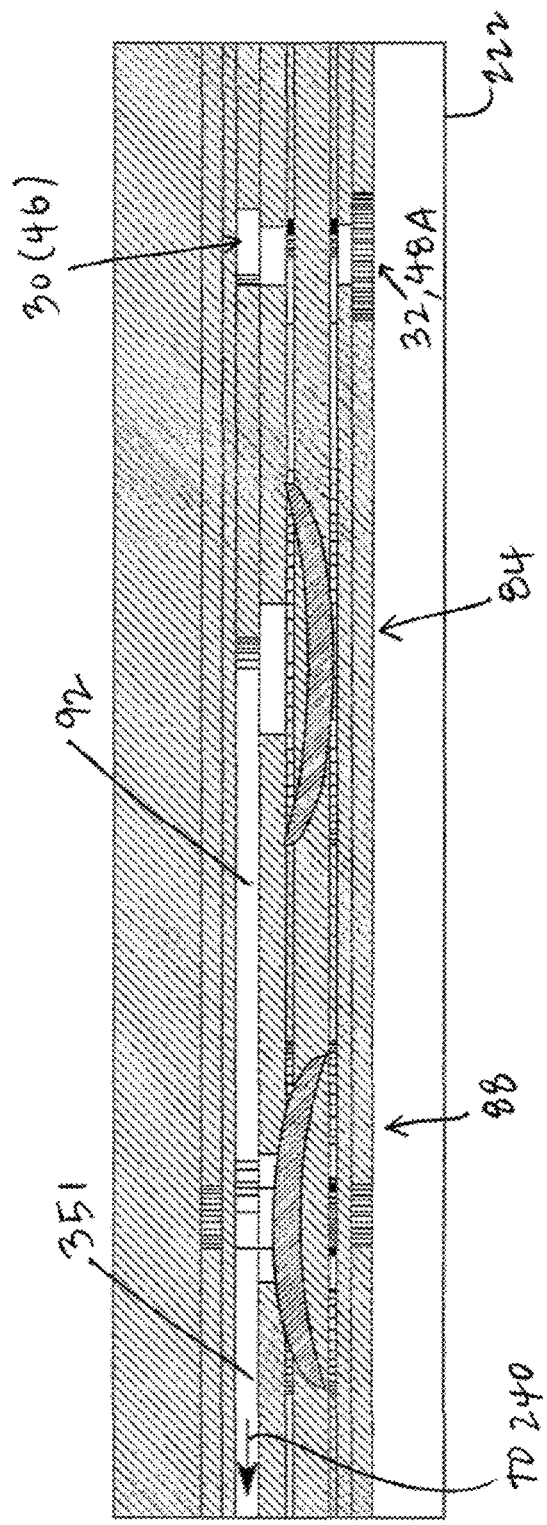
FIG. 19 is a schematic of a cross-section of the sample processing card of FIG. 18 illustrating an example of positioning of the valves in a first state.
Figure 20:
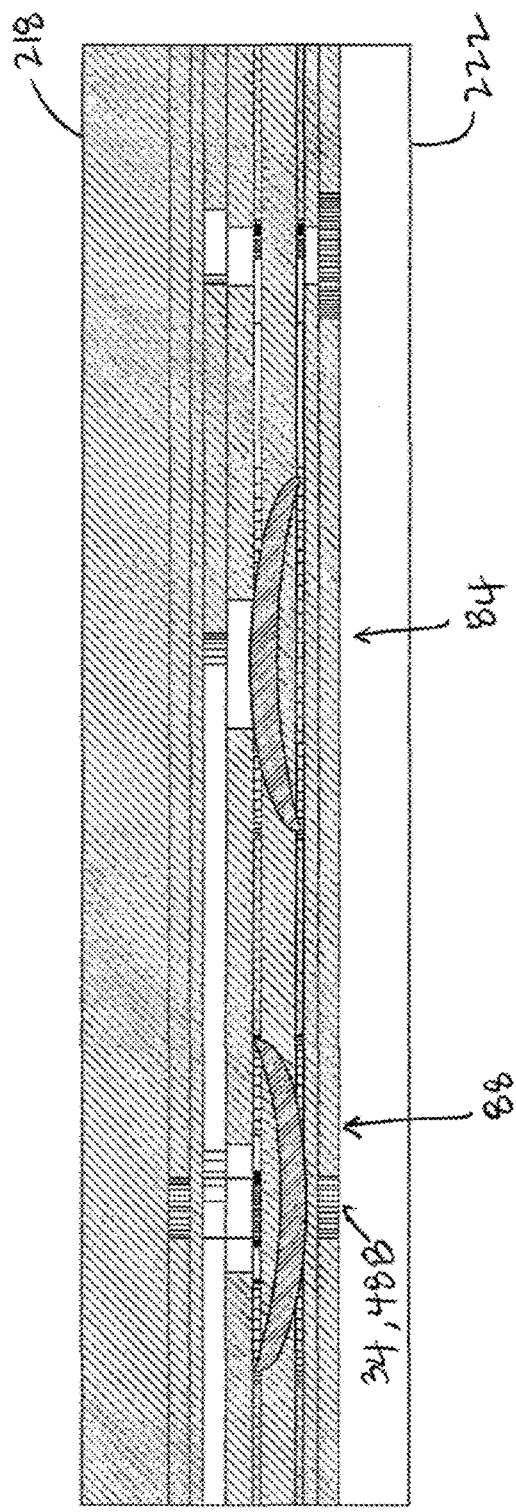
FIG. 20 is a schematic of a cross-section of the sample processing card of FIG. 18 illustrating positioning of the valves in a second state.

In one embodiment, each valve array zone 230 may include, or be formed from, an elastomeric material 212. As illustrated in the exemplary illustrated embodiment of FIG. 18, the location of the elastomeric material 212 is represented by generally rounded rectangle section, which may be provided below the top surface 218 and at a depth within the sample processing card 210, for example. An example of the positioning of the elastomeric material 212 at a depth or in an intermediate layer of the card 210 is shown in greater detail in FIG. 19 and FIG. 20. The elastomeric material 212 may be placed within a body of the sample processing card 210 such that valves that are formed in layers or within the body of the card. The elastomeric material 212 may include pockets and/or elastomeric deflection portions (as shown in FIGS. 19-20) that are/act as the valves, which are aligned with interior channels within the card. Movement of the deflection portions via positive pressure (e.g., pressurized air or vacuum from pneumatic system 330) between open and closed positions allows fluid (plasma, reagent) to move within the channels and housing parts, as described below.

The valves (i.e., elastomeric deflection portions) in the valve array zone 230 may be selectively controlled to allow for selective delivery of the separated test sample from the whole sample and/or a reagent, wash buffer, beads, etc. for mixing with the plasma to fluid metering chamber(s) 240, for example. As detailed later, controller(s) and/or pump(s) of pneumatic system 300 that are connected to the cartridge assembly 200 (and thus sample processing card 210) may be activated to control a position of the valves in the elastomeric materials 212/zone 230 and/or to apply positive and/or negative pressure (suction or vacuum) to the sample processing card 210 such that, depending on the positioning of the valves, the fluids (plasma and/or reagent) move within and throughout channels provided in the sample processing card 210.

In an embodiment, to move and deliver a separated test sample into the metering chambers 240, the sample delivery channel (from receiving area 224) may connect to any number of branch portions, which may channels that branch to a particular metering chamber 240. In one embodiment, two or more branch portions are provided. In an embodiment, such as shown in FIG. 18, branch portions may extend to one or more of the valve array zones 230 (on either side of the centerline A-A), for example. Also connected to valve array zones 230 in FIG. 18, via delivery channels, are reagent sections 260. The reagent sections 260 may be designed to receive a reagent therein. In one embodiment, these sections 260 are provided in the housing of the sample processing card 210 in the form of substantially rounded or circular well that receives and contains a volume of reagent therein. The reagent may be in the form of a liquid, fluid, or solution, that is metered from each of the sections 260 through delivery channels via activating valves/controllers, such that it is combined with the separated plasma from the blood sample, described later below. A volume of reagent may be injected into (via a user or the cartridge reader unit 100), pre-loaded, or stored in the reagent sections 260 in the sample processing card 210. In one embodiment, the reagent may be stored in the sections 260 of the sample processing card 210 using a blister pack configuration, i.e., the reagent is contained in the card and a seal is broken when testing of a sample takes place. In another embodiment, the reagent may be injected into the sections 260 and temporarily stored in the well/section until the valves/controllers are activated. Similarly, optional blister packs 265, wells, and/or storage chambers may be provided on the card 210 to introduce materials such as reagents, wash buffers, magnetic nano particles, bead solution, or other buffers to the separated test sample during processing. Such blister packs 265 and/or storage chambers 285 may be designed to store and/or hold any number of items used in a preparing a sample, including, for example, enzymes, beads, etc. Storage chamber 285 may also or alternatively be designed to store or capture a portion of a sample, including, for example, capturing beads.

In addition to selectively moving the test sample, then, the valves in valve array zone 230 (along with pneumatic system 330 connected to ports 235 and/or valve control ports 535) may further control delivery and mobility of the reagent, buffer, beads, etc. in the sample processing card 210, i.e., into the fluid metering chambers 240.

The reagent or reagent solution may be one including magnetic nanoparticles to label target proteins. Generally, the reagent or reagent solution is configured to include an antibody that causes a mechanical reaction. In some embodiments, a sample is contacted with one or more suitable cell lysis reagents. Lysis reagents are often configured to lyse whole cells, and/or separate nucleic acids from contaminants (e.g., proteins, carbohydrates and fatty acids). Non-limiting examples of cell lysis reagents include detergents, hypotonic solutions, high salt solutions, alkaline solutions, organic solvents (e.g., phenol, chloroform), chaotropic salts, enzymes, the like, or combination thereof. Any suitable lysis procedure can be utilized for a method described herein. One or more wash buffers may be utilized to immobilize antibodies on a sensor surface and/or block ions, amplification, etc. on the sensor. Such types of reagents and buffers are known by one of ordinary skill in the art and thus all are not listed in detail here. The term "nucleic acid" refers deoxyribonucleic acid (DNA, e.g., complementary DNA (cDNA), genomic DNA (gDNA) and the like) and/or ribonucleic acid (RNA, e.g., mRNA, short inhibitory RNA (siRNA)), DNA or RNA analogs (e.g., containing base analogs, sugar analogs and/or a non-native backbone and the like), RNA/DNA hybrids and polyamide nucleic acids (PNAs), the like and combinations thereof. Nucleic acids can be single- or double-stranded. In some embodiments, a nucleic acid is a primer.

The fluid metering chambers 240 may be positioned beneath (in the Y-direction) the sample injection zone 10 in the card 210. In an embodiment, the fluid metering chambers 240 may be connected to channels (e.g., branch channels) that extend from receiving area 224, valve array zone 230, and/or any number of reagent, blister packs, and storage chambers, 260, 265, and 285, respectively. For example, in accordance with embodiments herein, each fluid metering chamber 240 may be configured to extend between the valve array zone 230 and a corresponding gas permeable membrane 245 in the longitudinal direction. Each of the chambers 240 (four are shown in FIG. 18) may be positioned at a depth within the housing, between the top and bottom surfaces 218 and 222, and in a manner such that they are parallel to one another in a lateral direction of the housing and extend a length in the longitudinal direction relative to the centerline A-A. Each chamber 240 is sized to receive metered fluids—e.g., a volume of separated test sample (plasma) and a volume of a mixing material (e.g., reagent, buffer, beads from a mixing material source, such as a blister pack, storage chamber, etc.)—therein, such that they may be mixed and used for testing (e.g., biomarker sensing, analyte sensing) via GMR sensor chip 280. As described in greater detail below, an open state for some of the valves allows for both the patient (plasma) sample and mixing materials(s) to separately be pulled into the fluid metering chambers 240 until the fluid(s) reach the gas permeable membranes 245. In accordance with an embodiment, the structural design of the channels in the sample processing card 210 and mixing material(s) may be mixed from dry powder, liquid mixture, gel, or other mixture. Each chamber 240 may be further configured to output the received fluids through connected channels, e.g., based on the output of the pneumatic system 330.

Figure 24:
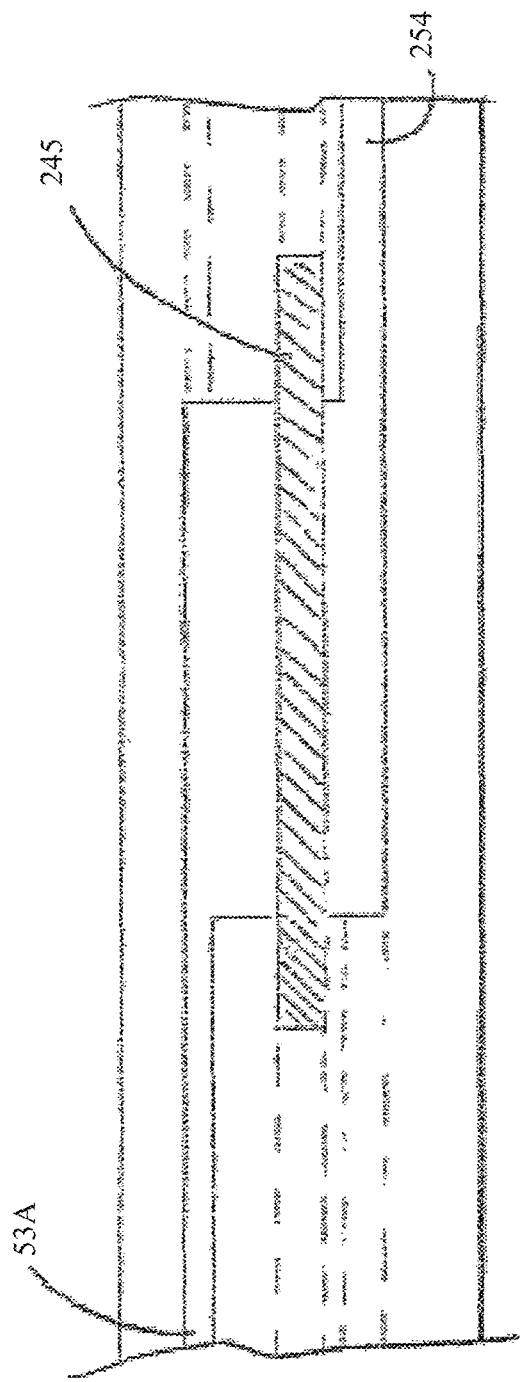
FIG. 24 shows a cross-sectional view of the sample processing card of FIG. 18 in accordance with an embodiment.
Figure 25:
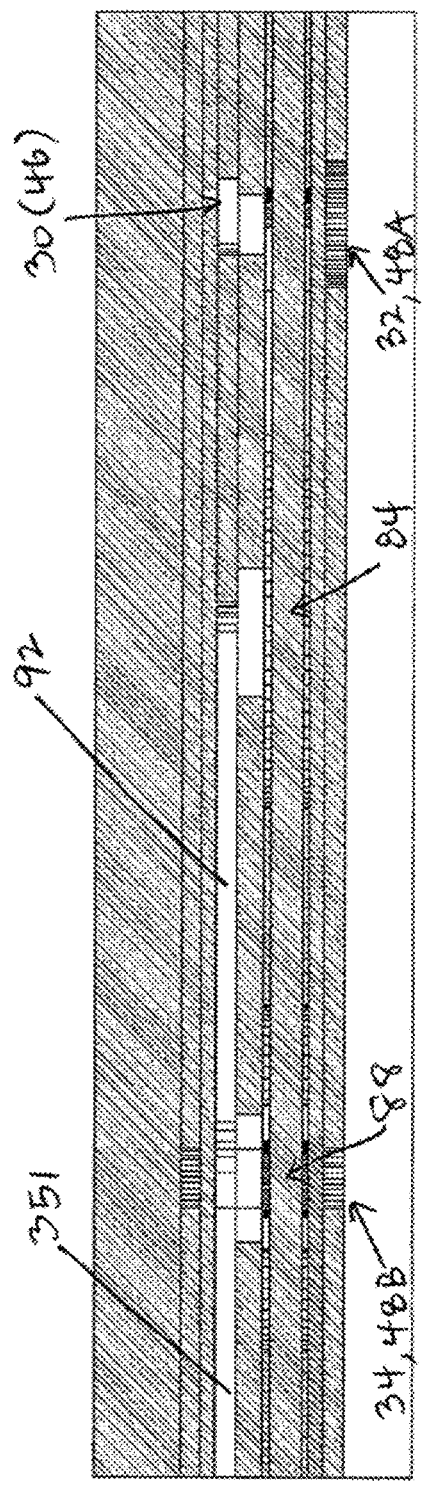
FIG. 25 shows a cross-sectional view of the valve array in the sample processing card of FIG. 18, in accordance with an embodiment.

The gas permeable membranes 245 are provided at a depth within the housing, such as shown in the cross section of FIG. 24. The gas permeable membranes 245 may be provided adjacent to and below the depth of the metering chambers 240 (e.g., in a layer below) in accordance with an embodiment. The gas permeable membranes may be fluidly connected to metering chamber(s). Each gas permeable membrane 245 may receive and deliver atmospheric air into the housing. The gas permeable membranes 245 may be formed from a membrane or material that is configured to receive, pull, or deliver atmospheric air into the housing of the sample processing card 210 while also being configured to prevent fluid(s) from entering into communication channels that are connected to pneumatic control ports 235. In an embodiment, the membranes 245 are used to pull air to a certain pressure through and into chambers 240. More specifically, a pump (fluidly connected to cartridge assembly 200) may be configured to generate negative pressure (vacuum) to pull fluids through a card 210, e.g., from metering chamber(s) 240 towards and to the gas permeable membrane(s) 245, which may also include pulling air through said membranes 245 (in addition to pulling through a communication channel connecting the metering chamber 240 and the gas permeable membrane 245). In an embodiment, the pump may be configured to stop application of negative pressure once the test sample/fluids/solution hits a gas permeable membrane(s) 245. In an embodiment, when the fluids reach the gas-permeable membranes 245, it may be determined in any number of ways, e.g., it may be sensed using a detector, determined based on a known volume of the chambers 240, and/or based on a predetermined amount of time for applying negative pressure (suction or vacuum) to the fluid chambers 240 (e.g., through a connected and corresponding communication channel) for metering the fluids. The gas-permeable membrane 245 may be provided in the form of a piece of adhesive film that is sandwiched between layers and provided in a pocket, for example. Fluid may be pulled to the top surface until it is whetted, providing the hard stop for the fluids pulled into the chambers 240.

Extending from the gas-permeable membrane 245 may be communication channels 254 that are connected to a pump interface, i.e., pneumatic control ports 235. In accordance with an embodiment, the communication channels 254 may be provided at a depth within the housing that is below the GPMs 245 and metering chambers 240 (see, e.g., FIG. 24).

As schematically depicted in FIG. 3, the pneumatic control (pump) interface includes a number of pneumatic control ports 235 that connect to one or more pumps or valves in a pneumatic system 330 (provided offline of the cartridge assembly 200, and thus the card 210, and within the cartridge reader unit 100). In the general context, each of the pneumatic control ports 235 are associated with a pressure switch. The supply to each of the pneumatic control ports 235 may be controlled or switched to apply positive pressure or negative pressure (suction or vacuum) to the ports 235, or no pressure at all, and thus apply such pressure the fluid metering chambers 240 and communication channels (e.g., like channel 433) in the card 210. In embodiments, the pneumatic control ports 235 and/or separate valve control ports 535 may be provided to control a position of valves in the valve array zone 230. Based on the position and switching of the pump(s) and valves therein, then, fluids may be moved throughout the sample processing card 210, and mixed and delivered to the sensing device (GMR sensor chip 280). Such details are explained throughout and later.

Turning back to the valve array zones 230, in accordance with an embodiment, each valve array zone 230 may comprise a first set 80 of valves and a second set 82 of valves. As shown in greater detail in FIG. 21, the first set 80 of valves may be provided in first (e.g., upper) row and the second set 82 of valves may be provided in a second (lower) row in the valve array zone 230. The valves in both sets 80, 82 may be controlled using a valve actuation interface 530 (or controller interface). The sets 80 and 82 may be formed in the elastomeric material 212, e.g., via laser cutting or molding, for example, in the form of elastomeric deflection portions (see, e.g., FIGS. 19 and 20, for examples of such deflection portions). Although the sets 80 and 82 are shown in the embodiment of FIG. 18 to include two valves each that are positioned as part of an array 230 on either side of a longitudinal axis or centerline A-A (e.g., four valves for each set, i.e., a total of eight valves), it should be noted that, in other embodiments, the valve array zone 230 may include a series of valves, wherein the sets 80, 82 arranged in rows laterally across the card 210. In one embodiment, a single valve for each set may be provided (i.e., a total of four valves). Additionally, the use of the term "set" is not intended to be limiting to the same type of valve. In an embodiment, a first valve 80 and a second valve 82 may be referred to as a "set."

Figure 21:
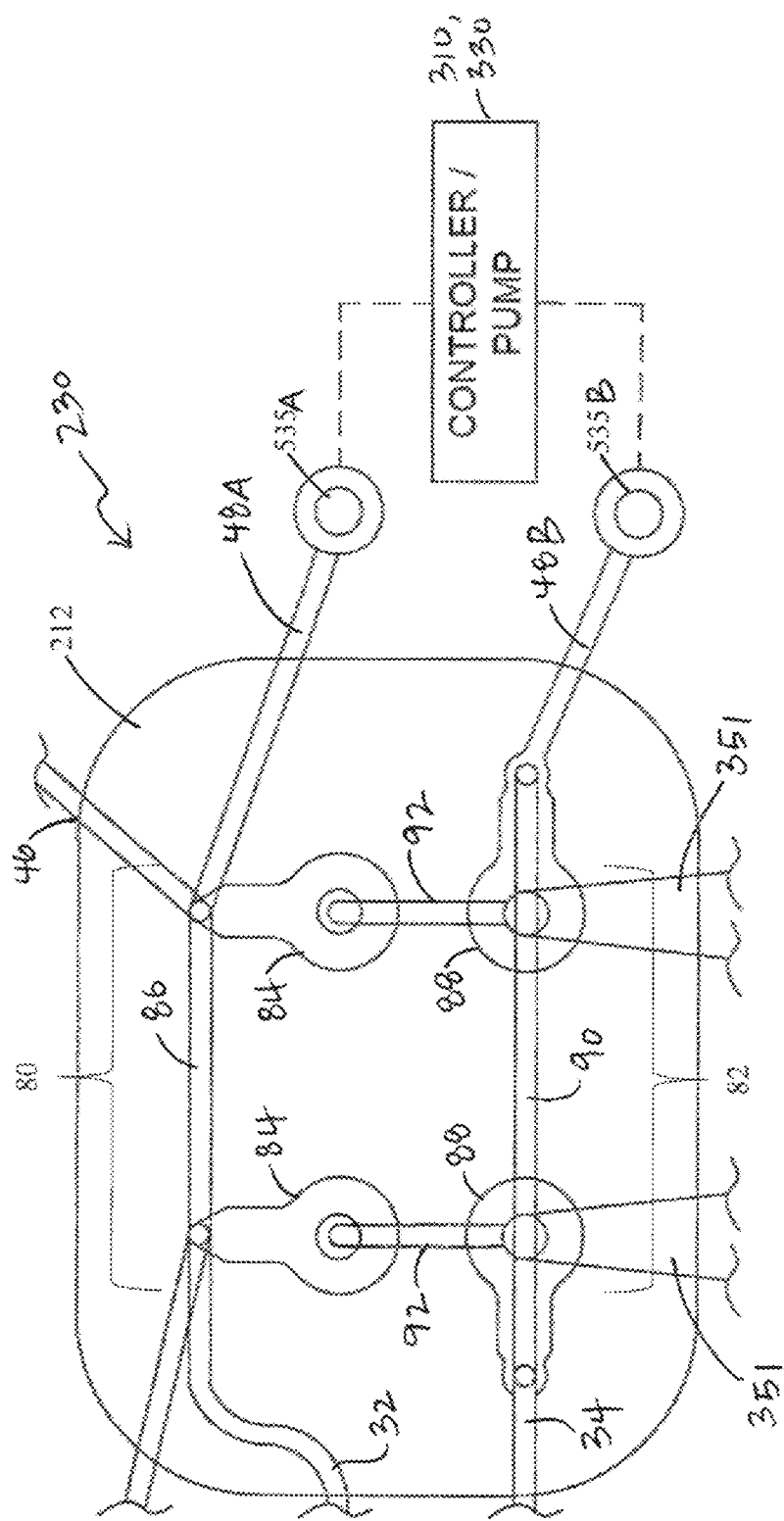
FIG. 21 is a detailed view of an exemplary valve array provided in the sample processing card of FIG. 18, in accordance with an embodiment.

The valve actuation interface 530 includes ports and control channels for selectively opening and closing the sets of valves in the valve array zone 230. Specifically, FIG. 21 shows a detailed view of one embodiment of the valve array zone 230 provided on the right side of the sample processing card 210A in FIG. 18, with valve actuation interface 530 connected thereto. However, it should be understood that the valve array zone 230 on the left side of the sample processing card 210A in FIG. 18 is substantially a mirror image of the valves on the right side, as depicted by the use of similar reference numerals in the drawings. Additionally, the location of the valve actuation interface 530 is not limited to what is illustrated in the drawings. In one embodiment, the valve actuation interface 530 may be provided on an opposite (left) side of the sample processing card 210A. In another embodiment, the valve actuation interface 530 may be provided on both sides of the sample processing card 210. In yet another embodiment, for example, the valve actuation interface 530 may be provided at a front end of the card 210, on either the top surface 218 and/or the bottom surface 222 of the housing, and adjacent to pneumatic control ports 235. Of course in still yet another embodiment, pneumatic control ports 235 may be utilized (along with connected channels) as the valve actuation interface 530.

The first set 80 of valves may include a series, a row, or a number of valves 84 (e.g., two or more) that may be fluidly connected together via first channel 86, in accordance with an embodiment. This first channel 86 may also be connected to one of the branch portions for fluid communication therewith (i.e., to receive separated plasma). In another embodiment, a branch portion may be directly connected to a pocket associated with the valve 84. The second set 82 of valves may include a series, a row, or a number of valves 88 (e.g., two or more) that are fluidly connected together via second channel 90, in accordance with an embodiment. Additionally, as seen in FIG. 21, for example, a connecting channel 32 may extend (laterally) between valves of the first set 80 (e.g., on either side of the centerline A-A) to communicatively and fluidly connect the valves 84 on the two sides. Connecting channel 32 may deliver pressurized air to each valve 84 provided in the sample processing card 210, for example. Similarly, a connecting channel 34 may extend (laterally) between the second sets 82 of valves for communicatively and fluidly connecting the valves 88 of the second set 82 (e.g., on either side of the centerline A-A). Connecting channel(s) 34 may also allow communication between metering chambers 240 and mixing channels 250, when valves 88 are in an open state. Connecting channel(s) 34 may be in fluid communication with second channel 90 and metering chamber 240 via transition sections 351, as noted below. Further, mixing channels 250 may be provided laterally between valves and fluid metering channels 240, in accordance with one embodiment. As shown in the exemplary view of FIG. 18, for example, the metering channels 240 connect to the valves in valve array zone 230 via transition sections 351 that are connected to or part of the metering channels 240. Of course, transition sections 351 may be used on the other side of the metering channels 240, as shown, or with any other feature in the card 210 (as described below).

As seen in FIG. 21, in accordance with an embodiment, also connected to first channel 86 may be a control channel 48A. Control channel 48A is connected to a control port 535A of the valve actuation interface 530. Connected to second channel 90 may be a control channel 48B that is connected to a control port 535B in the valve actuation interface 530. The control ports 42A, 42B of the valve actuation interface 530 are connected to one or more offline pumps or controllers (of pneumatic system 330, schematically depicted in FIG. 3) that are designed to open and close each of the valves 84 and/or 88, as needed, during processing of a test sample.

In accordance with an embodiment, the opening and closing of each of these valves 84, 88 is mediated by use of positive and negative pressure gradients generated offline using the controller(s) and a connection to the ports (ports 235 or ports 535 of the valve actuation interface 530). Again, in one embodiment, each of the valves 84 and 88 may be formed from a flexible elastomer or deflection portion that, based on an amount of force or pressure applied thereto, moves a state of each valve between its open and closed positions, shown in FIGS. 19 and 20. In accordance with an embodiment, each valve 84 and 88 may be configured to be in a normally open state or open position, at rest. Upon application of an amount of pressure (e.g., pressurized air), the noted valve may be moved to a closed position.

Figure 22:
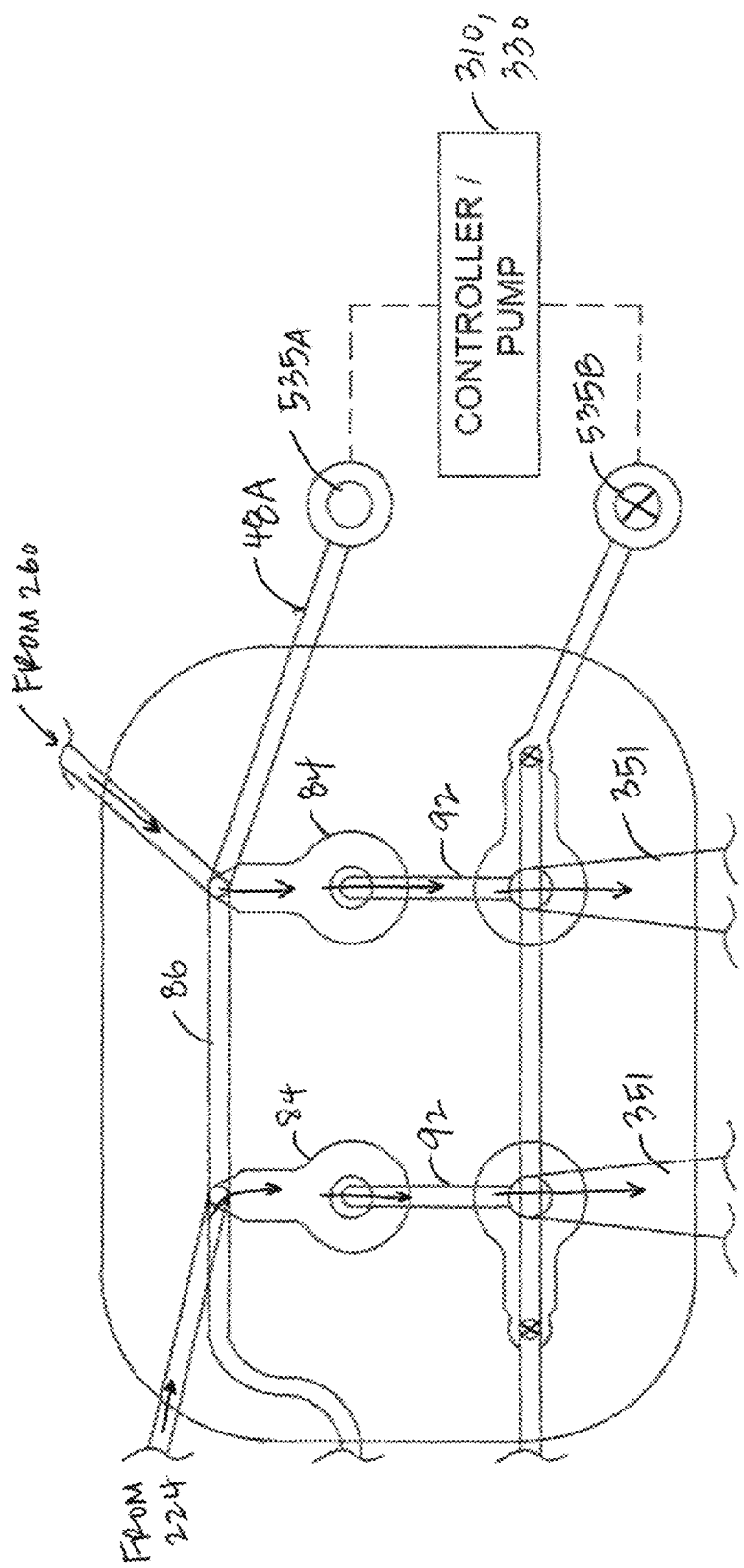
FIG. 22 is a detailed view of the valve array showing flow within channels in the first state, in accordance with an embodiment.
Figure 23:
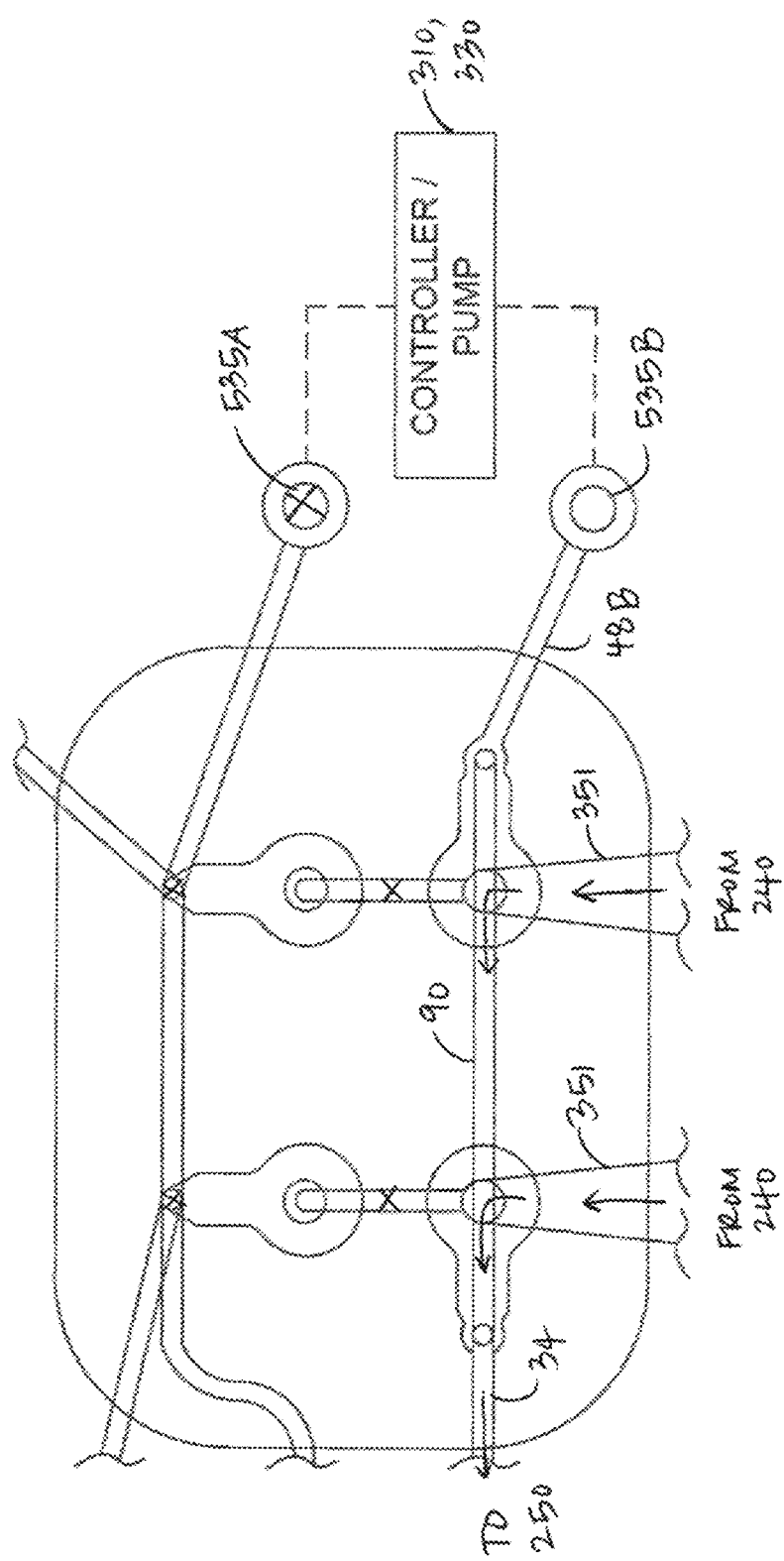
FIG. 23 is a detailed view of the valve array showing flow within channels in the second state, in accordance with an embodiment.

As shown in FIGS. 19 and 20, each of the channels connecting to the valves 84, 88 is positioned at a depth within the body or housing of the sample processing card 210. In an embodiment, the channels are formed within layers of the housing as it is manufactured. The positioning of the channels at different depths allows fluid to flow therethrough without interfering with other parts of the housing. For example, FIGS. 19 and 20 show a cross section taken in the valve array zone 230, showing the connection and positioning of the aforementioned channels (e.g., 92, 48A, 48B), and valves 84, 88 and their positioning within the housing (some of the lines illustrate exemplary layers that may be used to form the housing). The depths at which channels and valves are illustrated are exemplary only. Based on the state of the valves, the channels may be connected or blocked. That is, flow through the channels may be controlled based on movement of the elastomeric deflection portions relative to the channels, as activated by application of pressure via interface 530. For example, as shown in FIG. 19, in a first state, each valve 84 may be open, while valve 88 is closed (e.g., via pressurized air being applied to control channel 48B). Such features are represented here by arcs, to illustrate that the open valve 84 allows for fluid communication from and in communication channels, through valve 84 and channel 92, and into fluid metering chamber 240 via transition section 351. Fluid flow is blocked from delivery through valve 88 and into mixing channel 250. FIG. 22 schematically illustrates, for example, the movement of fluid in the first state of FIG. 19. In a second state, shown in FIG. 20, each valve 88 may be open, while valve 84 is closed (e.g., via pressurized air being applied to control channel 48A). Again, the positioning of the arcs illustrates that the open valve 88 allows for fluid communication from metering chamber 240 via transition section 351, through valve 88 and channel 90, and into mixing channel 250 (e.g., channel having a stepped configuration and connected to output ports 255). Fluid flow is blocked from delivery through valve 84 and through other communication channels. FIG. 23 schematically illustrates, for example, the movement of fluid in the second state of FIG. 20. As such, in accordance with an embodiment such as the one depicted in FIGS. 18 and 21, when each valve 88 is closed, fluid(s) may be directed towards fluid metering chambers 240. When each valve 88 is open, fluid may be directed towards mixing channels 250.

Alternatively, in accordance with another embodiment, the individual valves 84, 88 in each set 80, 82 may be individually controlled such that movement of fluid and/or materials may be directed through a specific area and one or more microfluidic communication channels, e.g., to a particular metering chamber 240. That is, fluid/materials may move through only certain channels and areas in the card, and do not necessarily need to move through all valves in a set or array zone.

In one embodiment, the amount of pressure/pressurized air applied to the interface 530 to move valve(s) 84, 88 between their open and closed positions may be within a range of approximately 2.0 psi to approximately 10.0 psi. In one embodiment, approximately 5.0 psi may be applied to the interface 42 to move the valve(s) between positions, i.e., from an open state to a closed state. Generally, the required amount of pressure for setting the state of the valves is small.

Referring now to the other pneumatic features of the card 210, in an embodiment, connected to each metering chamber 240, e.g., via a connected, microfluid communication channel, may be one of the pneumatic control ports 235 that are configured to selectively draw and deliver pressurized fluid to (into) and from the housing. In another embodiment, each pneumatic control port 235 may connect (via connecting channels) to more than one metering chamber 240. The pneumatic control ports 235 may be a part of a pump interface that is provided in a lower portion (front end 205) of the body/housing, for example, such as shown in FIG. 18. The pneumatic control ports 235 may be positioned relative to and accessed via the top surface 218, the bottom surface 222, or a combination thereof. In another embodiment, the ports 235 may be positioned on a side of the card 210. Generally, the pneumatic control ports 235 and the pneumatic control interface are shown as being provided in a top surface 218 of the card 210, but such is for explanatory purposes only and not intended to be limiting.

The pneumatic system 330 of cartridge reader unit 100 is configured to be connected to the ports 235 at this interface, when the card 210 is inserted therein. In an embodiment, the pneumatic system 330 includes a pump that may be a different pump or a similar pump connected at the valve actuation interface 530. The pneumatic control ports 235 may be used to move and mix fluids throughout the channels in the housing of card 210. Depending on the state (open or closed) of the valves and the pump(s) connected at pneumatic control ports 235, the mixing channels 250 may allow for either or both of the test sample (plasma) and mixing materials(s) from a mixing material source to be pulled into fluid metering chambers 240 and/or pushed from said metering chambers 240 into mixing channels 250. Negative (suction or vacuum) pressure may be applied by pump to the pneumatic control ports 235, and/or to the valve control ports 535, may be configured to draw fluids (plasma, reagent) through the valves in valve array zone(s) 230, for example. Positive pressure (e.g., in the form of a pressurized fluid such as pressurized air) may be applied to pneumatic control ports 235, and/or to the valve control ports 535, to deliver fluids from the metering chamber(s) 240 to mixing channels 250, for example.

In accordance with an embodiment, as described above, in some embodiments, the fluid metering chambers 240 may also be fluidly connected to the second channel 90 via a transition section 351 provided at its top end, for example. In accordance with an embodiment, a corresponding transition section 351, may also be provided at a bottom end of each fluid metering chamber 240 near each gas permeable membrane 245. Transition sections 351 may be formed such that its width expands from a reduced width (near the valve array zone 230) to a width similar to that of the top/entrance of the chamber 240, and reduces in its width from the bottom/exit of the chamber 240 to a reduced width at its relative fluid line. The size and shape of the transition sections 351 are formed in this manner in order to reduce and/or prevent air bubbles from forming in the chambers 240. They further assist in providing smoother fluid flow when fluid is moved through the chamber 240.

Moreover, as shown throughout the Figures, transition sections 351 may be associated with other features in a sample processing card 210, including blister packs 265 and/or storage chambers 285, for example. Again, these transition sections 351 assist in directing materials (wet or dry) from a first feature to a second feature, thereby assisting in providing a smoother flow as material is moved within channels/areas of the card 210.

FIG. 18 shows the above-mentioned mixing channels 250 in greater detail, in accordance with an embodiment. Each of these mixing channels 250 may be used, in accordance with an embodiment, to mix, or, more specifically, further mix the metered test (plasma) sample and mixing material(s) that may be drawn into the chambers 240, which will be further explained below. The mixing channels 250 may be designed to mix or further mix the test sample and mixing material(s) into a substantially homogeneous or homogeneous mixture, for output and use in testing via GMR sensor chip 280. The mixing channels 250 may be provided such that they extend longitudinally (along Y-Y) within the body of the card 210, in accordance with an embodiment. Each of the mixing channels 250 may be connected at a first (input) end to a connecting channel and to another part in the card 210, e.g., a sensor delivery output port 255, at a second (output end), in accordance with an embodiment. The mixing channels 250 may be selectively connected to metering chambers, for example, and configured to deliver (by way of connected communication channels) a homogeneous mixture and/or a test sample and other mixing materials to the GMR sensor chip 280 via output port 255.

In accordance with the exemplary embodiment shown in FIG. 18, two mixing channels 250 are provided in the cards 210A and 210B at a depth (or layer) below the metering chambers 240. The positioning of each mixing channel 250 may be such that it is provided adjacent to or near a middle or centerline A-A thereof, in accordance with one embodiment. For example, as shown in FIG. 18, when two mixing channels 250 are provided, each channel may be provided on an opposite side of the longitudinal axis or centerline A-A, in accordance with an embodiment. In one embodiment, the mixing channels 250 may run generally parallel to one another on either side of the centerline A-A. In another embodiment, the mixing channels 250 may be offset from one another on either side of the centerline A-A. In yet another embodiment, mixing channels 250 may be provided on the same side of a centerline A-A (e.g., on a right side) of a sample processing card 210. In yet another embodiment, the one or more mixing channel(s) 250 in a sample processing card 210 may extend diagonally, laterally, or at an angle relative to the centerline A-A. One mixing channel 250 may be associated with more than one metering chamber 240, e.g., two chambers, in accordance with an embodiment.

In accordance with an embodiment, each of the mixing channels 250 may have a stepped configuration between its ends that includes portions that extend longitudinally (or vertically, or in the Y-direction) and portions that extend laterally (or horizontally, or in the X-direction) in the housing of the sample processing card 210. This stepped configuration enables the fluids to be moved through planes and induce turbulence in the fluids via its bends, to thereby blend and/or mix the fluids thoroughly into a substantially homogeneous or homogeneous mixture. In another embodiment, the mixing channel(s) 250 may include a zig-zag type configuration.

One or more output ports 255—also referred to as a sensor delivery port—is provided to output a prepared sample (e.g., a test sample mixed with mixing material in metering chamber 240) from the card 210 to a GMR sensor chip 280, as discussed below. Each of the ports 255 may be positioned at a depth within the card 210 and connected via a channel to another feature of the card, e.g., such that a test sample is directed from a metering chamber 240 and/or mixing channel 250, and towards bottom surface 222, where the GMR sensor chip 280 is located, in accordance with an embodiment. In an embodiment, the port(s) 255 may be provided in a lower portion of the card 210, e.g., at a front area (205) as shown in FIG. 18, for example. In another embodiment, the port(s) 255 may be provided in a center of a card 210. The ports 255 may be positioned relative to and accessed via the top surface 218, the bottom surface 222, or a combination thereof. In another embodiment, the ports 255 may be positioned on a side of the housing. In one embodiment, the sensor delivery ports 255 may be configured to output the fluid mixture through the bottom surface 222 of the card, and thus the ports 255 may be associated with or positioned adjacent to a sensor provided underneath the card 210. The ports 255 may be positioned on a location of the sample processing card 210 that cooperates and meets an inlet(s) of sensor(s) on such a device, so that the sensor(s) can detect and produce an output reading from the substantially homogeneous mixture that is output from the housing. The location of the ports 255 is not intended to be limiting. Generally, as previously described, the location of the port(s) 255 may depend upon the location of the GMR sensor chip(s) 280 provided as part of the cartridge assembly 200. For example, if multiple GMR sensor chips 280 are provided, multiple ports 255 may be positioned adjacent to the chips 280. Output delivery via ports 255 is controlled using the valves 84, 88, pneumatic control ports 235, optional valve control ports 535, controller(s)/cartridge reader 310, and/or pump(s) and valve(s) of the pneumatic system 330.

In another embodiment, the sensor delivery ports 255 may be configured to output the fluid mixture through the top surface 218 of the card, and thus the ports 255 may be associated with or positioned adjacent to a sensor provided above the sample processing card 210. For example, the sensor(s) may be provided on a handheld mechanism or system.

One or more internal waste chambers (also referred to herein as waste tanks or waste reservoirs) 270 may also be optionally provided on the card 210 to store waste from the test sample. For example, after a test sample is mixed with mixing material(s) in the metering chambers and directed to GMR sensor chip 280 (e.g., to flow over the chip 280 and/or through output ports 255 to the chip 280), it may be directed to and deposited into one or more of the waste chambers 270 provided in the card 210 (e.g., by directing the test sample through an input port 257 and/or channel(s) connected to the waste chamber(s) 270). Each of the waste chambers 270 may be positioned at a depth within the housing, between the top and bottom surfaces 218 and 222. In an embodiment, the waste chambers 270 may be positioned in a manner such that they are parallel to one another in a lateral direction of the housing and extend a length in the longitudinal direction relative to the centerline A-A. In another embodiment, the waste chambers 270 may be positioned at an angle relative to centerline A-A. In an embodiment, the waste chambers 270 are positioned in a layer or at a depth that is below the metering chambers 240 within the sample processing card 210. Channels may connect the metering chambers 240 to the output ports 255 to the GMR sensor chip 280, as well as connect input port 257 from GMR sensor chip 280 to the waste chambers 270. The fluid of the test sample may be removed to waste reservoirs 270 by applying negative pressure through pneumatic control ports 235 (through a connected (to pneumatic system 330) and corresponding communication channel), for example.

In some embodiments, a serpentine channel may be provided in the sample processing card 210 of the cartridge assembly 200. The serpentine channel may be used as part of a thermocycling and/or an amplification process of the test sample within the card 210.

The sample processing card 210 and/or cartridge assembly 200 may further include one or more alignment devices 295 therein, in accordance with an embodiment. In one embodiment, such as illustrated throughout the Figures, the alignment devices are provided in the form of alignment holes 295. In another embodiment, the alignment devices 295 may be provided in the form of protrusions or pins extending from the card 210 and/or assembly 200. The alignment devices 295 may be used to align the cartridge components during assembly of the card 210 (e.g., during assembly of its layers) and/or for seating and aligning the cartridge assembly 200 into and within the cartridge receiver 130 (e.g., into the receiving tray) of the cartridge reader unit 100. Alternatively, other structural features, such as cut-out portions or divots, for example, may be provided as alignment devices on the cartridge assembly 200. In another embodiment, a structural alignment device, such as a card stop wall or protrusion, may be provided inside of the cartridge reader unit 100 to act as an alignment device.

In accordance with an embodiment, the disclosed sample processing card 210 is configured for use as part of the cartridge assembly 200 which is provided for use in cartridge reader unit 100 and designed to provide technicians with convenient and fast analyte detection in a single process. The device may detect a level of analyte within an input blood sample, for example. In one embodiment, the system or device may be a handheld or mobile device or system configured to connect with or receive the cartridge assembly 200. For example, the card 210 may interface with a handheld system via a face seal using o-rings that are clamped down to the top of the card. This seal permits a negative pressure to be achieved that facilitates fluid movement throughout the card, as described with reference to FIG. 26 and method 600A, in accordance with one embodiment. The mixture from sample processing card 210 may be output (or input) into the GMR sensor chip(s) 280 of cartridge assembly 200, and the presence of multiple biomarkers may be detected by capturing proteins from the mixture and quantifying their presence based on magnetic field detection. In an embodiment, the cartridge assembly 200 may employ one or more sensors configured to detect analytes in a mixture/sample by displacing competing analytes labeled with magnetic nanoparticles and sensing a change in the magnetic field created by the magnetic nanoparticles via a magnetic (field) sensor, e.g., a giant magnetoresistance (GMR) sensor chip 280 or other magnetic sensors (e.g., AMR, TMR, etc.). One or more sensors or an array of magnetic sensors may be formed on a chip, for example, so that multiple antigenic analytes are detected with specificity within the sample.

In an embodiment, the sample processing card 210 (in any of the embodiments disclosed herein) of a cartridge assembly 200 may be fabricated by stacking and laminating different types and layers of laser cut, polymer materials, to produce the described channel geometries and shapes shown in the Figures. In addition to these layers, the gas-permeable membrane 245, filtration membrane 220, and/or elastomer material 212 over zones 230 may also be laser cut and placed in designated regions of the sample processing card 210 to provide the required functionality. However, as noted throughout this disclosure, any number of manufacturing methods and/or materials may be used to manufacture the sample processing card 210.

Figure 26:
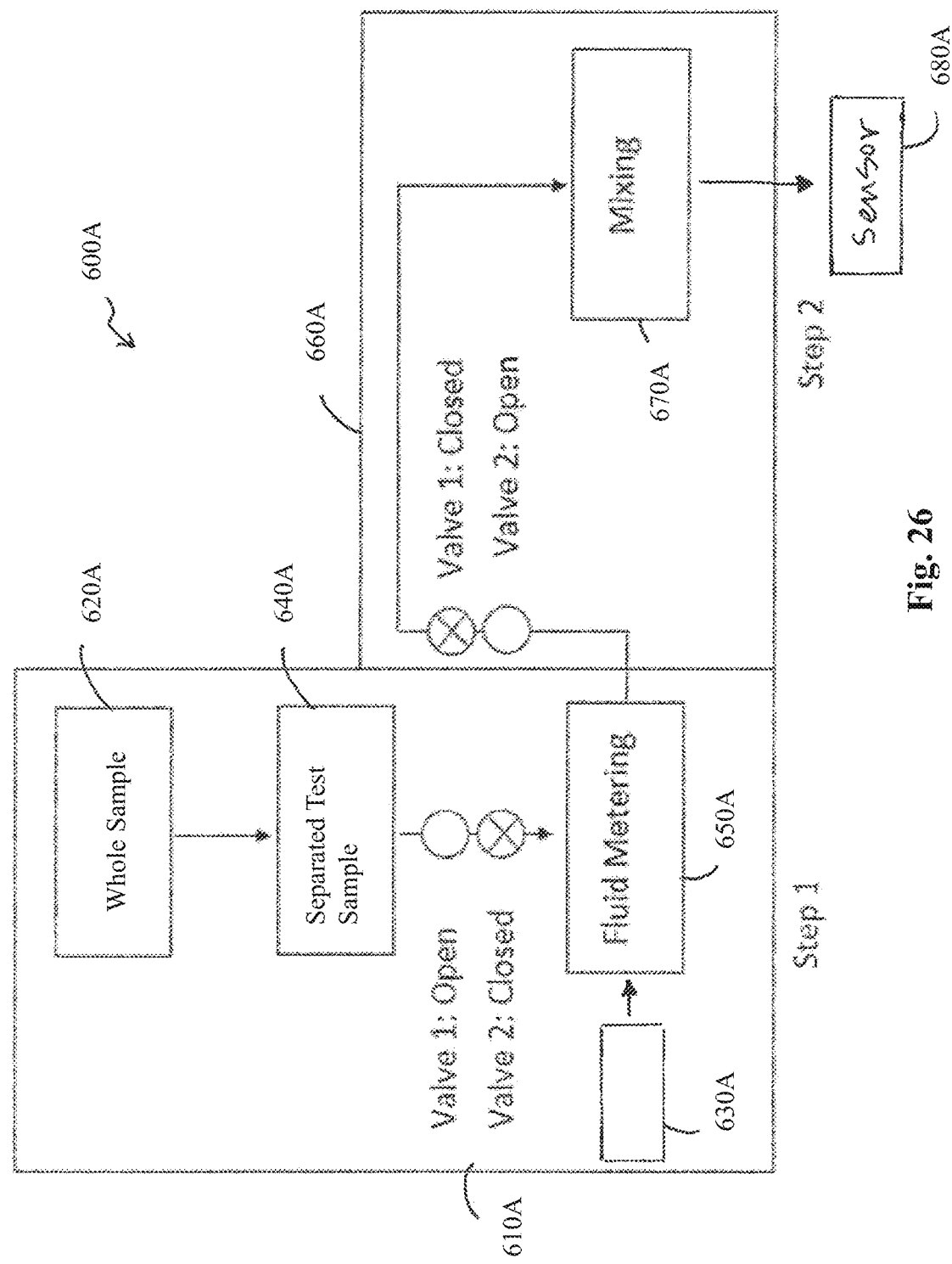
FIG. 26 is a flow chart of a method of using the sample processing card of FIG. 18 along with the cartridge reader unit, in accordance with embodiments herein.

FIG. 26 is a flow chart of a method 600A of using the cartridge assembly 200, e.g., with a handheld system or cartridge reader unit 100, or another offline device or system, that is configured to connect to the cartridge interfaces (e.g., including pump interface and pneumatic control ports 235, any valve control ports 535, and sensor output interface) and substrate 202. For explanatory purposes only, reference to a single controller and pump (as part of the pneumatic system 330) is noted here, but is not meant to be limiting. In an embodiment, in a first state, a first set 80 of valves, valves 84, are in an open position, while the second set 82 of valves, valves 88, are in a closed position. In a second state, the first set of valves (84) are in a closed position, while the second set of valves (88) are in an open position.

In accordance with an embodiment, the method 600A of using the herein disclosed cartridge assembly 200 to mix a test sample follows steps of method 200. The valve states of the valves 84 and 88 are initially set as follows, as shown at 610A: pump is attached to the valve interface (530, if provided, or pneumatic interface) and controlled and configured to apply positive pressure through valve interface via ports 42B and 48B to second channel 90, including through any connecting channels that may connect to valves on opposite side of the centerline A-A, such that valves 88 (Valve 2) are moved to a closed position. In an embodiment, no pressure is applied to first channel 86 and channel 32, and thus valves 84 (Valve 1) remain in an at rest/default state, i.e., an open position. In another embodiment, the pump may be controlled to position the valves 84 in an open state. A sample (which may be a whole sample) is input or injected at 620A, e.g., into the injection port 215 of the sample processing card 210 of the cartridge assembly 200. Reagent(s), wash buffer(s), beads, etc.—i.e., mixing material(s)—may be optionally stored in or provided to the sample processing card 210, as shown at 630A, and ready for mixing with the separated test sample, in accordance with one embodiment. As described in greater detail above, the mixing material(s) may be stored or added to the sample processing card 210, prior to the injection of the sample and/or after insertion of the cartridge assembly 200 into the unit 100. The test sample is (optionally) separated at 640A from the input whole sample, e.g., using filtration membrane 220. At the pump interface, a pump/pneumatic system 330 is also attached to the ports 235. Negative (suction or vacuum) pressure may be applied by pneumatic system 330 to the ports 235, thereby pulling the separated test sample and any mixing material(s) through the communication channels and/or into the fluid metering chambers 240, as shown at 650. For example, the vacuum pressure pulls the separated test sample and mixing material(s) from 260, 285 through branches or channels into metering chambers 240. This action may allow the two fluids to be forced into the mixing region in a 1:1 ratio. Alternatively, the fluids may be pushed and/or pulled at different times and at different ratios, depending upon the test being performed. Both fluids are metered or pulled until they reach the gas permeable membranes 245, for example.

After the metering at 650A, the valve states in the valve array zone(s) 230 are switched, as shown at 660A. The pressure from pump/pneumatic system 330 is reversed and controlled to apply positive pressure through valve actuation interface (530) (if provided, or alternatively, the pneumatic interface) via port 42A and control channel 48A to first channel 86, including through communication channels to other valves, e.g., on an opposite side of the centerline A-A, such that valves 84 (Valve 1) are moved to a closed position. In an embodiment, no pressure is applied to second channel 90 and connecting channel, and thus valves 88 (Valve 2) remain in an at rest/default state, i.e., an open position. In another embodiment, the pump may be controlled to position the valves 88 in an open state. The pump may also be controlled to apply positive pressure at the pump interface through ports 235, channels and gas permeable membranes 245, such that it moves or pushes the metered fluids (e.g., plasma and reagent) to and through second channels 90, and then into mixing channels 250. The continuous application of pressure through ports allows for mixing, as indicated at 670A, of the fluids as they move through (e.g., the stepped configuration of) the mixing channels 250, to form a substantially homogenous or homogeneous mixture, e.g., of the test sample and any mixing materials (reagent). The mixed fluids exit or are output from the sample processing card 210, e.g., via output ports 255, to one or more GMR sensor chips 280 that is/are part of the cartridge assembly 200, as represented at 680A. The sensor chip(s) 280 uses the mixed, homogeneous fluid to sense or detect a designated item, e.g., biomarkers, in the sample provided thereto.

At the end of the method, although not depicted in FIG. 26, the mixed fluid/sample may be directed to one or more waste chambers 270 provided in the sample processing card 210.

In an embodiment, the multiple biomarker reading from the GMR sensor chip(s) 280 may be performed and output (e.g., via the display 120) to the user.

Of course, while the description of method 600 may refer to valves 84 and 88 as being open or closed, this refers to one exemplary embodiment. That is, as previously described with reference to the valves, in some embodiments, individual valves may be controlled, e.g., in different stages, for moving fluid and/or materials through the card 210. Accordingly, reference to Valve 1 and Valve 2 in the method 600 is exemplary only, and not intended to limit the description of valves 84, 88 to mean that all valves in a set 80, 82 must be moved or changed at the same time.

In accordance with an embodiment, the total processing time from injection to output (out to sensor) of the method 200 may take approximately ten to twenty minutes, depending on the pump design and settings. However, the processing time may be altered and is not meant to be limiting.

In an embodiment, a test sample of approximately 500 mL or less of blood is configured to be injected into the injection port 215. In an embodiment, a test sample of approximately 300 mL of blood is configured to be injected into the injection port 215. In an embodiment, the filtration membrane 220 is configured to yield approximately 50 mL to approximately 250 mL of plasma. In an embodiment, the filtration membrane 220 is configured to yield approximately 100 mL of plasma.

In accordance with an embodiment, approximately 50-100 ml of reagent may be provided in the reagent injection sections and/or used in the sample processing card 210.

The herein disclosed sample processing card 210 uses interfaces, valves, and channels to allow for autonomous metering and mixture of (optionally stored on-board or provided thereto from unit 100) reagents with a patient blood sample that is input therein as part of a single application or process. The method 600 of using the disclosed microfluidics card 210 allows for a user to perform mixing of a sample as part of a single process, and analysis when used in conjunction with a device (sensor chip 280), so that multiple biomarkers features in the sample may be detected. The metering of the fluids and subsequent mixing operations are controlled entirely by off-cartridge pump(s) and controller(s) (pneumatic system 330 and cartridge reader 310, respectively) that are connected to the card 210 when the card 210 is inserted and connected to the cartridge reader unit 100, which allows for a complete automation of the assay process that previously required human technicians. The standardization of geometries and fluid movement also allows for a more stable platform, as more elements of the system are controlled.

Also, using this optionally disposable point of care cartridge assembly 200, a wider range of detection is possible while using a smaller amount of patient blood sample, without sacrificing speed in the production of results. For example, the disclosed assay cartridge assembly design permits the detection of multiple biomarkers from a single sample, and thus facilitates multiplex analysis of target biomarkers from a single patient sample. In a particular embodiment, the disclosed cartridge assembly 200 utilizes the patient blood sample for targeting multiple (e.g., five) biomarkers associated with cardiac distress.

Further, the structural features of the disclosed cartridge assembly 200 may permit multiple assays to run in parallel. Examples of such multiple assays are described below.

FIGS. 27-30 generally illustrate functional blocks of the cartridge reader 310 (control unit) and a signal processor within the cartridge reader unit 100, and processes associated therewith, that may be utilized and implemented by the cartridge reader unit 100 with regards to an inserted cartridge assembly 200. In an embodiment, the system 300 described herein may process signals at the GMR sensor as disclosed in International Patent App. No. PCT/US2019/043791, entitled "SYSTEM AND METHOD FOR PROCESSING ANALYTE SIGNALS IN GMR-BASED DETECTION OF BIOMARKERS and filed on the same day, which is hereby incorporated by reference herein in its entirety. For example, as noted above, at step 445, signals from the GMR sensor chip 280 are received and processed, e.g., via cartridge reader 310. In an embodiment, cartridge reader 310 is configured to perform the function of processing results from the GMR sensor chip 280 using a sample preparation control part having a memory reader unit and a sample preparation control unit (e.g., used to receive signals indicating that a cartridge assembly 200 has been inserted into the cartridge reader unit 100, read information stored in the memory chip 275, and generate pneumatic control signals and send them to the pneumatic system 330) and a signal processing part adapted to control electrical elements, prepare and collect signals, and process, display, store, and/or relay detection results to external systems, including processing measurements signals to obtain test results of the analyte detection, as described in detail in the PCT/US2019/043791 application. Additional features relating to the cartridge reader 310 and signal processor of the unit 100 are described below.

Figure 27:
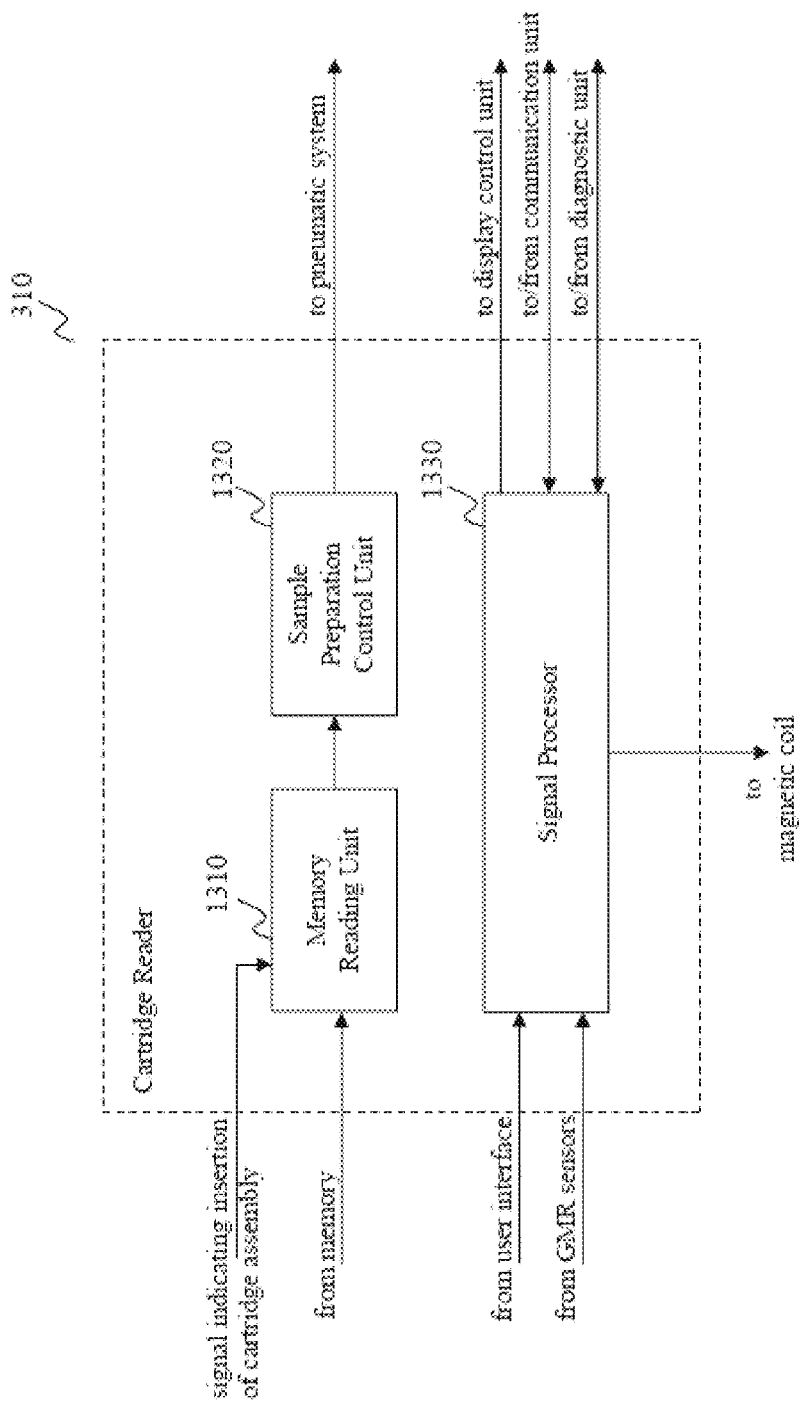
FIG. 27 schematically shows functional blocks of the cartridge reader in accordance with an embodiment of this disclosure.

FIG. 27 schematically shows functional blocks of the cartridge reader 310 in accordance with an embodiment. As shown in FIG. 27, the cartridge reader 310 may be divided roughly into a sample preparation control part and a signal processing part. A memory reading unit 1310 and a sample preparation control unit 1320 form the sample preparation control part. The memory reading unit 1310 may be adapted to, upon receipt of a signal indicating that a cartridge assembly 200 has been inserted into the cartridge reader 310, read information stored in the memory chip 275 on the cartridge assembly 200. The sample preparation control unit 1320 may be configured to, based on the information read from the memory chip 275, generate pneumatic control signals and send them to the pneumatic system 330. In some embodiments, when insertion of the cartridge assembly 200 into the cartridge reader 310 is recognized, an indication signal may be created by the cartridge assembly 200 and sent to the memory reading unit 1310 to inform of the insertion event. Alternatively, in other embodiments, such an indication signal may be created by other components at the cartridge reader 310 and sent to the memory reading unit 1310.

The signal processing function of the cartridge reader 310 is mainly performed by a signal processor 1330. The signal processor 1330 may be adapted to control electrical elements, prepare and collect signals, and process, display, store, and/or relay detection results to external systems. For example, the signal processor 1330 operates to generate a control signal for controlling the magnetic field generator 360, resulting in magnetic field excitation applied onto the GMR sensors in the cartridge assembly 200. In an embodiment, the signal processor 1330 operates to generate a control signal for controlling the second magnetic field generator 365, resulting in magnetic field excitation applied to a part (e.g., top, bottom, sides) of the sample processing card 210 of an assembly 200 during preparation and processing of a sample, e.g., when moving mixing material(s), such as a buffer and/or magnetic beads from a mixing material source, and test sample within the card. After receiving measurement signals from the GMR sensors in the cartridge assembly 200 and from at least one reference resistor disposed in the cartridge assembly 200 and/or the signal processor 1330, the signal processor 1330 processes the measurements signals to obtain test results of the analyte detection. Via the display control unit 120, the test results may be displayed on an integrated or external display. Moreover, the signal processor 1330 may be coupled to the user interface 140 for receiving instructions from the user. Additionally, in some embodiments, the signal processor 1330 may be coupled to the communication unit 340 and/or with the diagnostic unit 350, enabling evaluation and diagnosis from the test results alone or in combination with other externally available data.

Figure 28:
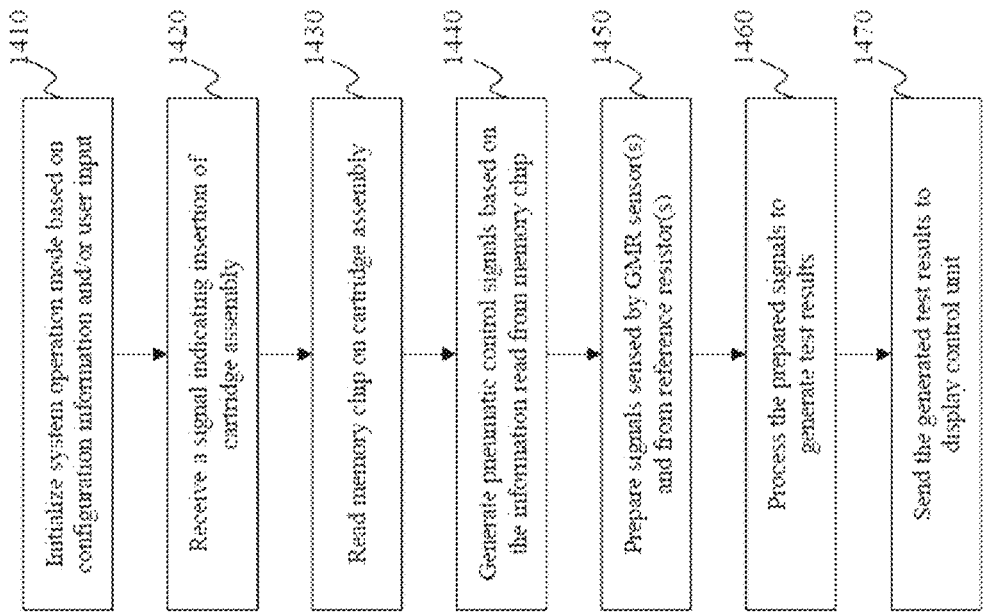
FIG. 28 is a flowchart of a process of the cartridge reader, in accordance with an embodiment of this disclosure.

FIG. 28 is a flowchart of the process of the cartridge reader 310 in accordance with an embodiment. As shown in FIG. 28, the cartridge reader 310 starts its operation at step 1410 by initializing an operation mode based on system configuration profile and/or instructions inputted by the user via the user interface 140. Then, the process waits at step 1420 for a signal indicating that a cartridge assembly 200 has been inserted into the cartridge reader 310. This signal may be created by either the cartridge assembly 200 or the cartridge reader 310 upon recognition of the insertion. In response to receiving such a signal, at step 1430, the cartridge reader 310 reads the memory chip 275 on the cartridge assembly 200. Then, at step 1440, the cartridge reader 310 generates control signals based on the read information, and sending them to the pneumatic system 330 for pneumatic control used in preparation of the sample to be tested. At step 1450, the cartridge reader 310 prepares measurement signals at the GMR sensors and at the at least one reference resistor and receives the signals. Then, at step 1460, the cartridge reader 310 processes the received measurement signals to generate test results. Finally, at step 1470, the cartridge reader 310 sends the generated test results to the display control unit 120 for display to the user.

Figure 29:
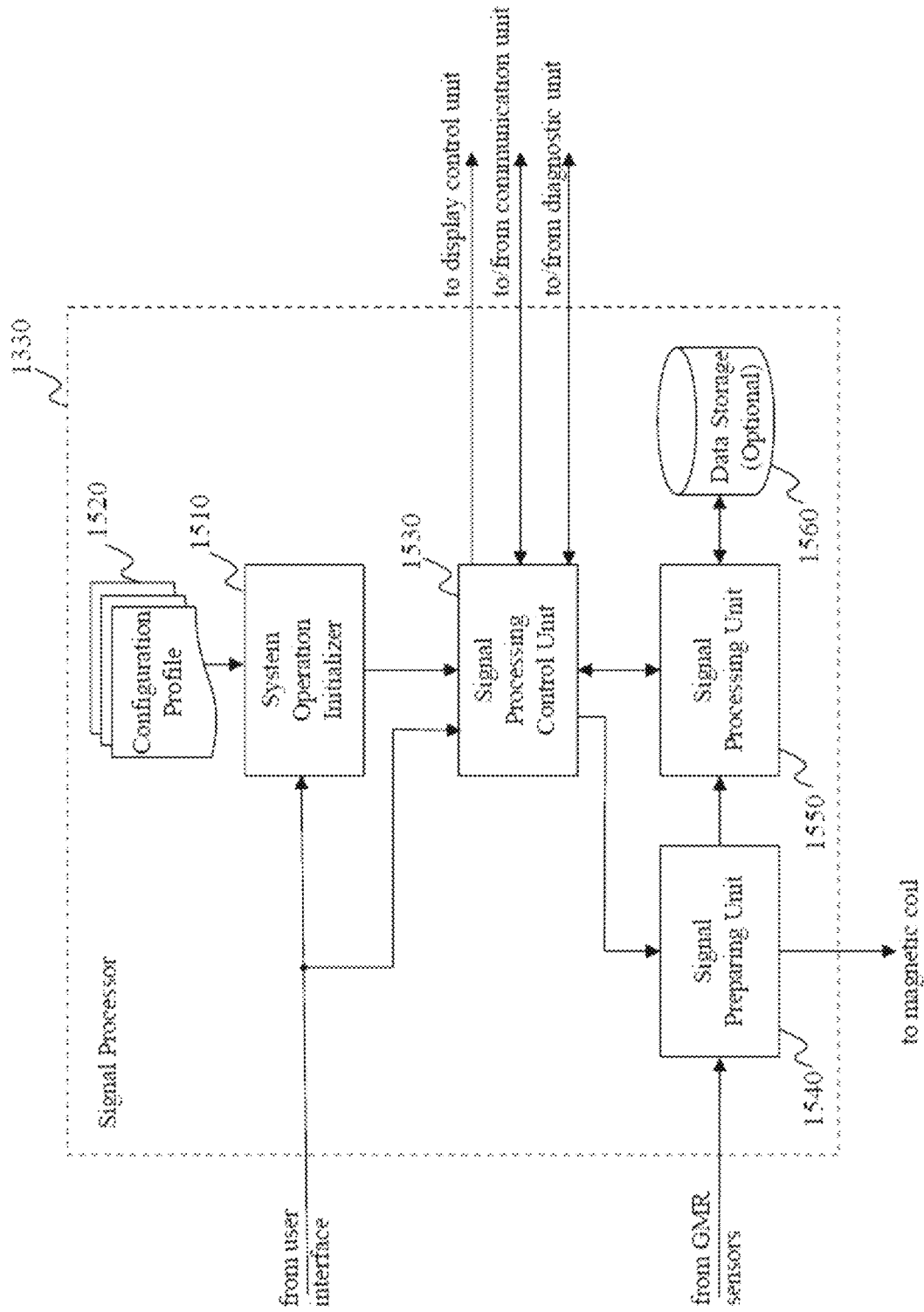
FIG. 29 schematically shows functional blocks of a signal processor, in accordance with an embodiment of this disclosure.

FIG. 29 schematically shows the functional blocks of the signal processor 1330 in accordance with an embodiment. As shown in FIG. 29, the signal processor 1330 may include a system operation initializer 1510, a configuration profile 1520, a signal processing control unit 1530, a signal preparing unit 1540, a signal processing unit 1550 and an optional data storage 1560. The system operation initializer 1510 may be configured to, based on system configuration information read from the configuration profile 1520 and/or instructions received via the user interface 140, set up a system operation environment and initialize the functions of the signal processor 1330, in particular those of the signal processing control unit 1530. The signal processing control unit 1530 operates to generate control signals for controlling the signal preparing unit 1540 and the signal processing unit 1550, for example. It may also operate to control display of the detection results via the display control unit 120 on a display, and to control communication of data between the signal processing control unit 1550 and the communication unit 340 and/or the diagnostic unit 350. The signal preparing unit 1540 may be configured to, under the control of the signal processing control unit 1530, prepare measurement circuits, excite an AC magnetic field applied to the GMR sensors and create carrier signal applied to the measurement circuits, collect measurement signals from the measurement circuits, and feed the measurement signals after amplification and analog-to-digital-conversion to the signal processing unit 1550, in accordance with embodiments. The signal processing unit 1550 may be configured to process the received measurement signals by analytically solving for detection results, and send the detection results to the signal processing control unit 1530. Additionally, in some embodiments, the result data may be stored in the optional data storage 1560.

Figure 30:
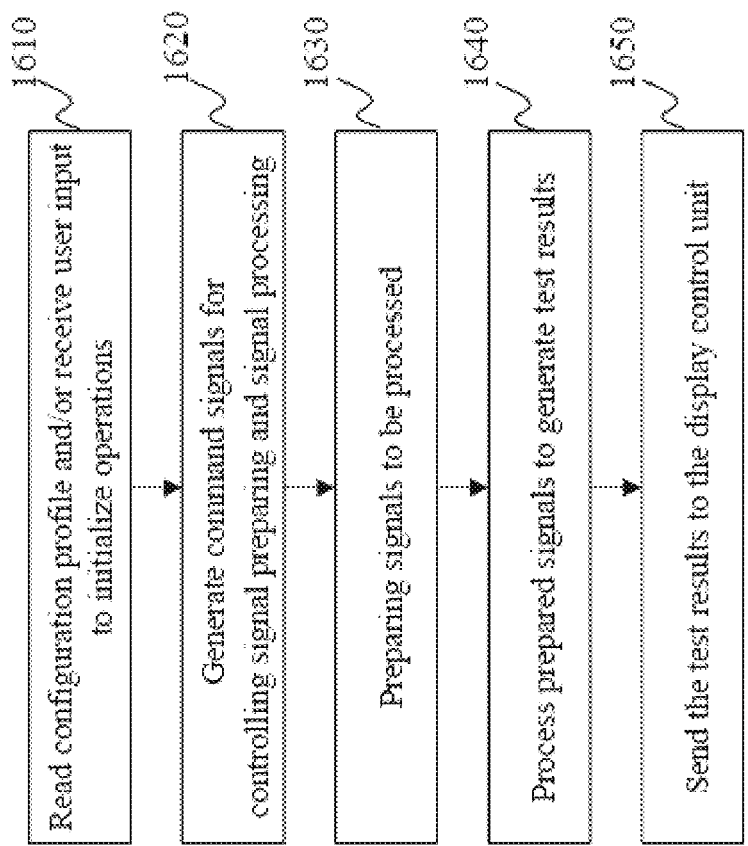
FIG. 30 is a flowchart of the process for the signal processor as noted in FIG. 30, in accordance with an embodiment of this disclosure.

FIG. 30 is a flowchart of the process for the signal processor 1330 in accordance with an embodiment. As shown in FIG. 30, the process starts at step 1610 by reading system configuration information from the configuration profile and/or receiving user instructions via the user interface 140 to initialize the system operation environment. Then, at step 1620, a series of control signals are generated by the signal processing control unit 1530 for administrating the operations of the signal preparing unit 1540 and the signal processing unit 1550. At step 1630, measurement circuits are built up by the signal preparing unit 1540 based on the control signals from the signal processing control unit 1530, so as to prepare measurement signals from the GMR sensors and the at least one reference resistor. Then, at step 1640, the prepared measurement signals are processed by the signal processing unit 1550 to solve for test results of the analyte detection. Finally, at step 1650, the generated test results are sent from the signal processing unit 1550 to the display control unit 120 for display to the user.

In accordance with embodiments herein, there is provided a system for detecting analytes in a test sample. The system includes: a cartridge reader unit comprising a control unit and a pneumatic system; and a cartridge assembly configured to receive and prepare the test sample with one or more mixing materials through communication channels therein. The cartridge assembly has a pneumatic interface and an electronic interface. The cartridge assembly further has a memory chip having parameters associated with preparing the test sample and at least one sensor for detecting the analytes in the test sample. The cartridge assembly is configured for pneumatically and electronically mating with the cartridge reader unit via the pneumatic interface and the electronic interface such that the parameters associated with preparing the test sample from the memory chip are read and implemented via the control unit of the cartridge reader unit. The pneumatic system is contained within the cartridge reader unit and comprising at least one pump and at least one valve for selectively applying fluid pressure to the pneumatic interface of the cartridge assembly and thus through the communication channels of the cartridge assembly to move the test sample and the one or more mixing materials through the communication channels and to the at least one sensor. The control unit is configured to activate the pneumatic system to prepare the test sample in the cartridge assembly based on the parameters obtained from the memory chip, and provide the test sample to the at least one sensor for detecting analytes and measurements, and further configured to process the measurements from the at least one sensor, as a result of the detected analytes, to generate test results.

In some embodiments, the cartridge reader unit further comprises a display for displaying the generated test results from the control unit. In some embodiments, the cartridge reader unit further comprises a user interface for inputting commands to the cartridge reader unit. In some embodiments, the display comprises a touch screen display and provides an input surface that acts as the user interface.

In some embodiments, the cartridge reader unit further comprises an internal battery therein for supplying power to the control unit and the pneumatic system.

In some embodiments, the cartridge reader unit further comprises an opening for receiving the cartridge assembly therein. In some embodiments, the cartridge reader unit comprises a tray that is configured to receive the cartridge assembly therein, wherein the tray is configured to move relative to the cartridge reader unit.

In some embodiments, the pneumatic control system further comprises a manifold having flow channels therein, the manifold being configured to communicate with the pneumatic interface of the cartridge assembly. In some embodiments, the pneumatic control system further comprises a plurality of syringe pumps configured to communicate with the manifold and its flow channels to selectively apply pressurized flow to the cartridge assembly. In some embodiments, the pneumatic control system further comprises a plurality of valves to control flow of pressure through the manifold and flow channels.

In some embodiments, the pneumatic control system further comprises a motor configured to activate the at least one pump.

In some embodiments, the control unit is provided in the form of a printed circuit board (PCB) assembly comprising a plurality of circuit boards.

In some embodiments, the cartridge reader unit further comprises a spring pin array therein for physically contacting the cartridge assembly for establishing communication between the control unit and the cartridge assembly.

In some embodiments, the cartridge reader unit further comprises a magnetic field generator therein, the magnetic field generator being configured for activation by the control unit to provide a magnetic field to stimulate magnetic nanoparticles near the sensor. In some embodiments, the cartridge reader unit further comprises a magnetic field generator therein, the magnetic field generator being configured for activation by the control unit to provide a non uniform magnetic field to the cartridge assembly during preparation and processing of the test sample.

In some embodiments, the control unit further comprises a signal processor configured to processes the measurements to obtain test results of analyte detection.

In some embodiments, the cartridge reader unit further comprises a puncture system to puncture or break blister packs or chambers that contain the one or more mixing materials.

In some embodiments, the cartridge assembly comprises alignment devices for aligning the cartridge assembly with the cartridge reader unit.

In some embodiments, the cartridge assembly used in the system comprises a sample processing card and a substrate attached to the sample processing card; the sample processing card comprising: an injection port for receiving the test sample within a body of the card; at least one metering chamber for receiving the test sample; fluid communication channels fluidly connecting the injection port, the at least one metering chamber, and the pneumatic interface of the cartridge assembly; and at least one output port fluidly connected to the at least one metering chamber for delivering the test sample to the sensor; the substrate having associated therewith: the sensor for sensing analytes in the test sample, the sensor being configured to receive the test sample via the at least one output port; electrical contact portions configured to establish the electrical connection with the cartridge reader unit; and the memory chip; and the pneumatic interface comprises at least one pneumatic control port and corresponding communication channel fluidly connected to the at least one metering chamber of the sample processing card, the pneumatic interface configured to enable application of positive and negative pressurized fluid from the pneumatic control system to the sample processing card to move the test sample within the communication channels and to the sensor, and wherein the memory chip stores a pneumatic system protocol that includes steps and settings for selectively applying pressure to the pneumatic interface and thus delivering at least the test sample from the sample processing card to the sensor.

In some embodiments, the pneumatic interface further comprises one or more valve control ports configured to deliver pressurized air to one or more of the plurality of valves, to move the one or more plurality of valves between the open position and the closed position. In some embodiments, the cartridge reader unit further comprises a separate pump configured to communicate with the one or more valve control ports to move the one or more plurality of valves between the open position and the closed position.

In some embodiments, the substrate comprises a printed circuit board configured to establish communication between the sensor, the electrical contact pads, and memory chip when the electrical connection is established with the cartridge reader unit.

In some embodiments, the substrate comprises a laminated layer applied to the sample processing card.

In some embodiments, the pneumatic interface is provided on the sample processing card. In some embodiments, the at least one pneumatic control port is provided on a top surface of the sample processing card.

In some embodiments, a mixing material source for introducing one or more mixing materials to the at least one metering chamber.

In some embodiments, the sensor comprises a giant magnetoresistance (GMR) sensor.

In some embodiments, there is provided a method for processing a test sample to detect analytes using the system according to any of the above embodiments. The method comprises: establishing electrical and pneumatic connections between the cartridge reader unit and the cartridge assembly via the control unit; reading the parameters associated with the memory chip for preparing the test sample; and activating the pneumatic system, using the control unit, to prepare the test sample in the cartridge assembly and provide the test sample to the at least one sensor for detecting analytes, sensing analytes and measurements of the test sample using the at least one sensor, and using the control unit to further process the measurements from the at least one sensor, as a result of the detected analytes, to generate test results.

In some embodiments, the method further comprises: loading the test sample into the cartridge assembly; and inserting the cartridge assembly into the cartridge reader unit; and mating the cartridge assembly with the cartridge reader unit.

In some embodiments, the method further comprises selectively applying pressurized air to the pneumatic interface using the pneumatic system to move the test sample and the one or more mixing materials within the communication channels and to the sensor.

In some embodiments, the method further comprises displaying the generated test results using the display. In some embodiments, the method further comprises inputting commands to the cartridge reader unit via the user interface or the display.

In some embodiments, the method further comprises inserting the cartridge assembly into the cartridge reader unit. In some embodiments, the method further comprises inserting the cartridge assembly through an opening or onto a tray of the cartridge reader unit.

In some embodiments, the method further comprises controlling one or more pumps and/or one or more valves of the pneumatic system.

In some embodiments, the method further comprises activating a magnetic field generator by the control unit to provide a magnetic field to stimulate magnetic nanoparticles near the sensor. In some embodiments, the method further comprises activating a magnetic field generator by the control unit to provide a non uniform magnetic field to the cartridge assembly during preparation and processing of the test sample.

In some embodiments, the method further comprises processing the measurements using a signal processor of the control unit to obtain test results of analyte detection.

In some embodiments, the method further comprises puncturing or breaking blister packs or chambers that contain the one or more mixing materials using a puncture system.

In some embodiments, the method further comprises aligning the cartridge assembly with the cartridge reader unit using alignment devices.

In some embodiments, the method further comprises sensing by a giant magnetoresistance (GMR) sensor.

While the principles of the disclosure have been made clear in the illustrative embodiments set forth above, it will be apparent to those skilled in the art that various modifications may be made to the structure, arrangement, proportion, elements, materials, and components used in the practice of the disclosure.

It will thus be seen that the features of this disclosure have been fully and effectively accomplished. It will be realized, however, that the foregoing preferred specific embodiments have been shown and described for the purpose of illustrating the functional and structural principles of this disclosure and are subject to change without departure from such principles. Therefore, this disclosure includes all modifications encompassed within the spirit and scope of the following claims.

What is claimed is:

1. A system for detecting analytes in a test sample, the system comprising:
   a cartridge reader unit comprising a control unit and a pneumatic system; and
   a cartridge assembly configured to receive and prepare the test sample with one or more mixing materials through communication channels therein, the cartridge assembly comprising a pneumatic interface and an electronic interface;
   the cartridge assembly further comprising a memory chip having parameters associated with preparing the test sample and at least one sensor for detecting the analytes in the test sample;
   the cartridge assembly being configured for pneumatically and electronically mating with the cartridge reader unit via the pneumatic interface and the electronic interface such that the parameters associated with preparing the test sample from the memory chip are read and implemented via the control unit of the cartridge reader unit;
   the pneumatic system being contained within the cartridge reader unit and comprising at least one pump and at least one valve for selectively applying fluid pressure to the pneumatic interface of the cartridge assembly and thus through the communication channels of the cartridge assembly to move the test sample and the one or more mixing materials through the communication channels and to the at least one sensor; and
   the control unit configured to activate the pneumatic system to prepare the test sample in the cartridge assembly based on the parameters obtained from the memory chip, and provide the test sample to the at least one sensor for detecting analytes and measurements, and further configured to process the measurements from the at least one sensor, as a result of the detected analytes, to generate test results.

2. The system according to claim 1, wherein the cartridge reader unit further comprises a display for displaying the generated test results from the control unit.

3. The system according to claim 1, wherein the cartridge reader unit further comprises a user interface for inputting commands to the cartridge reader unit.

4. The system according to claim 1, wherein the pneumatic system further comprises a manifold having flow channels therein, the manifold being configured to communicate with the pneumatic interface of the cartridge assembly.

5. The system according to claim 4, wherein the pneumatic system further comprises a plurality of syringe pumps configured to communicate with the manifold and flow channels to selectively apply pressurized flow to the cartridge assembly.

6. The system according to claim 4, wherein the pneumatic system further comprises a plurality of valves to control flow of pressure through the manifold and flow channels.

7. The system according to claim 1, wherein the cartridge reader unit further comprises a spring pin array therein for physically contacting the cartridge assembly for establishing communication between the control unit and the cartridge assembly.

8. The system according to claim 1, wherein the cartridge reader unit further comprises a magnetic field generator therein, the magnetic field generator being configured for activation by the control unit to provide (a) a magnetic field to stimulate magnetic nanoparticles near the sensor and/or (b) a non uniform magnetic field to the cartridge assembly during preparation and processing of the test sample.

9. The system according to claim 1, wherein the cartridge reader unit further comprises a puncture system to puncture or break blister packs or chambers that contain the one or more mixing materials.

10. The system according to claim 1, wherein the cartridge assembly comprises a sample processing card and a substrate attached to the sample processing card;
   the sample processing card comprising:
      an injection port for receiving the test sample within a body of the card; and
      at least one output port fluidly connected to the at least one metering chamber for delivering the test sample to the sensor;
   the substrate having associated therewith:
      the sensor for sensing analytes in the test sample, the sensor being configured to receive the test sample via the at least one output port;
      electrical contact portions configured to establish the electrical connection with the cartridge reader unit; and
      the memory chip;
   and
   wherein the pneumatic interface is configured to enable application of positive and negative pressurized fluid from the pneumatic system to the sample processing card to move the test sample within the communication channels and body and to the sensor, and wherein the memory chip stores a pneumatic system protocol that includes steps and settings for selectively applying pressure to the pneumatic interface and thus delivering at least the test sample from the sample processing card to the sensor.

11. The system according to claim 10, wherein the substrate comprises a printed circuit board configured to establish communication between the sensor, the electrical contact pads, and memory chip when the electrical connection is established with the cartridge reader unit.

12. The system according to claim 1, wherein the sensor comprises a giant magnetoresistance (GMR) sensor.

13. A method for processing a test sample to detect analytes using the system according to claim 1, the method comprising:
 establishing electrical and pneumatic connections between the cartridge reader unit and the cartridge assembly via the control unit;
 reading the parameters associated with the memory chip for preparing the test sample;
 activating the pneumatic system, using the control unit, to prepare the test sample in the cartridge assembly and provide the test sample to the at least one sensor for detecting analytes,
 sensing analytes and measurements of the test sample using the at least one sensor, and
 using the control unit to further process the measurements from the at least one sensor, as a result of the detected analytes, to generate test results.

14. The method according to claim 13, further comprising:
 loading the test sample into the cartridge assembly;
 inserting the cartridge assembly into the cartridge reader unit; and
 mating the cartridge assembly with the cartridge reader unit.

15. The method according to claim 13, further comprising:
 selectively applying pressurized air to the pneumatic interface using the pneumatic system to move the test sample and the one or more mixing materials within the communication channels and to the sensor.

16. The method according to claim 13, further comprising controlling one or more pumps and/or one or more valves of the pneumatic system.

17. The method according to claim 13, further comprising activating a magnetic field generator by the control unit to provide (a) a magnetic field to stimulate magnetic nanoparticles near the sensor and/or (b) a non uniform magnetic field to the cartridge assembly during preparation and processing of the test sample.

18. The method according to claim 13, further comprising processing the measurements using a signal processor of the control unit to obtain test results of analyte detection.

19. The method according to claim 13, further comprising puncturing or breaking blister packs or chambers that contain the one or more mixing materials using a puncture system.

20. The method according to claim 13, wherein the sensing is performed by a giant magnetoresistance (GMR) sensor.

* * * * *